United States Patent
Kim et al.

(10) Patent No.: US 8,120,243 B2
(45) Date of Patent: Feb. 21, 2012

(54) MATERIAL FOR ORGANIC PHOTOELECTRIC DEVICE, AND ORGANIC PHOTOELECTRIC DEVICE THEREBY

(75) Inventors: Young-Hoon Kim, Anyang-si (KR); Eun-Sun Yu, Anyang-si (KR); Nam-Soo Kim, Bucheon-si (KR); Mi-Young Chae, Yongin-si (KR)

(73) Assignee: Cheil Industries, Inc., Gumi-si, Gyeongsangbuk-do (KR)

( * ) Notice: Subject to any disclaimer, the term of this patent is extended or adjusted under 35 U.S.C. 154(b) by 0 days.

(21) Appl. No.: 12/662,765

(22) Filed: May 3, 2010

(65) Prior Publication Data

US 2010/0213826 A1 Aug. 26, 2010

Related U.S. Application Data

(63) Continuation of application No. PCT/KR2008/006452, filed on Oct. 31, 2008.

(30) Foreign Application Priority Data

Nov. 1, 2007 (KR) .................. 10-2007-0110984

(51) Int. Cl.
- *C09K 11/06* (2006.01)
- *H01L 51/54* (2006.01)
- *H05B 33/14* (2006.01)
- *C07D 209/82* (2006.01)

(52) U.S. Cl. ... 313/504; 313/506; 257/40; 257/E51.051; 428/690; 428/917; 548/440

(58) Field of Classification Search .................. None
See application file for complete search history.

(56) References Cited

U.S. PATENT DOCUMENTS 4,769,292 A * 9/1988 Tang et al. .................. 428/690
(Continued)

FOREIGN PATENT DOCUMENTS

EP 0 926 216 A1 6/1999
(Continued)

OTHER PUBLICATIONS

Brown et al., Australian Journal of Chemistry, (1970), vol. 23, No. 3, pp. 625-627.*
(Continued)

*Primary Examiner* — Jennifer A Chriss
*Assistant Examiner* — Brett A Crouse
(74) *Attorney, Agent, or Firm* — Lee & Morse, P.C.

(57) ABSTRACT

A material for an organic photoelectric device, the material including a compound represented by the following Chemical Formula 1:

[Chemical Formula 1]

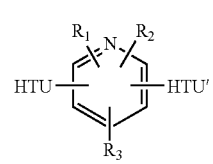

wherein, in Chemical Formula 1,
HTU and HTU' are independently hole transporting units, and
$R_1$ to $R_3$ are independently a substituent selected from the group of hydrogen, a substituted or unsubstituted C6 to C30 aryl, a substituted or unsubstituted C2 to C30 heteroaryl, and a substituted or unsubstituted C1 to C30 alkyl,
wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

6 Claims, 3 Drawing Sheets

U.S. PATENT DOCUMENTS

| | | | | |
|---|---|---|---|---|
| 2004/0086745 A1* | 5/2004 | Iwakuma et al. | ............. | 428/690 |
| 2006/0186796 A1* | 8/2006 | Yabe et al. | .................... | 313/504 |
| 2007/0190355 A1* | 8/2007 | Ikeda et al. | ................... | 428/690 |
| 2008/0067922 A1* | 3/2008 | Endo et al. | .................... | 313/504 |
| 2008/0145699 A1 | 6/2008 | Yabe et al. | | |

FOREIGN PATENT DOCUMENTS

| | | | |
|---|---|---|---|
| JP | 07-011246 A | | 1/1995 |
| JP | 2000-169448 | | 6/2000 |
| JP | 2001-131150 | | 5/2001 |
| JP | 2004-095262 | | 3/2004 |
| JP | 2007-169268 A | | 7/2007 |
| WO | WO 2006/040915 | * | 4/2006 |

OTHER PUBLICATIONS

Baldo, A.M., et al., "Very high-efficiency green organic light-emitting devices based on electrophosphorescence", Applied Physics Letters, 75(1):4-6 *1999).

O'Brien, D.F., et al., "Improved energy transfer in electrophosphorescent devices", Applied Physics Letters, 75(3):442-444 (1999).

Tang, C.W., et al., "Organic electroluminescent diodes", Applied Physics Letters, 51(12):913-915 (1987).

* cited by examiner

MATERIAL FOR ORGANIC PHOTOELECTRIC DEVICE, AND ORGANIC PHOTOELECTRIC DEVICE THEREBY

CROSS-REFERENCE TO RELATED APPLICATION

This application is a continuation of pending International Application No. PCT/KR2008/006452, entitled "Material for Organic Photoelectric Device, and Organic Photoelectric Device Thereby," which was filed on Oct. 31, 2008, the entire contents of which are hereby incorporated by reference.

BACKGROUND

1. Field

Embodiments relate to a material for an organic photoelectric device, and an organic photoelectric device using the same.

2. Description of the Related Art

A photoelectric device is, in a broad sense, a device for transforming photo energy to electrical energy, and conversely, for transforming electrical energy to photo energy. The photoelectric device may be exemplified by an organic light emitting diode, a solar cell, a transistor, and so on.

Particularly, among these photoelectric devices, the organic light emitting device employing organic light emitting diodes (OLED) has recently drawn attention due to the increase in demand for flat panel displays.

The organic light emitting device transforms electrical energy into light by applying current to an organic light emitting material. It has a structure in which a functional organic material layer is interposed between an anode and a cathode.

The organic light emitting diode has similar electrical characteristics to those of light emitting diodes (LEDs) in which holes are injected from an anode and electrons are injected from a cathode, and then the holes and electrons move to opposite electrodes and are recombined to form excitons having high energy. The formed excitons generate light having a certain wavelength while shifting to a ground state.

In 1987, Eastman Kodak, Inc., developed an organic light emitting diode including a low molecular weight aromatic diamine and an aluminum complex as an emission-layer-forming material (Applied Physics Letters. 51, 913, 1987). C. W. Tang et al. disclosed a practicable device as an organic light emitting diode in 1987 (Applied Physics Letters, 51 12, 913-915, 1987).

The organic layer may have a structure in which a thin film (hole transport layer (HTL)) of a diamine derivative and a thin film of tris(8-hydroxy-quinolate)aluminum ($Alq_3$) are laminated. The $Alq_3$ thin film of $Alq_a$ functions as an emission layer for transporting electrons.

Generally, the organic light emitting diode is composed of an anode of a transparent electrode, an organic thin layer of a light emitting region, and a metal electrode (cathode) formed on a glass substrate, in that order. The organic thin layer may include an emission layer, a hole injection layer (HIL), a hole transport layer (HTL), an electron transport layer (ETL), and an electron injection layer (EIL). It may further include an electron blocking layer or a hole blocking layer according to emission characteristics of the emission layer.

When an electric field is applied to the organic light emitting diode, the holes and electrons are injected from the anode and the cathode, respectively. The injected holes and electrons are recombined on the emission layer through the hole transport layer (HTL) and the electron transport layer (ETL) to provide light emitting excitons. The provided light emitting excitons emit light by transition to a ground state.

The light emitting material may be classified as a fluorescent material including singlet excitons and a phosphorescent material including triplet excitons.

The phosphorescent light emitting material may be useful as a light emitting material (D. F. O'Brien et al., Applied Physics Letters, 74 3, 442-444, 1999; M. A. Baldo et al., Applied Physics letters, 75 1, 4-6, 1999). Such phosphorescent emission occurs by transition of electrons from the ground state to the exited state, non-radiative transition of a singlet exciton to a triplet exciton through intersystem crossing, and transition of the triplet exciton to the ground state to emit light.

When the triplet exciton transitions, it cannot directly transition to the ground state. Therefore, the electron spin is flipped, and then it transitions to the ground state. Thus, it provides a characteristic of extended lifetime (emission duration) relative to than that of fluorescent emission.

In other words, the duration of fluorescent emission is extremely short (at several nanoseconds), but the duration of phosphorescent emission is relatively long (such as several microseconds), so that phosphorescent emission provides a characteristic of extending the lifetime (emission duration) to more than that of the fluorescent emission.

Quantum mechanically, when holes injected from the anode are recombined with electrons injected from the cathode to provide light emitting excitons, the singlet and the triplet are produced in a ratio of 1:3, in which the triplet light emitting excitons are produced at three times the amount of the singlet light emitting excitons in the organic light emitting diode.

Accordingly, the percentage of the singlet exited state is 25% (the triplet is 75%) in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach up to 100%. When a phosphorescent light emitting material is used, it has advantages in an increase in luminous efficiency of around four times that of the fluorescent light emitting material.

In the above-mentioned organic light emitting diode, a light emitting colorant (dopant) may be added to an emission layer (host) in order to increase the efficiency and stability in the emission state.

SUMMARY

Embodiments are directed to a material for an organic photoelectric device, and an organic photoelectric device using the same, which substantially overcome one or more of the problems due to the limitations and disadvantages of the related art.

It is a feature of an embodiment to provide a material for an organic photoelectric device having thermal stability and good hole and electron transporting properties, and being capable of realizing a high efficiency organic photoelectric device.

At least one of the above and other features and advantages may be realized by providing a material for an organic photoelectric device, the material including a compound represented by the following Chemical Formula 1:

[Chemical Formula 1]

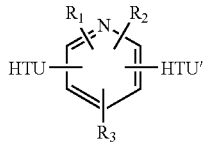

wherein, in Chemical Formula 1,

HTU and HTU' are independently hole transporting units, and $R_1$ to $R_3$ are independently a substituent selected from the group of hydrogen, a substituted or unsubstituted C6 to C30 aryl, a substituted or unsubstituted C2 to C30 heteroaryl, and a substituted or unsubstituted C1 to C30 alkyl, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The compound represented by Chemical Formula 1 may be represented by the following Chemical Formula 2:

[Chemical Formula 2]

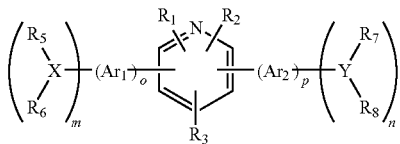

wherein, in Chemical Formula 2,

X and Y are independently selected from the group of nitrogen, sulfur, and oxygen, $Ar_1$ and $Ar_2$ are independently selected from the group of a substituted or unsubstituted C6 to C30 aryl or arylene, a substituted or unsubstituted C1 to C30 alkyl or alkylene, and a substituted or unsubstituted C2 to C30 heteroaryl or heteroarylene, $R_1$ to $R_3$ are independently selected from the group of hydrogen, a substituted or unsubstituted C6 to C30 aryl, a substituted or unsubstituted C2 to C30 heteroaryl, and a substituted or unsubstituted C1 to C30 alkyl, $R_5$ to $R_8$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene, $R_5$ and $R_6$ are independently separate substituents or are joined together to form a ring, and $R_7$ and $R_8$ are independently separate substituents or are joined together to form a ring, when X is sulfur or oxygen, at least one of $R_5$ or $R_6$ is a lone pair electron, and when Y is sulfur or oxygen, at least one of $R_7$ or $R_8$ is a lone pair electron, m and n are integers ranging from 0 to 3, m+n is an integer ranging from 1 to 6, and o and p are integers ranging from 0 to 2, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The compound represented by Chemical Formula 1 may be represented by the following Chemical Formula 3:

[Chemical Formula 3]

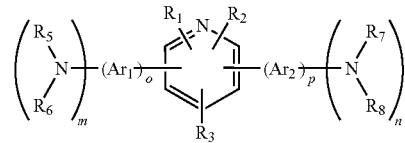

wherein, in Chemical Formula 3, $Ar_1$ and $Ar_2$ are independently selected from the group of a substituted or unsubstituted C6 to C30 aryl or arylene, a substituted or unsubstituted C1 to C30 alkyl or alkylene, and a substituted or unsubstituted C2 to C30 heteroaryl or heteroarylene, $R_1$ to $R_3$ are independently selected from the group of hydrogen, a substituted or unsubstituted C6 to C30 aryl, a substituted or unsubstituted C2 to C30 heteroaryl, and a substituted or unsubstituted C1 to C30 alkyl, $R_5$ to $R_8$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene, $R_5$ and $R_6$ are independently separate substituents or are joined together to form a ring, and $R_7$ and $R_8$ are independently separate substituents or are joined together to form a ring, m and n are integers ranging from 0 to 3, m+n is an integer ranging from 1 to 6, and o and p are integers ranging from 0 to 2, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The substituents linked to the side chains of $Ar_1$ and $Ar_2$ in Chemical Formula 3 may be independently selected from the group of a substituent of the following Chemical Formula 4 and a substituent of the following Chemical Formula 5:

[Chemical Formula 4]

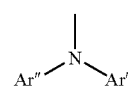

wherein, in Chemical Formula 4,

Ar' and Ar" are independently selected from the group of phenyl, naphthyl, anthryl, phenanthryl, naphthacenyl, pyrenyl, biphenylyl, terphenylyl, tolyl, pyrrol, pyrazinyl, pyrimidyl, pyridazinyl, pyridinyl, indolyl, puryl, benzofuranyl, quinolyl, quinoxalinyl, phenanthridinyl, acridinyl, phenanthrolinyl, phenazinyl, phenothiazinyl, phenoxazinyl, oxazolyl, oxadiazolyl, and thienyl;

[Chemical Formula 5]

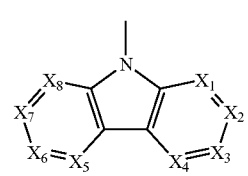

wherein, in Chemical Formula 5, $X_1$ to $X_8$ are independently selected from the group of CR' and N, and R' is selected from the group of hydrogen, a substituted or unsubstituted C6 to C30 aryl, a substituted or unsubstituted C2 to C30 heteroaryl, and a substituted or unsubstituted C1 to C30 alkyl, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The compound represented by Chemical Formula 1 may be represented by the following Chemical Formula 6:

[Chemical Formula 6]

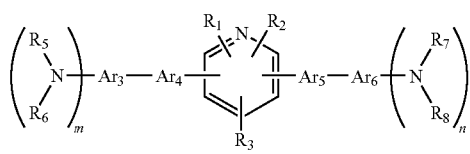

wherein, in Chemical Formula 6, $Ar_3$ and $Ar_6$ are independently selected from the group of a substituted or unsubstituted C6 to C30 aryl or arylene, a substituted or unsubstituted C1 to C30 alkyl or alkylene, and a substituted or unsubstituted C2 to C30 heteroaryl or heteroarylene, $Ar_4$ and $Ar_5$ are independently selected from the group of a substituted or unsubstituted C6 to C30 arylene, a substituted or unsubstituted C1 to C30 alkylene, and a substituted or unsubstituted C2 to C30 heteroarylene, $R_1$ to $R_3$ are independently selected from the group of hydrogen, a substituted or unsubstituted C6 to C30 aryl, a substituted or unsubstituted C2 to C30 heteroaryl, and a substituted or unsubstituted C1 to C30 alkyl, $R_5$ to $R_8$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene, $R_5$ and $R_6$ are independently separate substituents or are joined together to form a ring, and $R_7$ and $R_8$ are independently separate substituents or are joined together to form a ring, and m and n are integers ranging from 0 to 3, and m+n is an integer ranging from 1 to 6, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The compound represented by Chemical Formula 1 may be represented by the following Chemical Formula 7:

[Chemical Formula 7]

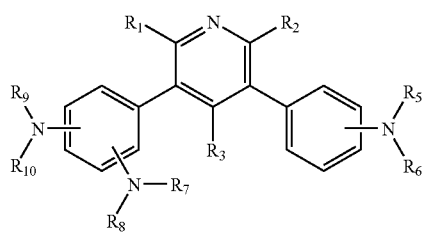

wherein, in Chemical Formula 7, $R_1$ to $R_3$ are independently selected from the group of hydrogen, a substituted or unsubstituted C6 to C30 aryl, a substituted or unsubstituted C2 to C30 heteroaryl, and a substituted or unsubstituted C1 to C30 alkyl, $R_5$ to $R_{10}$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene, and $R_5$ and $R_6$ are independently separate substituents or are joined together to form a ring, $R_7$ and $R_8$ are independently separate substituents or are joined together to form a ring, and $R_9$ and $R_{10}$ are independently separate substituents or are joined together to form a ring, wherein the term "substituted" refers to one substituted with a halogen, a C1 to C30 alkyl, a C1 to C30 haloalkyl, a C6 to C30 aryl, a C2 to C30 heteroaryl, a C1 to C20 alkoxy, or combinations thereof.

The compound represented by Chemical Formula 1 may be selected from compounds represented by the following Chemical Formulae 1-1 to 1-5:

[Chemical Formula 1-1]

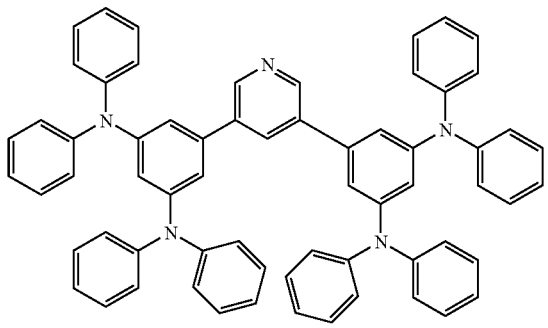

[Chemical Formula 1-2]

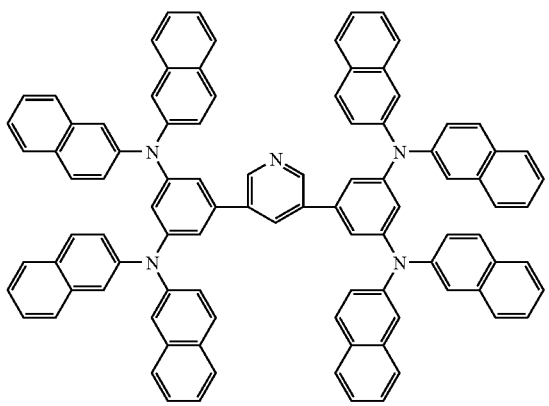

[Chemical Formula 1-3]
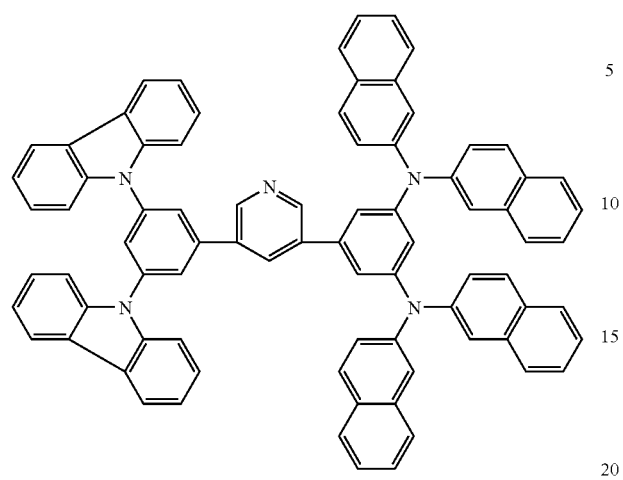
[Chemical Formula 1-4]
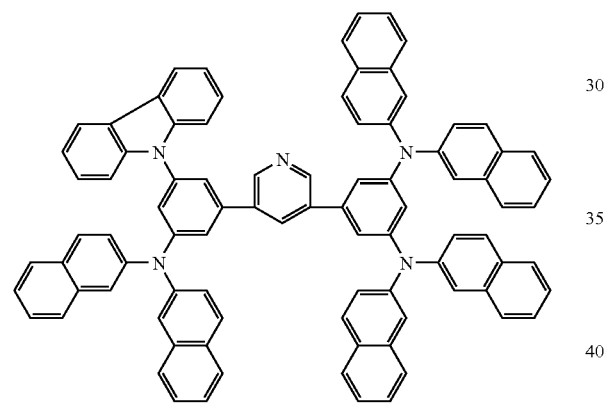
[Chemical Formula 1-5]
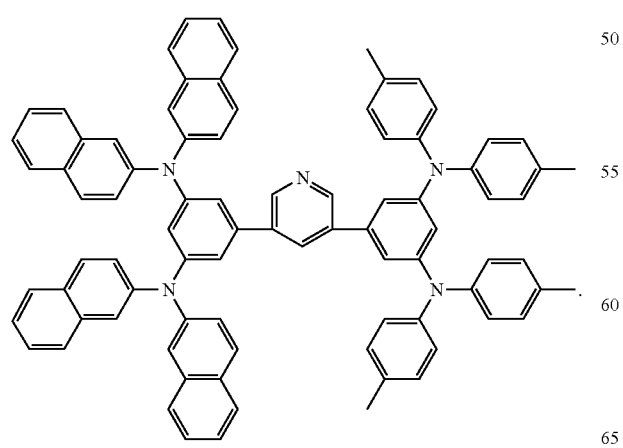
The compound represented by Chemical Formula 1 may be selected from compounds represented by the following Chemical Formulae 1-6 to 1-10:
[Chemical Formula 1-6]
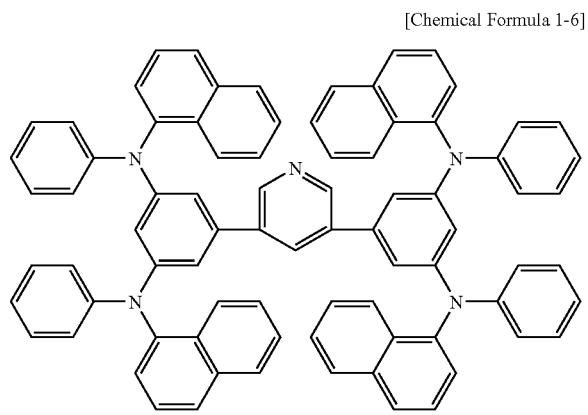
[Chemical Formula 1-7]
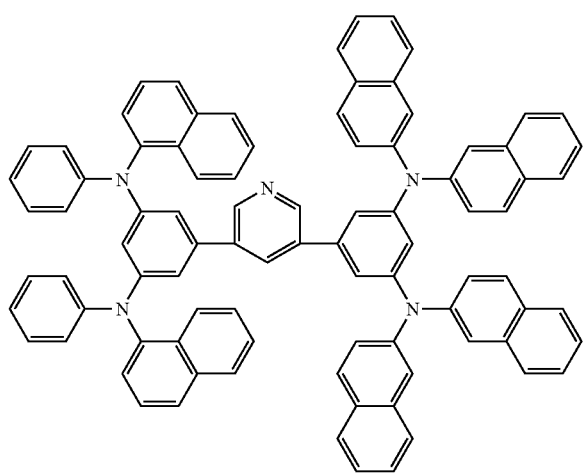

[Chemical Formula 1-8]
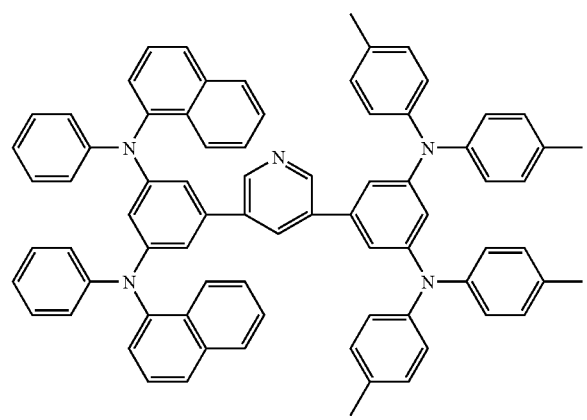
[Chemical Formula 1-9]
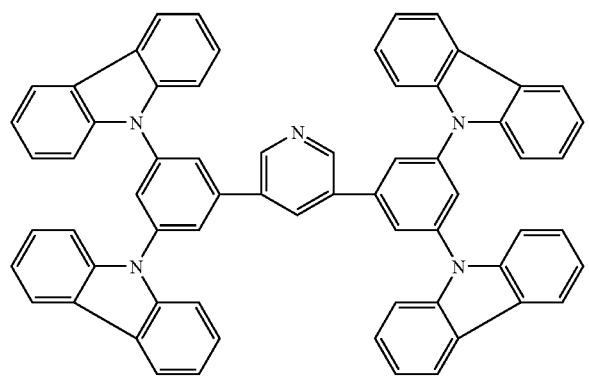
[Chemical Formula 1-10]
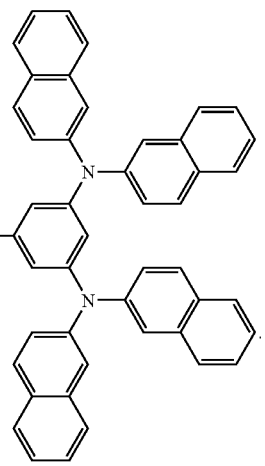
The compound represented by Chemical Formula 1 may be selected from compounds represented by the following Chemical Formulae 1-11 to 1-15:
[Chemical Formula 1-11]
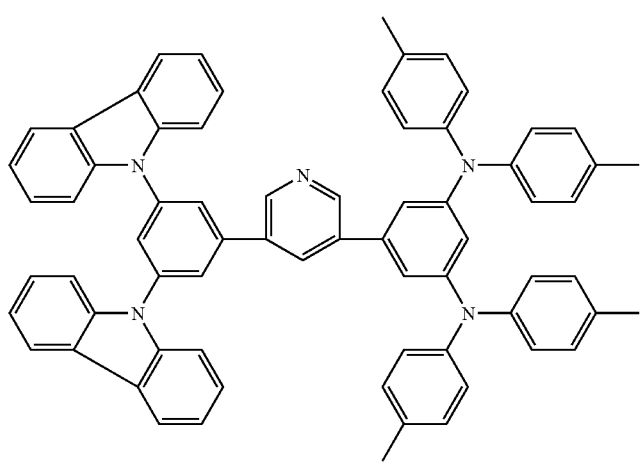

-continued
[Chemical Formula 1-12]
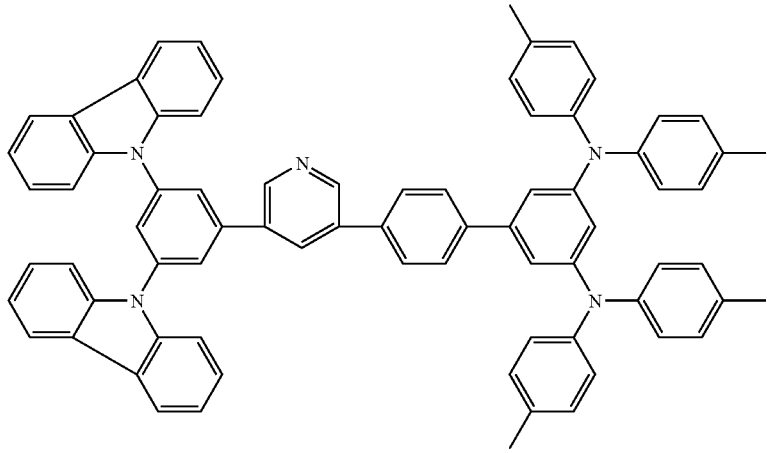
[Chemical Formula 1-13]
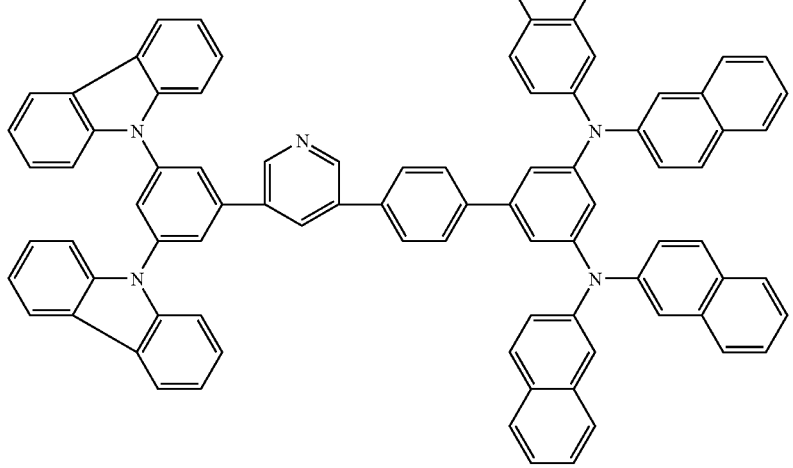
[Chemical Formula 1-14]
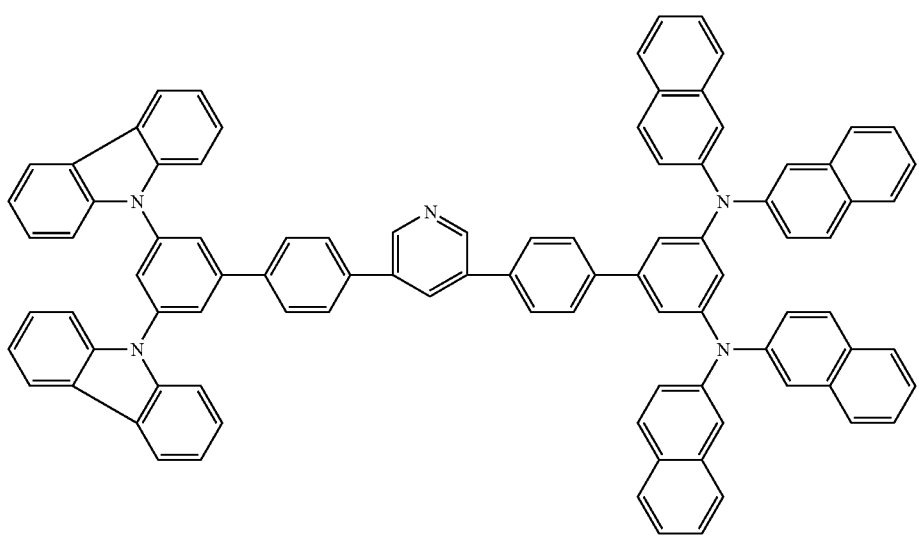

[Chemical Formula 1-15]
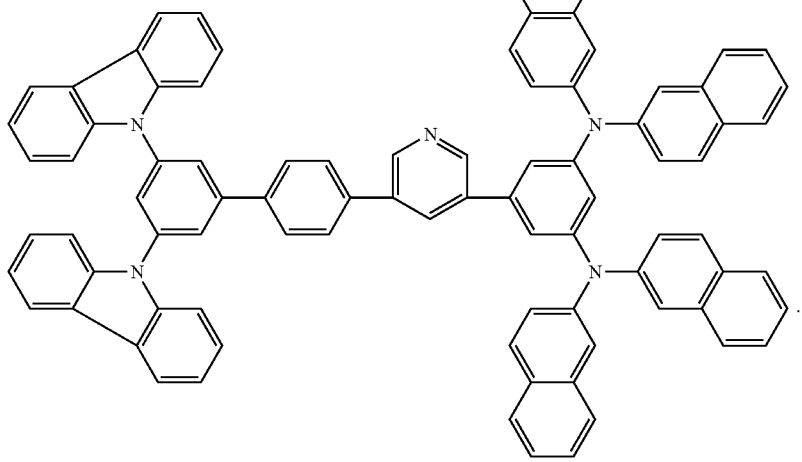
The compound represented by Chemical Formula 1 may be selected from compounds represented by the following Chemical Formulae 1-16 to 1-20:
[Chemical Formula 1-16]
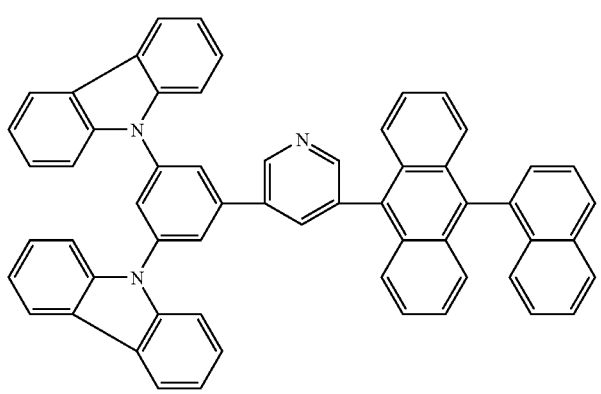
[Chemical Formula 1-17]
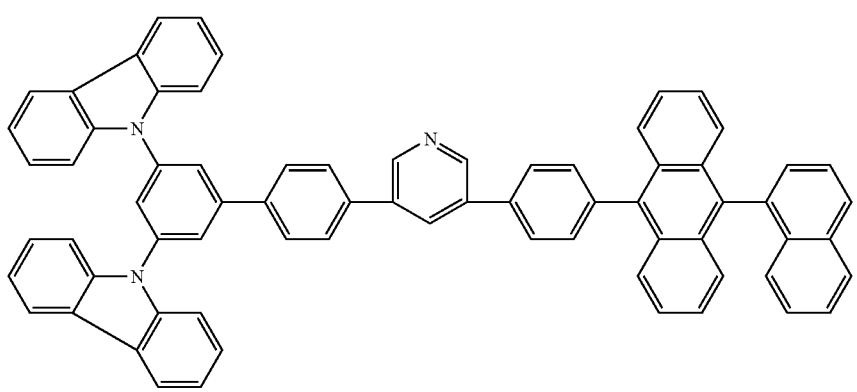

[Chemical Formula 1-18]
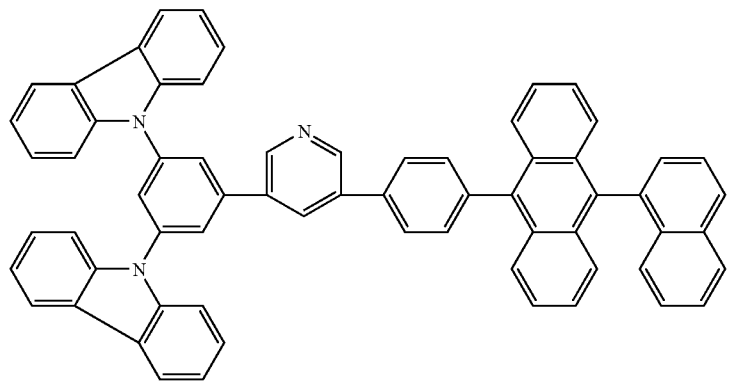
[Chemical Formula 1-19]
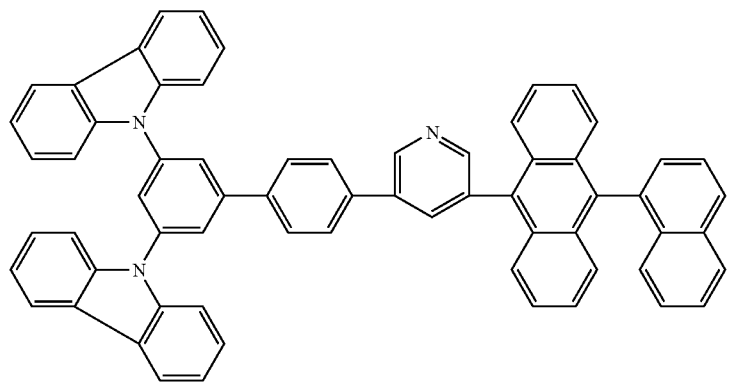
[Chemical Formula 1-20]
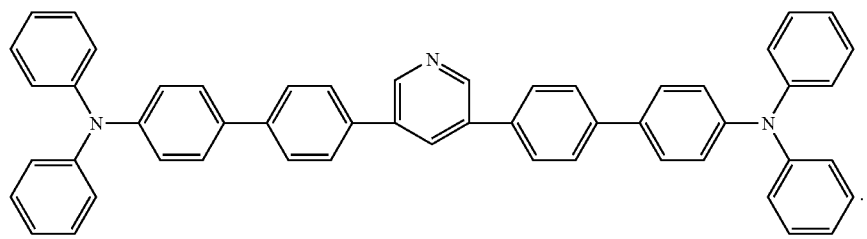
The compound represented by Chemical Formula 1 may be selected from compounds represented by the following Chemical Formulae 1-21 to 1-25:
[Chemical Formula 1-21]
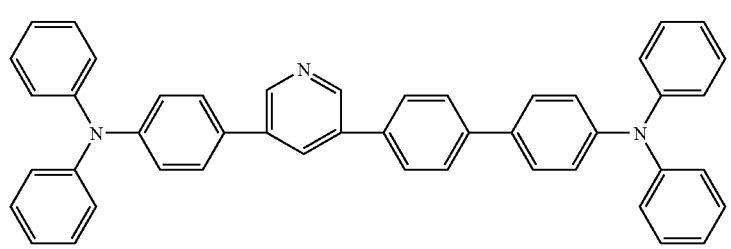
[Chemical Formula 1-22]
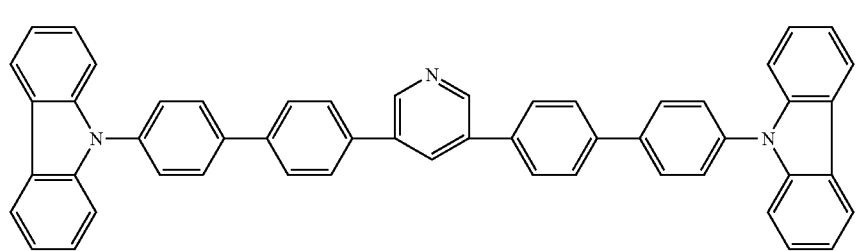

[Chemical Formula 1-23]
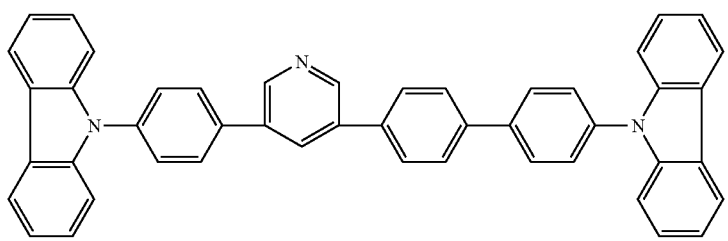
[Chemical Formula 1-24]
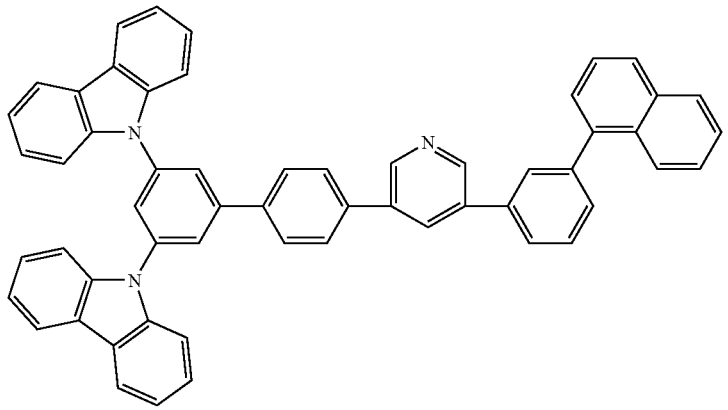
[Chemical Formula 1-25]
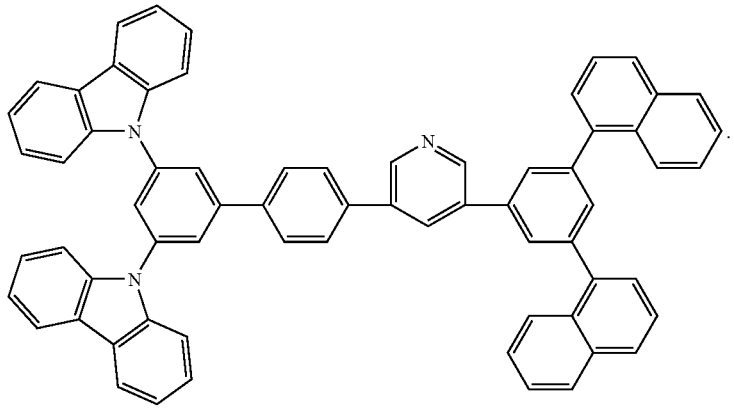
The compound represented by Chemical Formula 1 may be selected from compounds represented by the following Chemical Formulae 1-26 to 1-30:
[Chemical Formula 1-26]
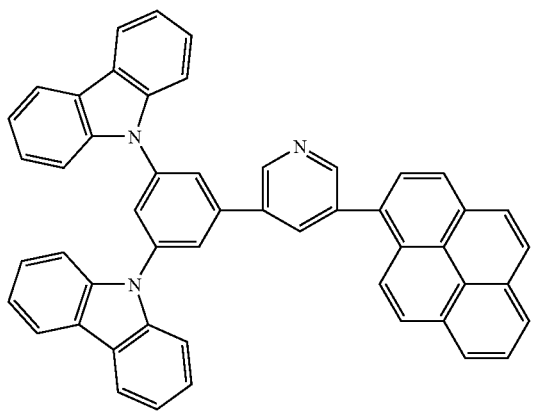

[Chemical Formula 1-27]
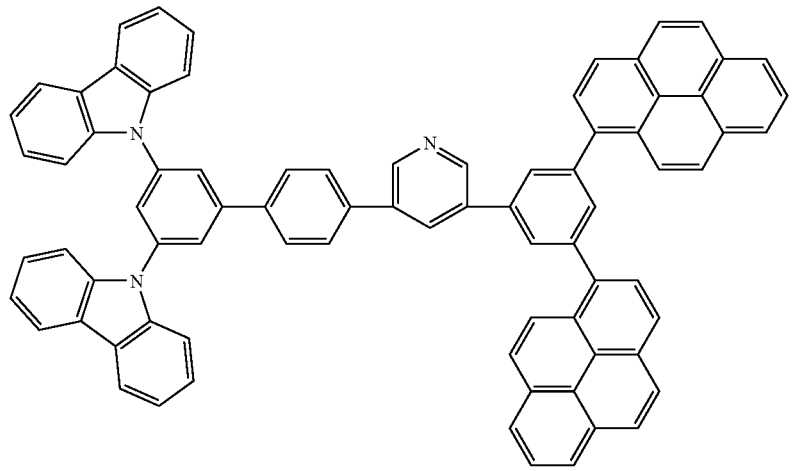
[Chemical Formula 1-28]
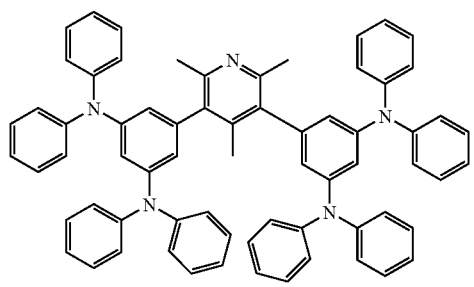
[Chemical Formula 1-29]
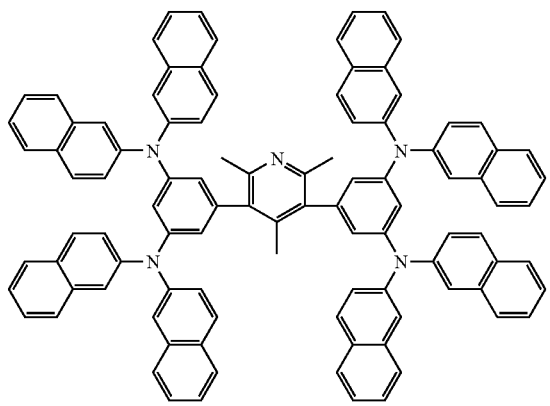
[Chemical Formula 1-30]
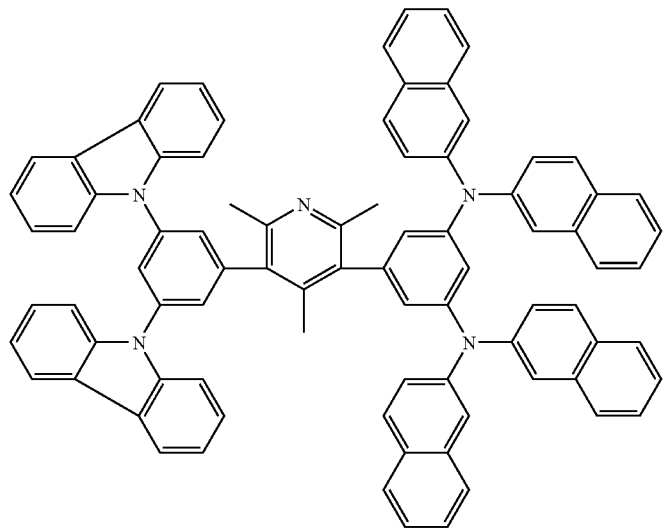

The compound represented by Chemical Formula 1 may be selected from compounds represented by the following Chemical Formulae 1-31 to 1-35:
[Chemical Formula 1-31]
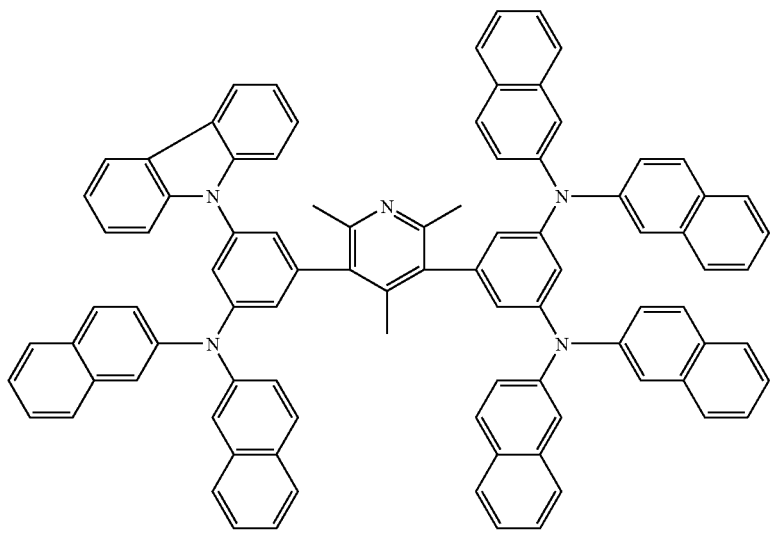
[Chemical Formula 1-32]
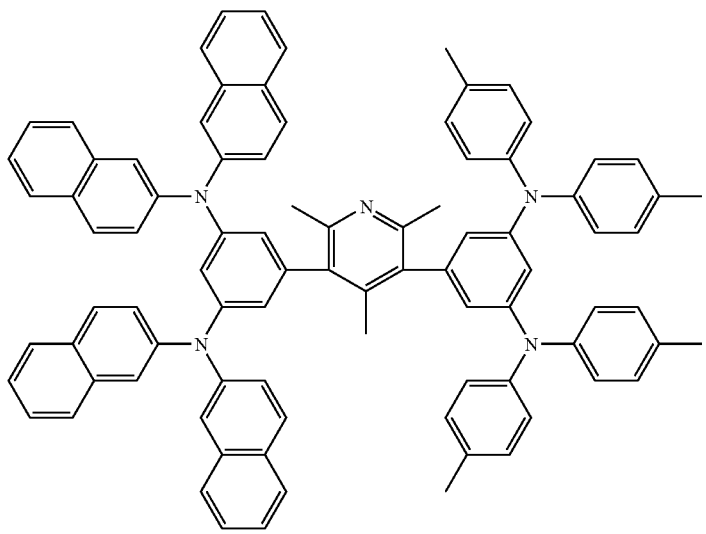
[Chemical Formula 1-33]
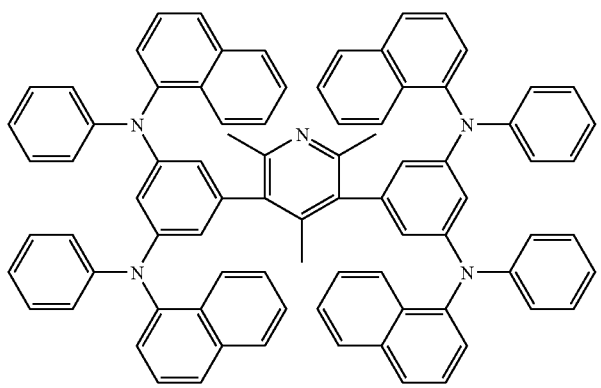

[Chemical Formula 1-34]
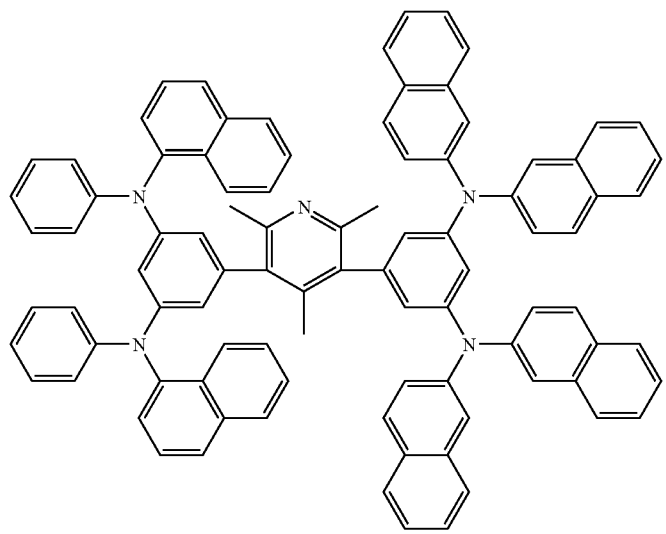
[Chemical Formula 1-35]
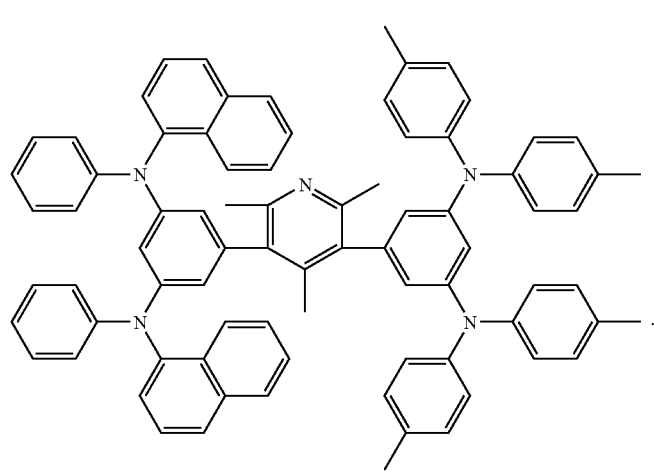

The compound represented by Chemical Formula 1 may be selected from compounds represented by the following Chemical Formulae 1-36 to 1-40:
[Chemical Formula 1-36]
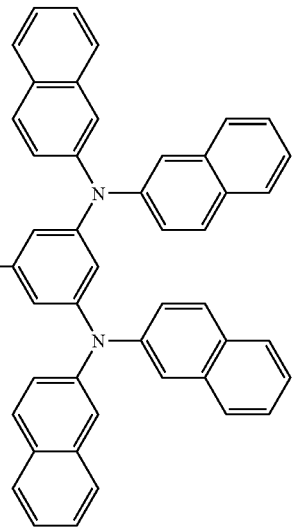
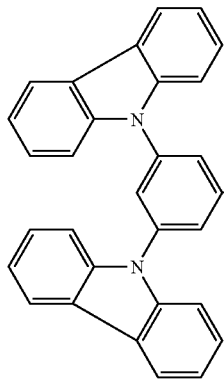
[Chemical Formula 1-37]
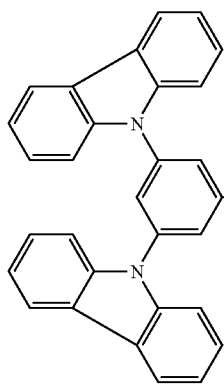
[Chemical Formula 1-38]
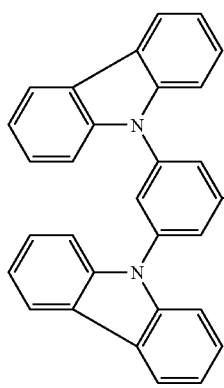

[Chemical Formula 1-39]
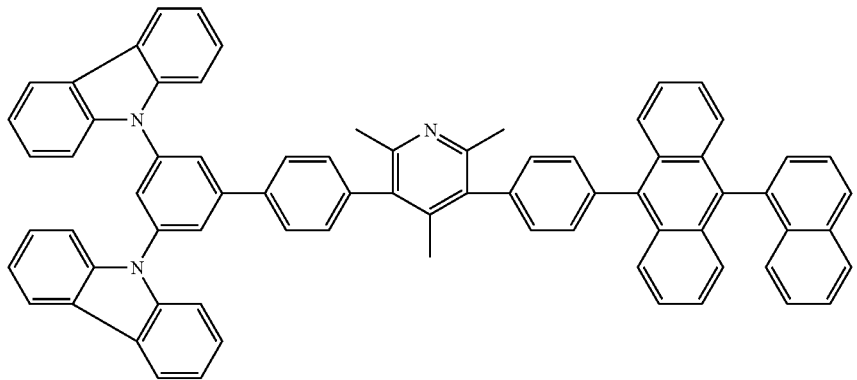
[Chemical Formula 1-40]
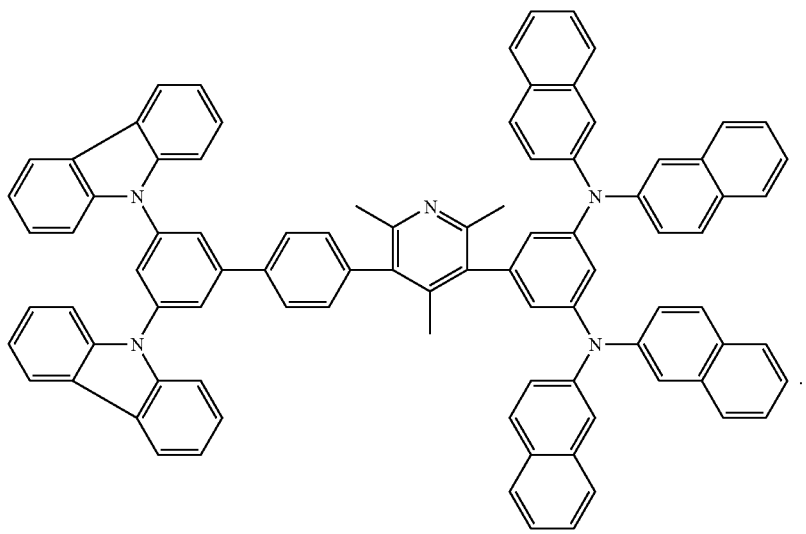
The compound represented by Chemical Formula 1 may be selected from compounds represented by the following Chemical Formulae 1-41 to 1-45:
[Chemical Formula 1-41]
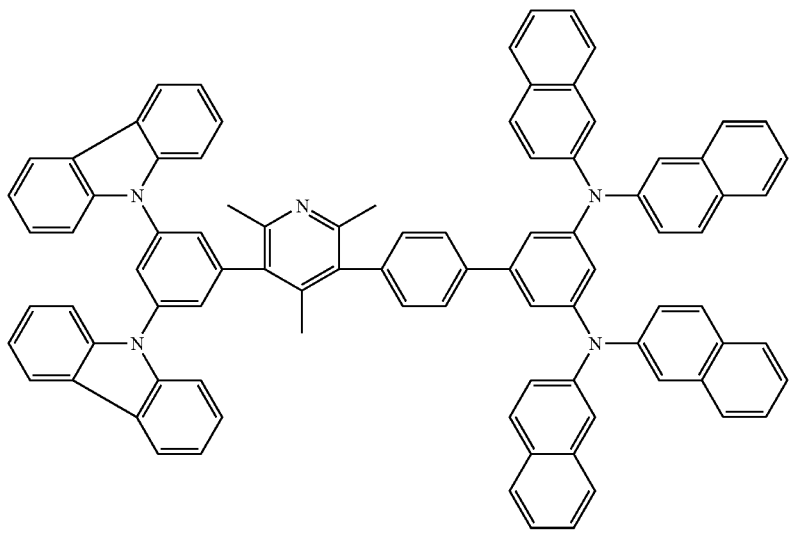

[Chemical Formula 1-42]
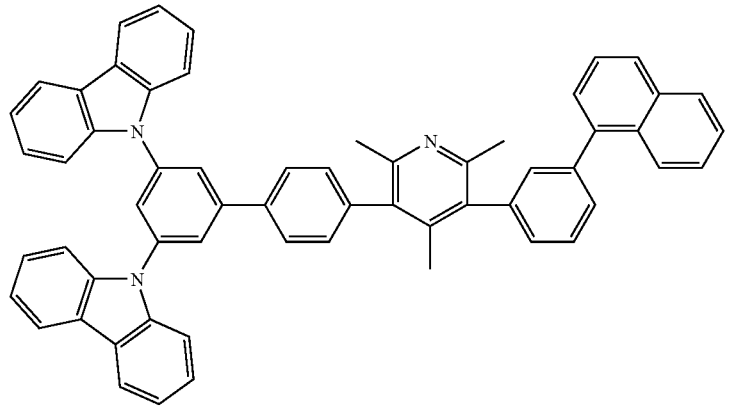
[Chemical Formula 1-43]
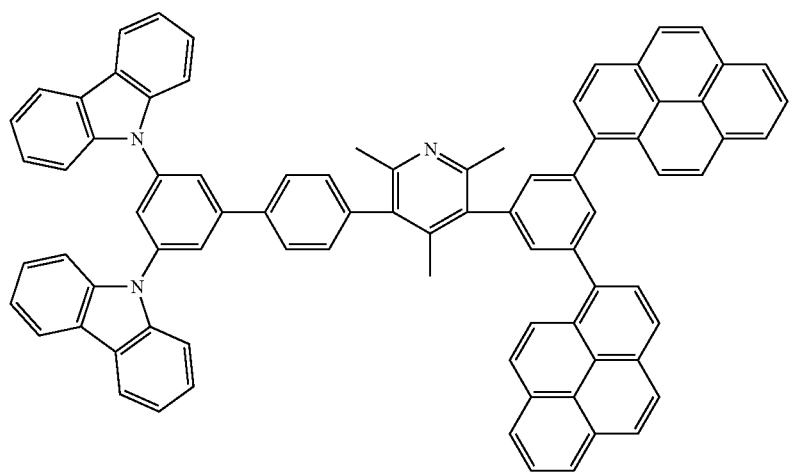
[Chemical Formula 1-44]
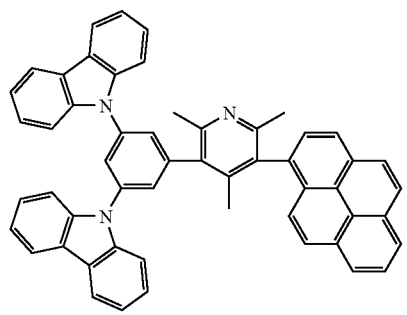
[Chemical Formula 1-45]
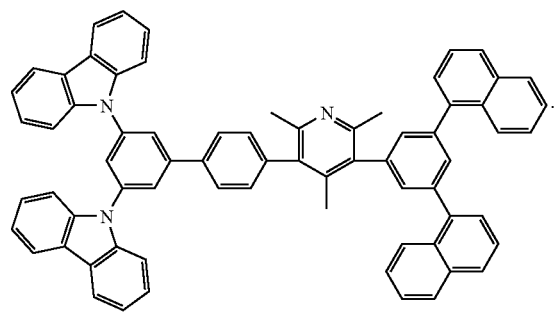

The compound represented by Chemical Formula 1 may be selected from compounds represented by the following Chemical Formulae 1-46 to 1-53:
[Chemical Formula 1-46]
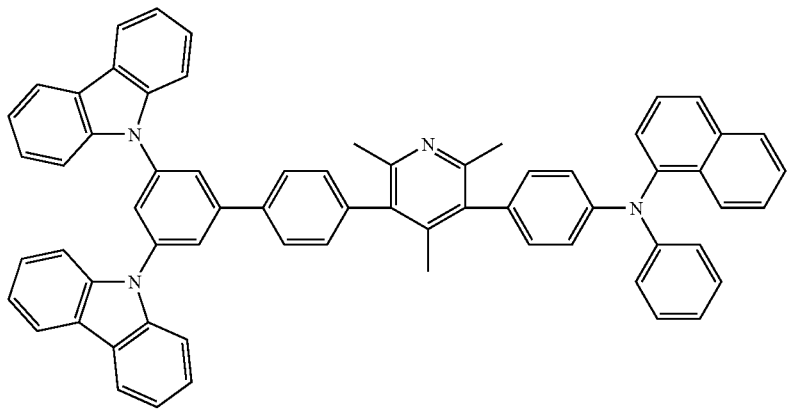
[Chemical Formula 1-47]
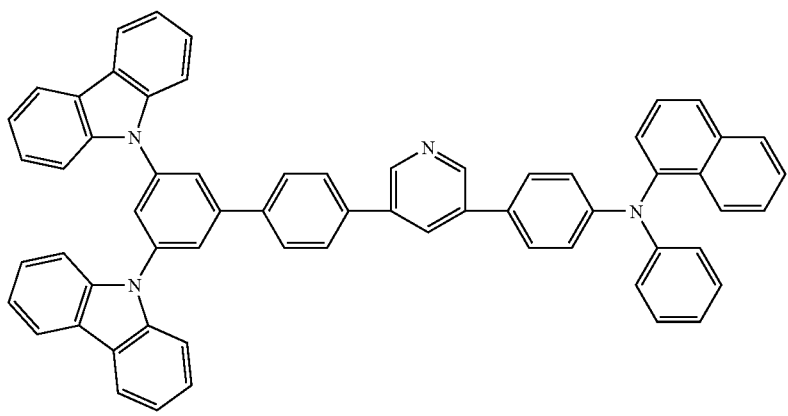
[Chemical Formula 1-48]
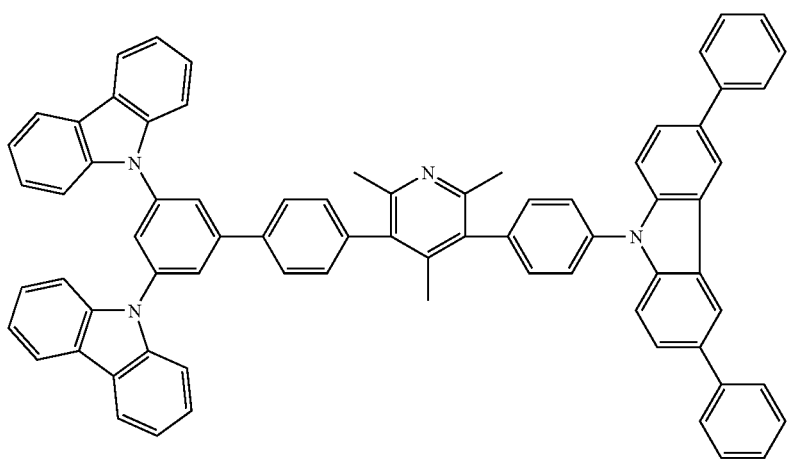

[Chemical Formula 1-49]

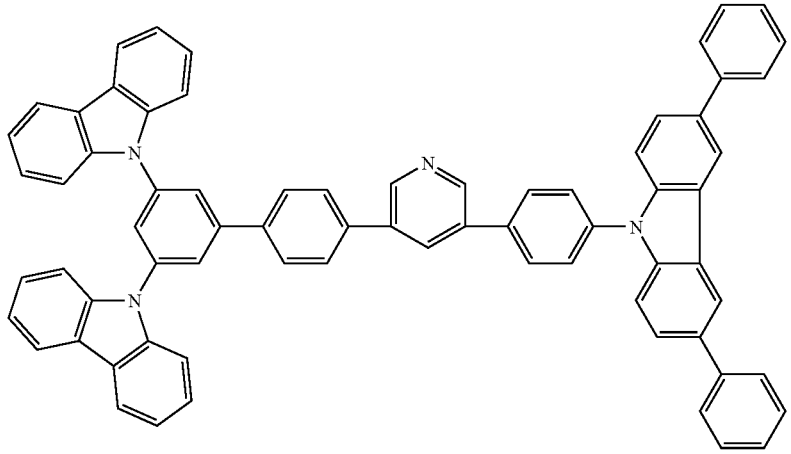

[Chemical Formula 1-50]

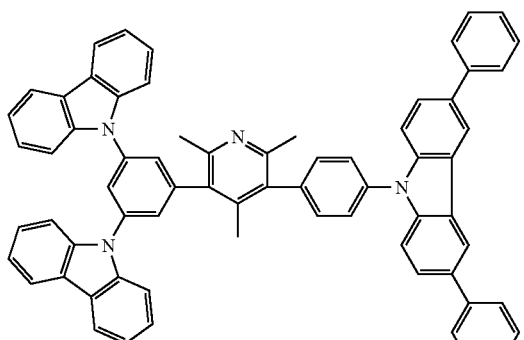

[Chemical Formula 1-51]

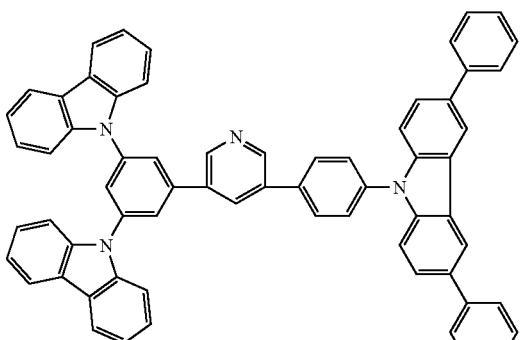

[Chemical Formula 1-52]

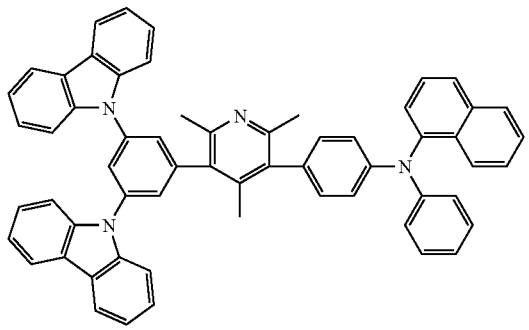

[Chemical Formula 1-53]

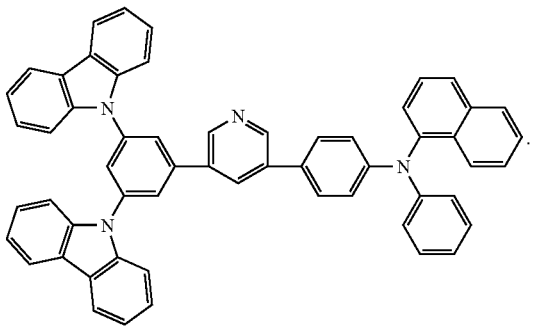

At least one of the above and other features and advantages may also be realized by providing an organic photoelectric device, including an anode, a cathode, and an organic layer disposed between the anode and cathode. The organic layer may include the material according to an embodiment.

The organic layer may be an emission layer.

The emission layer may include a phosphorescent or fluorescent host that includes the compound represented by Chemical Formula 1, and a phosphorescent or fluorescent dopant selected from the group of red, green, blue, and white light-emitting dopants.

The organic layer may be selected from the group of an emission layer, a hole transport layer (HTL), a hole injection layer (HIL), an electron transport layer (ETL), an electron injection layer (EIL), and combinations thereof.

BRIEF DESCRIPTION OF THE DRAWINGS

The above and other features and advantages will become more apparent to those of skill in the art by describing in detail example embodiments with reference to the attached drawings, in which.

Figure 1:
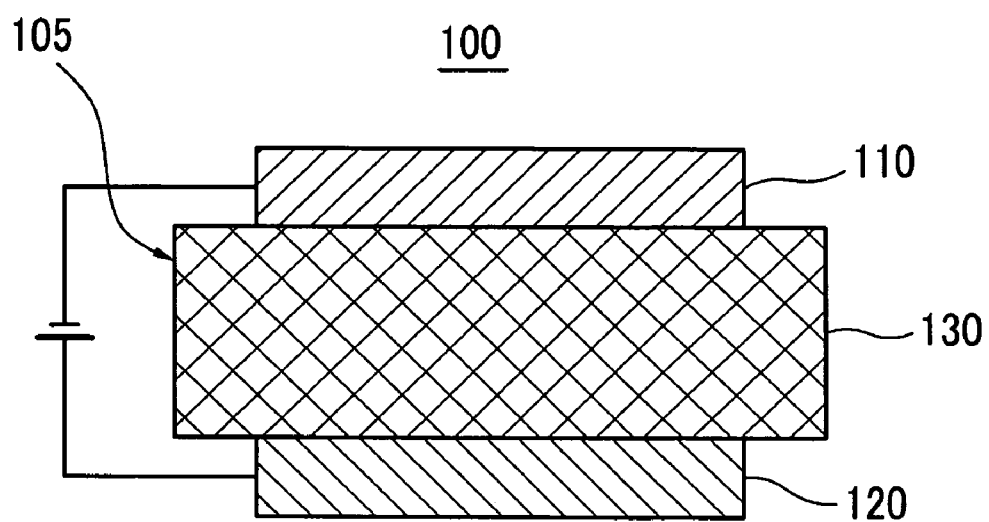
FIGS. 1 to 5 illustrate cross-sectional views of organic photoelectric devices including organic compounds according to various embodiments.

<Description of Reference Numerals in the Drawings>

| | |
|---|---|
| 100: organic photoelectric device | 110: cathode |
| 120: anode | 105: organic thin layer |
| 130: emission layer | 140: hole transport layer (HTL) |

| | |
|---|---|
| 150: electron transport layer (ETL) | 160: electron injection layer (EIL) |
| 170: hole injection layer (HIL) | |

DETAILED DESCRIPTION

Korean Patent Application No. 10-2007-0110984, filed on Nov. 1, 2007, in the Korean Intellectual Property Office, and entitled: "Material for Organic Photoelectric Device, and Organic Photoelectric Device Thereby," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the expressions "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" includes the following meanings: A alone; B alone; C alone; both A and B together; both A and C together; both B and C together; and all three of A, B, and C together. Further, these expressions are open-ended, unless expressly designated to the contrary by their combination with the term "consisting of." For example, the expression "at least one of A, B, and C" may also include an $n^{th}$ member, where n is greater than 3, whereas the expression "at least one selected from the group consisting of A, B, and C" does not.

As used herein, the expression "or" is not an "exclusive or" unless it is used in conjunction with the term "either." For example, the expression "A, B, or C" includes A alone; B alone; C alone; both A and B together; both A and C together; both B and C together; and all three of A, B, and C together, whereas the expression "either A, B, or C" means one of A alone, B alone, and C alone, and does not mean any of both A and B together; both A and C together; both B and C together; and all three of A, B, and C together.

As used herein, the terms "a" and "an" are open terms that may be used in conjunction with singular items or with plural items. For example, the term "a dopant" may represent a single compound, e.g., $Ir(Piq)_2(acac)$, or multiple compounds in combination, e.g., $Ir(Piq)_2(acac)$ mixed with PtOEP.

Herein, Markush groups, if any, are identified by the closed language "selected from the group consisting of."

Embodiments relate to a material for an organic photoelectric device, and an organic photoelectric device using the same. The material may provide thermal stability, have good hole and electron transporting properties, and be suitable for an organic photoelectric device having high luminous efficiency at a low driving voltage.

The material may be used alone, may be used as a host material in combination with a dopant, etc. The material may include a symmetric or asymmetric compound represented by the following Chemical Formula 1. The compound represented by Chemical Formula 1 may be used with other compounds represented by Chemical Formula 1 in a mixture of respective compounds of Chemical Formula 1, each of which is different from the others. The material represented by the following Chemical Formula 1 may be a bipolar organic compound including both a hole transporting unit and an electron transporting unit.

[Chemical Formula 1]

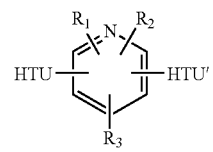

In Chemical Formula 1, HTU and HTU' are independently hole transporting units.

In Chemical Formula 1, $R_1$ to $R_3$ (i.e., $R_1$, $R_2$, and $R_3$) are independently a substituent selected from the group of hydrogen, a substituted or unsubstituted C6 to C30 aryl, a substituted or unsubstituted C2 to C30 heteroaryl, and a substituted or unsubstituted C1 to C30 alkyl.

As used herein, when a specific definition is not otherwise provided, the substituted aryl, substituted arylene, substituted alkyl, substituted alkylene, substituted heteroaryl, or substituted heteroarylene may respectively refer to an aryl, an arylene, an alkyl, an alkylene, a heteroaryl, or a heteroarylene substituted with a C1 to C30 alkyl, a halogen, a C1 to C30 haloalkyl, a C6 to C30 aryl, or a C2 to C30 heteroaryl.

As used herein, when a specific definition is not otherwise provided, the heteroaryl or heteroarylene may respectively refer to an aryl and an arylene including 1 to 3 heteroatoms selected from the group of nitrogen (N), oxygen (O), sulfur (S), and phosphorus (P), and the remainder being carbon.

In the bipolar organic compound of Chemical Formula 1, pyridine ($C_6H_5N$) functions as an electron transporting unit. The HTU and HTU' independently represent hole transporting units and are the same or different from each other.

In an embodiment, the compound represented by Chemical Formula 1 may be a bipolar organic compound represented by the following Chemical Formula 2.

[Chemical Formula 2]

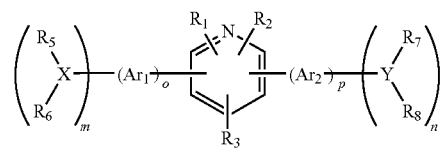

In Chemical Formula 2, X and Y are independently selected from the group of nitrogen, sulfur, and oxygen.

In Chemical Formula 2, $Ar_1$ and $Ar_2$ are independently selected from the group of a substituted or unsubstituted C6 to C30 aryl or arylene, a substituted or unsubstituted C1 to C30 alkyl or alkylene, and a substituted or unsubstituted C2 to C30 heteroaryl or heteroarylene.

In Chemical Formula 2, $R_1$ to $R_3$ are independently selected from the group of hydrogen, a substituted or unsubstituted C6 to C30 aryl, a substituted or unsubstituted C2 to C30 heteroaryl, and a substituted or unsubstituted C1 to C30 alkyl.

In Chemical Formula 2, $R_5$ to $R_8$ (i.e., $R_5$, $R_6$, $R_7$, and $R_8$) are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene.

In Chemical Formula 2, $R_5$ and $R_6$ are independently separate substituents or are joined together to form a ring, and $R_7$ and $R_8$ are independently separate substituents or are joined together to form a ring. In an implementation, $R_5$ and $R_6$ may be fused together to form a cyclic structure, and/or $R_7$ and $R_8$ may be fused together to form a cyclic structure.

In Chemical Formula 2, when X is sulfur or oxygen, at least one of $R_5$ or $R_6$ is a lone pair electron, and when Y is sulfur or oxygen, at least one of $R_7$ or $R_8$ is a lone pair electron.

In Chemical Formula 2, m and n are integers ranging from 0 to 3, and m+n is an integer ranging from 1 to 6.

In Chemical Formula 2, o and p are integers ranging from 0 to 2.

In Chemical Formula 2, substituents linked to the side chains of $Ar_1$ and $Ar_2$ may function as hole transporting units.

In an embodiment, the compound represented by Chemical Formula 1 may be a bipolar organic compound represented by the following Chemical Formula 3.

[Chemical Formula 3]

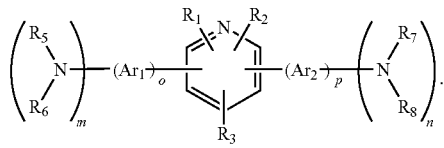

In Chemical Formula 3, $Ar_1$ and $Ar_2$ are independently selected from the group of a substituted or unsubstituted C6 to C30 aryl or arylene, a substituted or unsubstituted C1 to C30 alkyl or alkylene, and a substituted or unsubstituted C2 to C30 heteroaryl or heteroarylene.

In Chemical Formula 3, $R_1$, to $R_3$ are independently a substituent selected from the group of hydrogen, a substituted or unsubstituted C6 to C30 aryl, a substituted or unsubstituted C2 to C30 heteroaryl, and a substituted or unsubstituted C1 to C30 alkyl.

In Chemical Formula 3, $R_5$ to $R_8$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene.

In Chemical Formula 3, $R_5$ and $R_6$ are independently separate substituents or are joined together to form a ring, and $R_7$ and $R_8$ are independently separate substituents or are joined together to form a ring. In an implementation, $R_5$ and $R_6$ may be fused together to form a cyclic structure, and/or $R_7$ and $R_8$ may be fused together to form a cyclic structure.

In Chemical Formula 3, m and n are integers ranging from 0 to 3, and m+n is an integer ranging from 1 to 6.

In Chemical Formula 3, o and p are integers ranging from 0 to 2.

The substituents linked to the side chains of $Ar_1$ and $Ar_2$ functioning as a hole transporting unit in Chemical Formula 3 are independently selected from the group of a substituent of the following Formula 4 and a substituent of the following Chemical Formula 5.

[Chemical Formula 4]

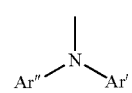

In Chemical Formula 4, Ar' and Ar" are independently selected from the group of phenyl, naphthyl, anthryl, phenanthryl, naphthacenyl, pyrenyl, biphenylyl, terphenylyl, tolyl, pyrrol, pyrazinyl, pyrimidyl, pyridazinyl, pyridinyl, indolyl, puryl, benzofuranyl, quinolyl, quinoxalinyl, phenanthridinyl, acridinyl, phenanthrolinyl, phenazinyl, phenothiazinyl, phenoxazinyl, oxazolyl, oxadiazolyl, and thienyl.

[Chemical Formula 5]

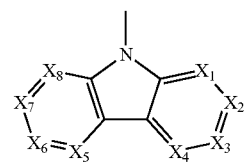

In Chemical Formula 5, $X_1$ to $X_8$ are independently selected from the group of CR' and N.

In Chemical Formula 5, R' is selected from the group of a substituent selected from the group of hydrogen, a substituted or unsubstituted C6 to C30 aryl, a substituted or unsubstituted C2 to C30 heteroaryl, and a substituted or unsubstituted C1 to C30 alkyl.

In an embodiment, the compound represented by Chemical Formula 1 may be a bipolar organic compound represented by the following Chemical Formula 6.

[Chemical Formula 6]

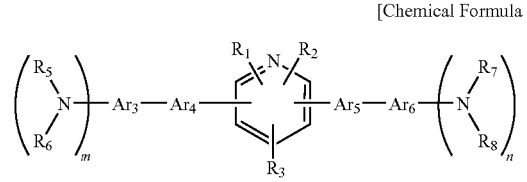

In Chemical Formula 6, $Ar_3$ and $Ar_6$ are independently selected from the group of a substituted or unsubstituted C6 to, C30 aryl or arylene, a substituted or unsubstituted C1 to C30 alkyl or alkylene, and a substituted or unsubstituted C2 to C30 heteroaryl or heteroarylene.

In Chemical Formula 6, $Ar_4$ and $Ar_5$ are independently selected from the group of a substituted or unsubstituted C6 to C30 arylene, a substituted or unsubstituted C1 to C30 alkylene, and a substituted or unsubstituted C2 to C30 heteroarylene.

In Chemical Formula 6, $R_1$ to $R_3$ are independently a substituent selected from the group of hydrogen, a substituted or unsubstituted C6 to C30 aryl, a substituted or unsubstituted C2 to C30 heteroaryl, and a substituted or unsubstituted C1 to C30 alkyl.

In Chemical Formula 6, $R_5$ to $R_8$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene.

In Chemical Formula 6, $R_5$ and $R_6$ are independently separate substituents or are joined together to form a ring, and $R_7$ and $R_8$ are independently separate substituents or are joined together to form a ring. In an implementation, $R_5$ and $R_6$ may be fused together to form a cyclic structure, and/or $R_7$ and $R_8$ may be fused together to form a cyclic structure.

In Chemical Formula 6, m and n are integers ranging from 0 to 3, and m+n is an integer ranging from 1 to 6.

In an embodiment, the compound represented by Chemical Formula 1 may be a bipolar organic compound represented by the following Chemical Formula 7.

[Chemical Formula 7]

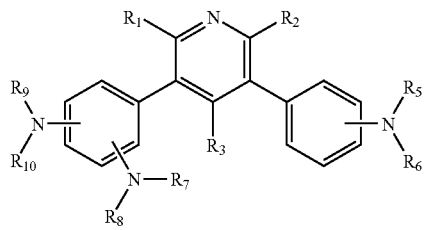

In Chemical Formula 7, $R_1$ to $R_3$ are independently a substituent selected from the group of hydrogen, a substituted or unsubstituted C6 to C30 aryl, a substituted or unsubstituted C2 to C30 heteroaryl, and a substituted or unsubstituted C1 to C30 alkyl.

In Chemical Formula 7, $R_5$ to $R_{10}$ are independently selected from the group of hydrogen, a substituted or unsubstituted C6 to C30 aryl or arylene, a substituted or unsubstituted C2 to C30 heteroaryl or heteroarylene, and a substituted or unsubstituted C1 to C30 alkyl or alkylene.

In Chemical Formula 7, $R_5$ and $R_6$ are independently separate substituents or are joined together to form a ring, $R_7$ and $R_8$ are independently separate substituents or are joined together to form a ring, and $R_9$ and $R_{10}$ are independently separate substituents or are joined together to form a ring. In an implementation, $R_5$ and $R_6$ may be fused together to form a cyclic structure, and/or $R_7$ and $R_8$ may be fused together to form a cyclic structure, and/or $R_9$ and $R_{10}$ may be fused together to form a cyclic structure.

The material for an organic photoelectric device according to an embodiment of the present invention has a glass transition temperature (Tg) of 120° C. or more, and a thermal decomposition temperature (Td) of 400° C. or more. Therefore, the material for an organic photoelectric device may have a high degree of thermal stability, sufficient for an organic photoelectric device.

In embodiments, compounds represented by Chemical Formulae 1, 2, 3, 6, and 7 may be exemplified by bipolar organic compounds represented by the following Chemical Formulae 1-1 to 1-53.

[Chemical Formula 1-1]

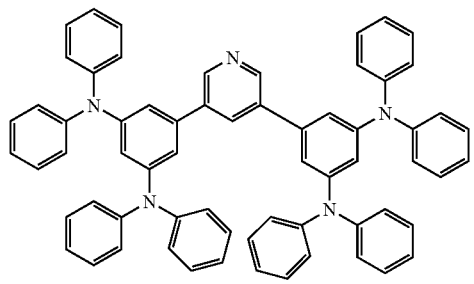

[Chemical Formula 1-2]

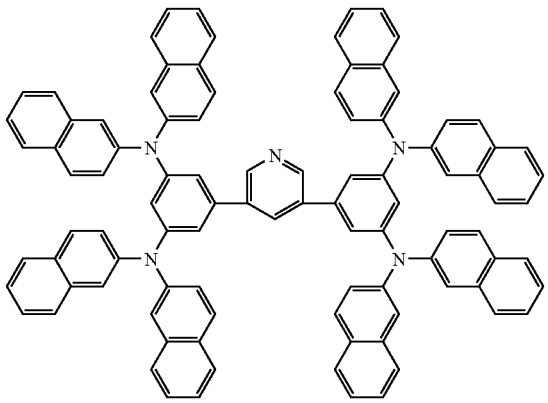

[Chemical Formula 1-3]

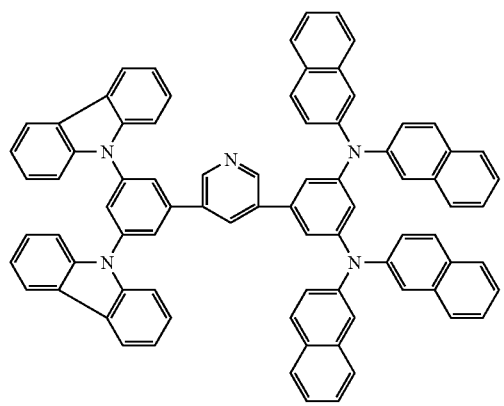

[Chemical Formula 1-4]

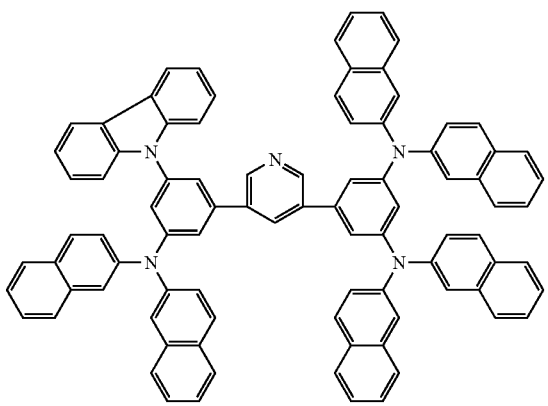

[Chemical Formula 1-5]
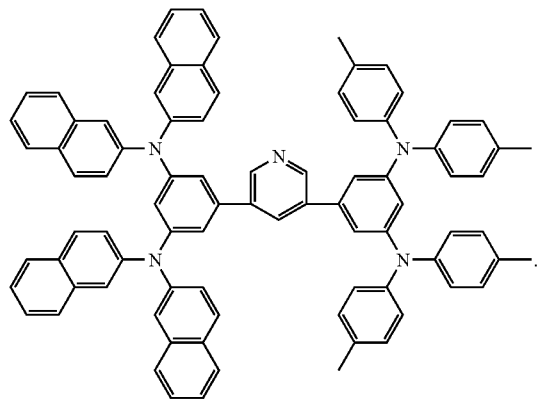
[Chemical Formula 1-6]
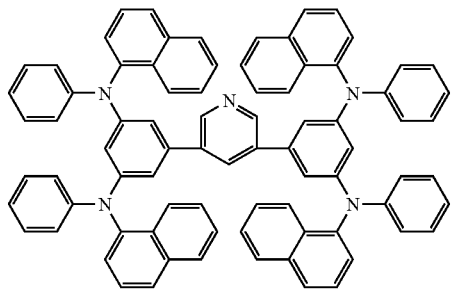
[Chemical Formula 1-7]
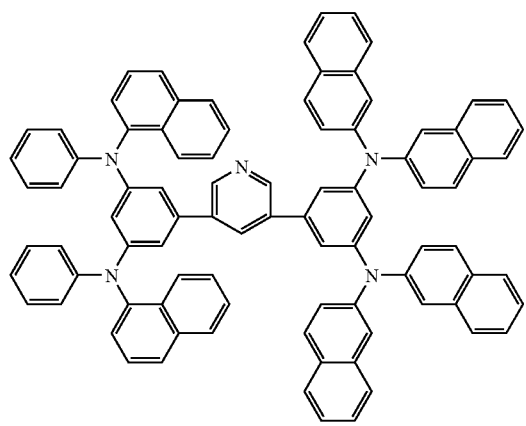
[Chemical Formula 1-8]
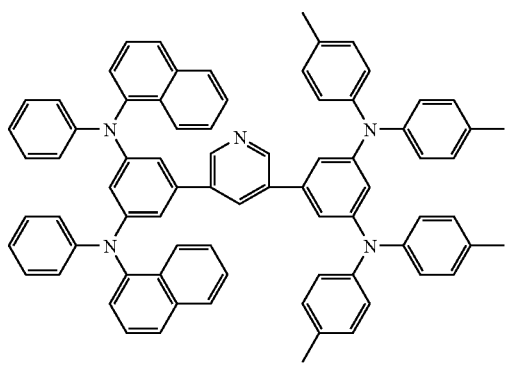
[Chemical Formula 1-9]
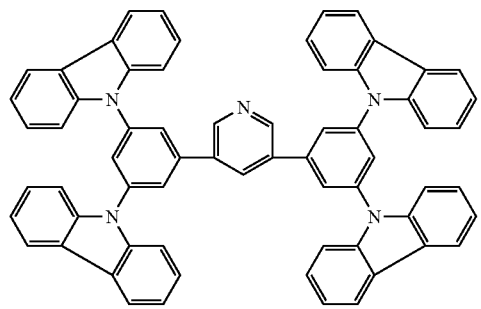
[Chemical Formula 1-10]
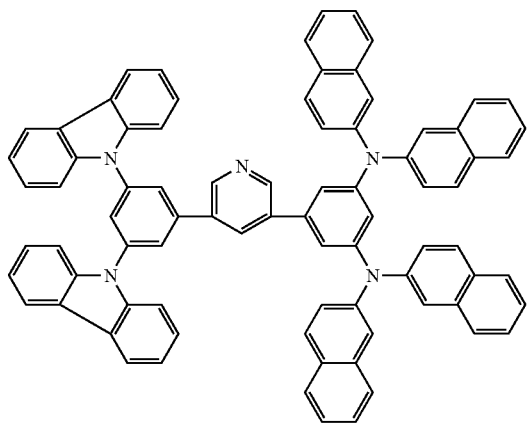

[Chemical Formula 1-11]
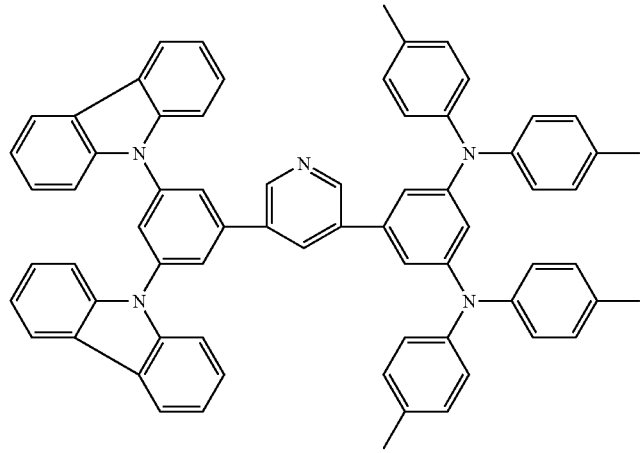
[Chemical Formula 1-12]
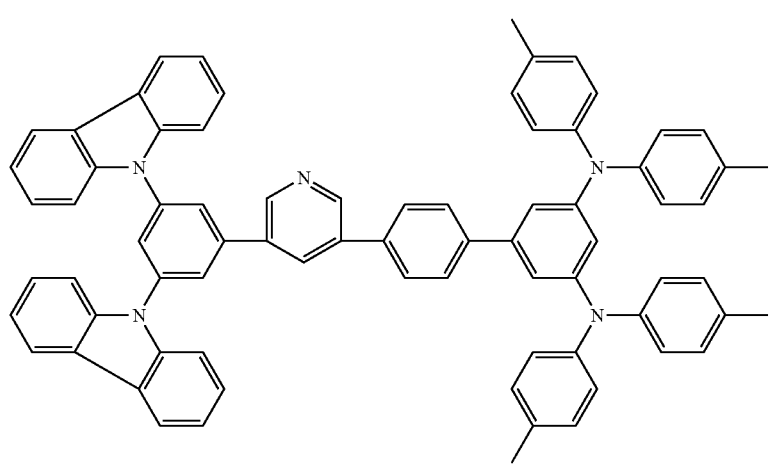
[Chemical Formula 1-13]
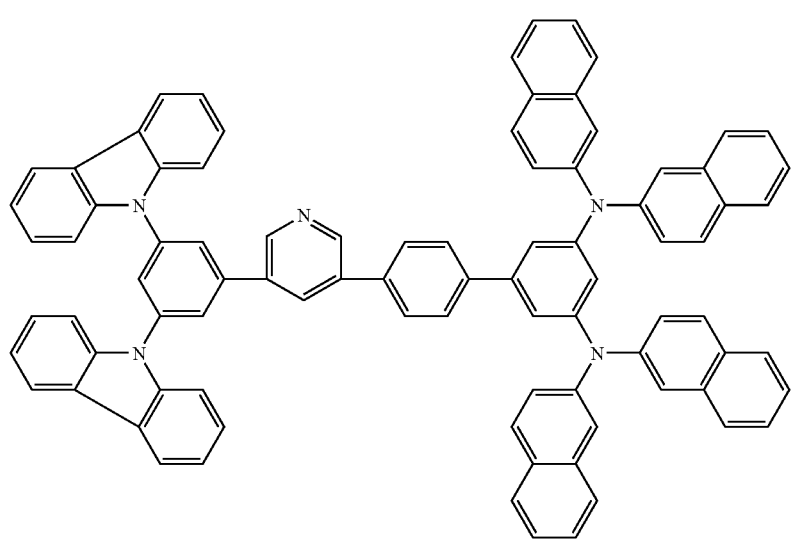

[Chemical Formula 1-14]
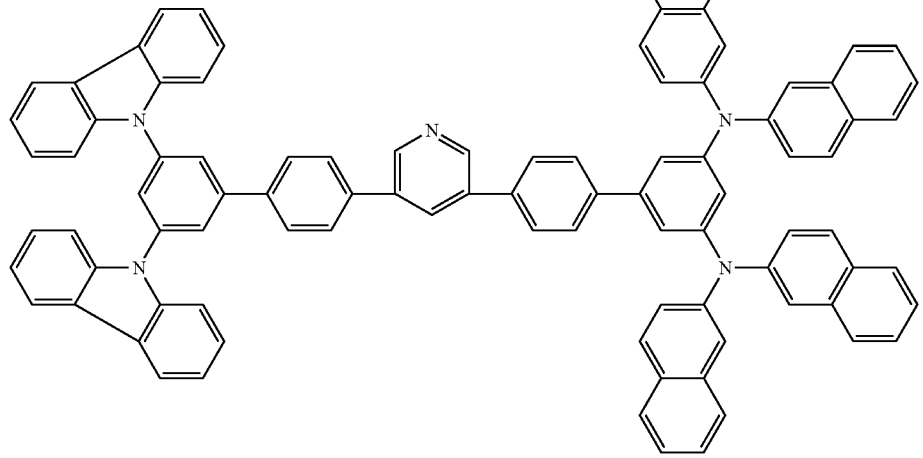
[Chemical Formula 1-15]
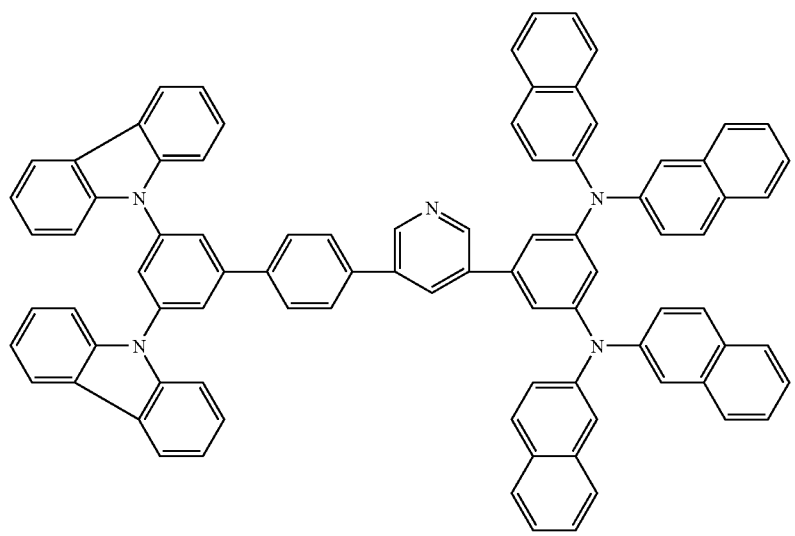
[Chemical Formula 1-16]
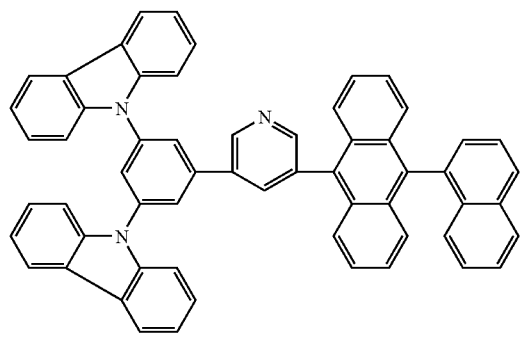

-continued
[Chemical Formula 1-17]
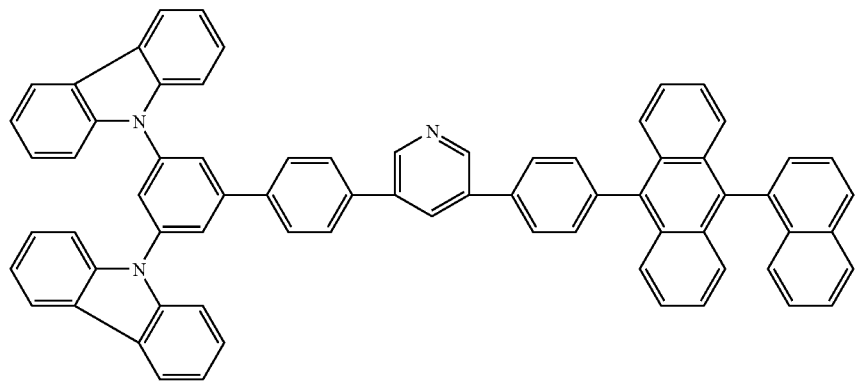
[Chemical Formula 1-18]
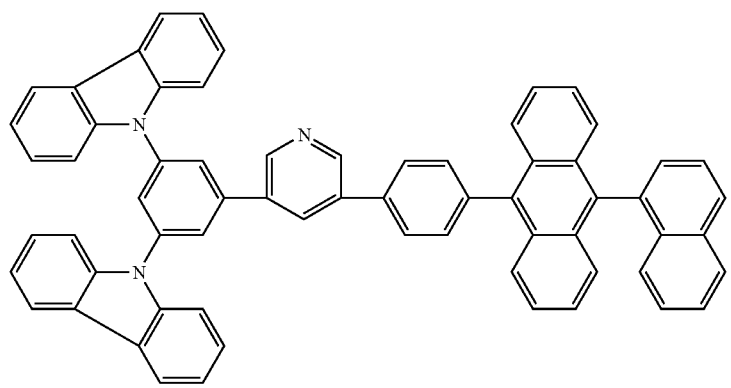
[Chemical Formula 1-19]
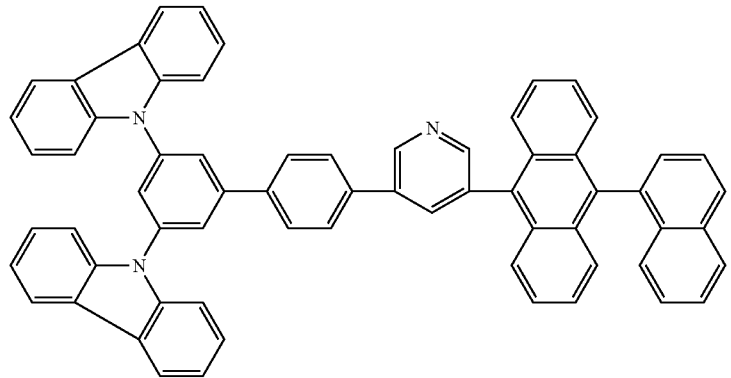
[Chemical Formula 1-20]
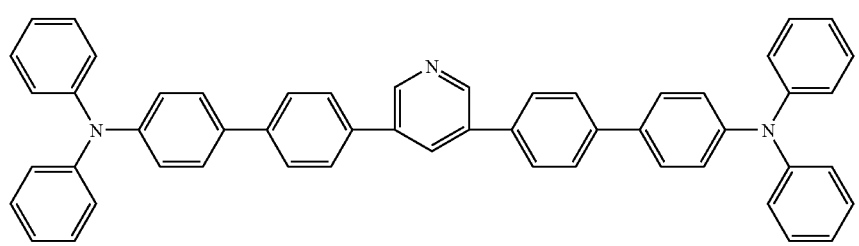
[Chemical Formula 1-21]
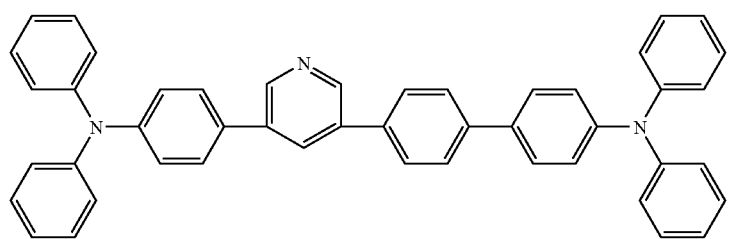

[Chemical Formula 1-22]
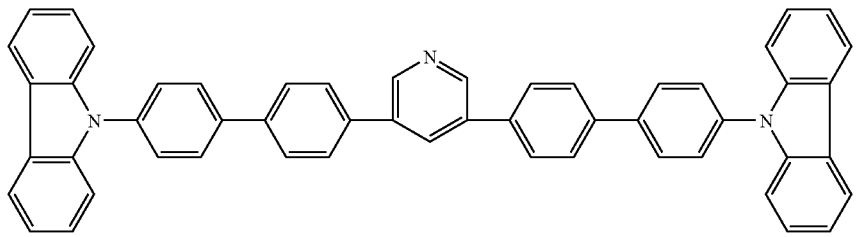
[Chemical Formula 1-23] [Chemical Formula 1-24]
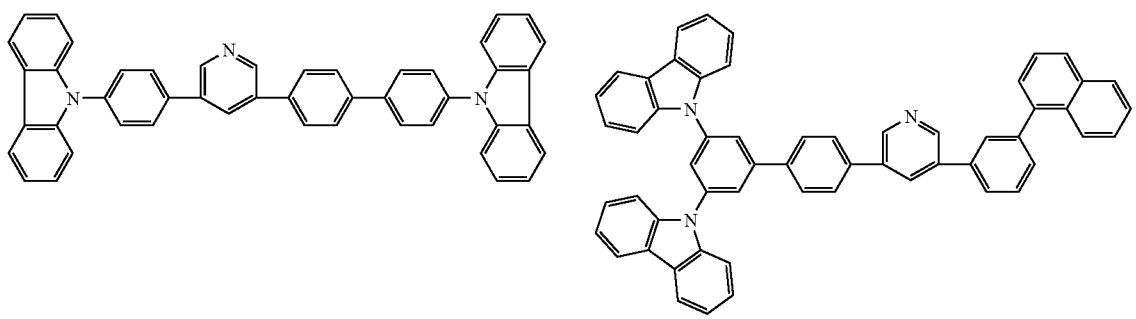
[Chemical Formula 1-25] [Chemical Formula 1-26]
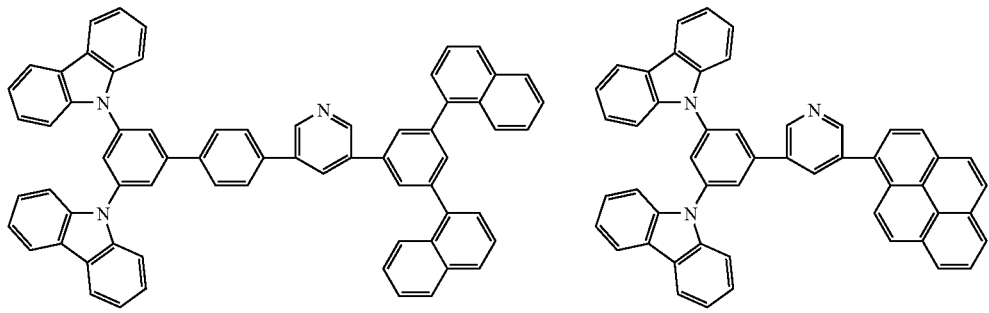
[Chemical Formula 1-27]
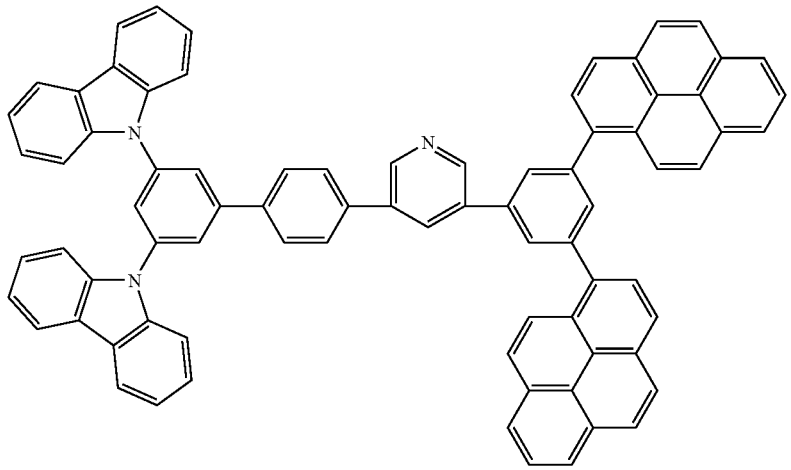

[Chemical Formula 1-28]
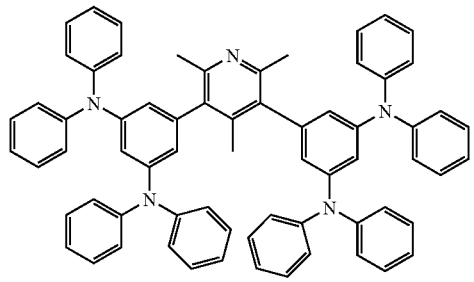
[Chemical Formula 1-29]
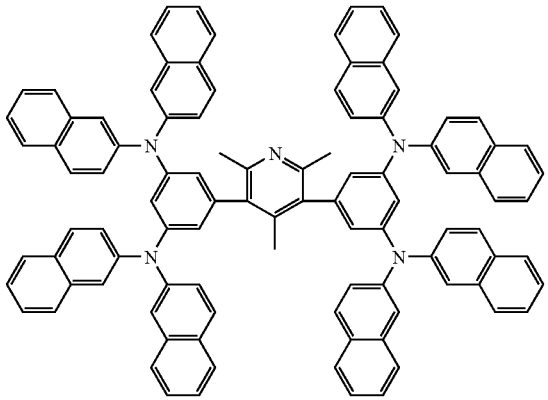
[Chemical Formula 1-30]
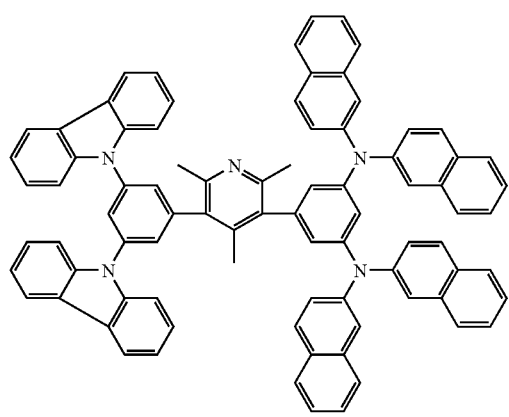
[Chemical Formula 1-31]
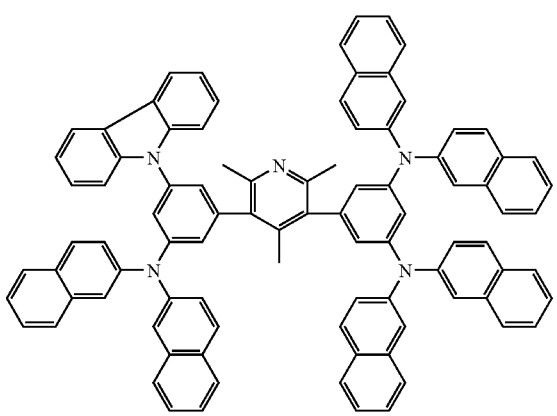
[Chemical Formula 1-32]
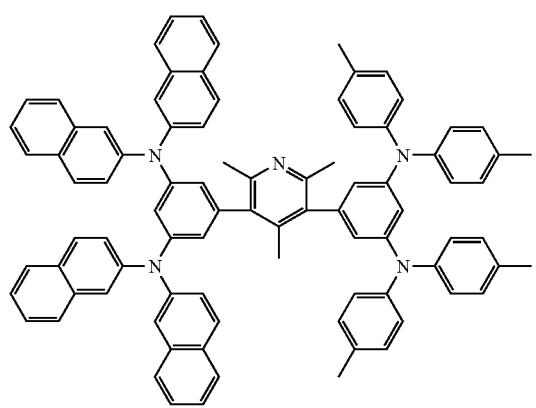
[Chemical Formula 1-33]
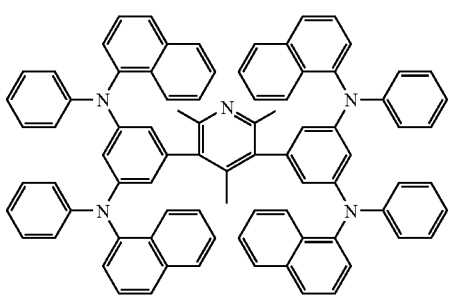

-continued
[Chemical Formula I-34]
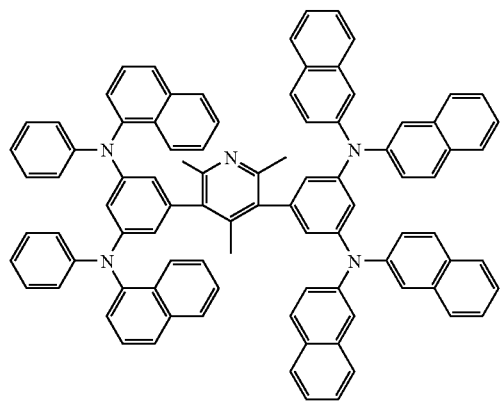
[Chemical Formula I-35]
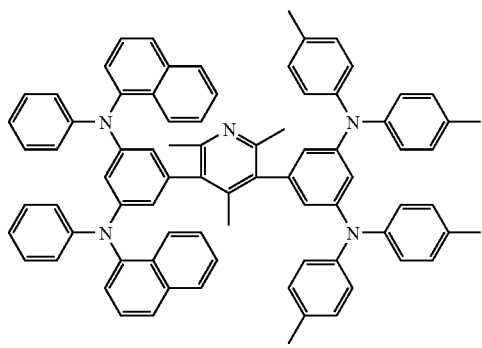
[Chemical Formula I-36]
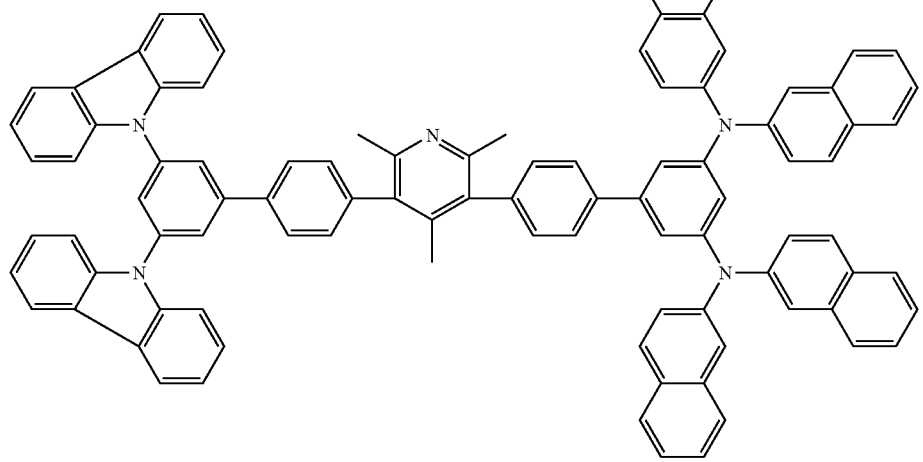
[Chemical Formula I-37]
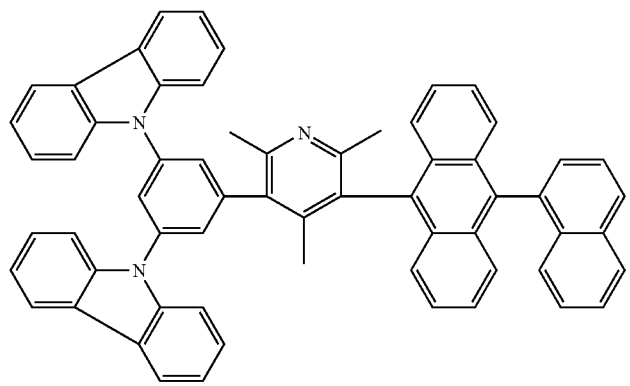

[Chemical Formula 1-38]
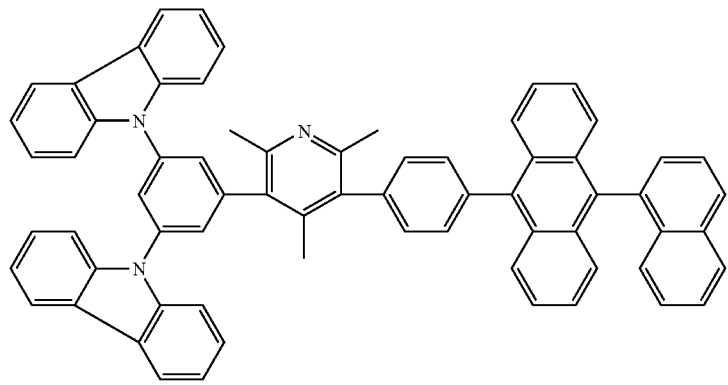
[Chemical Formula 1-39]
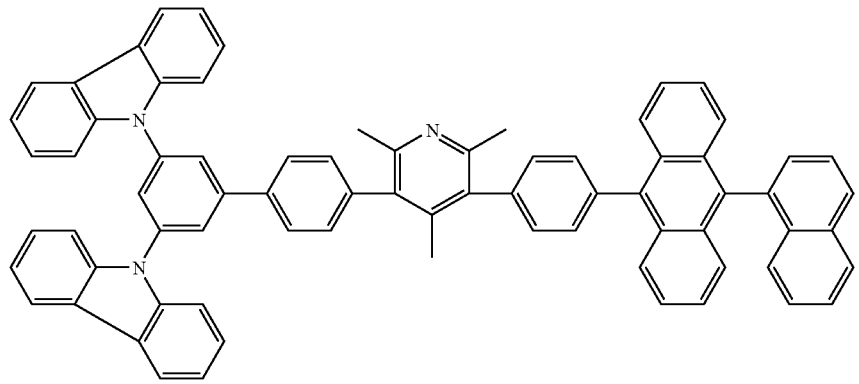
[Chemical Formula 1-40]
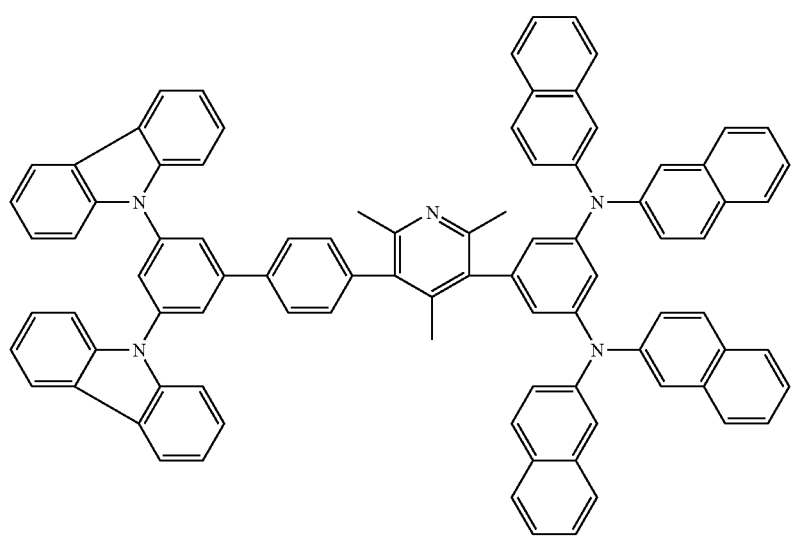

[Chemical Formula 1-41]
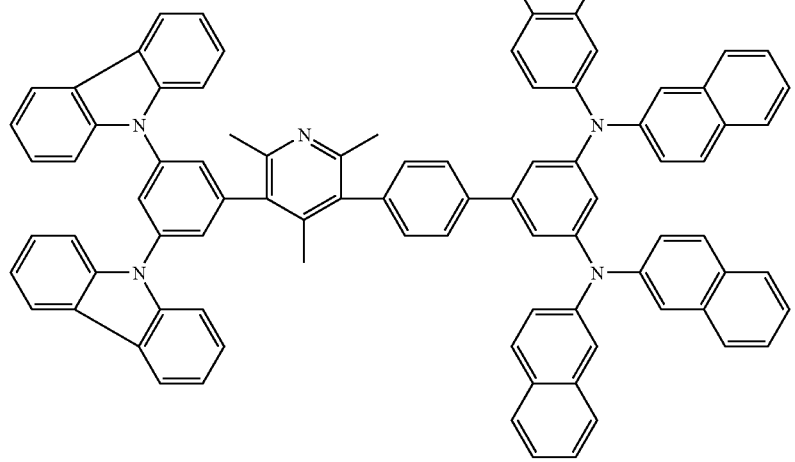
[Chemical Formula 1-42]
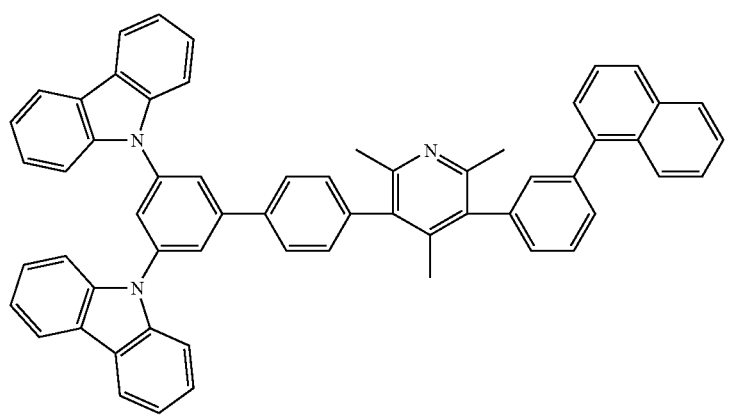
[Chemical Formula 1-43]
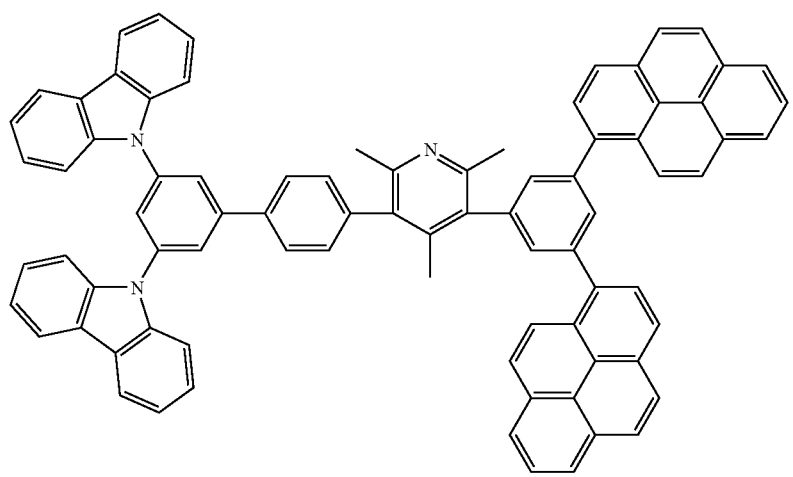

-continued
[Chemical Formula 1-44]
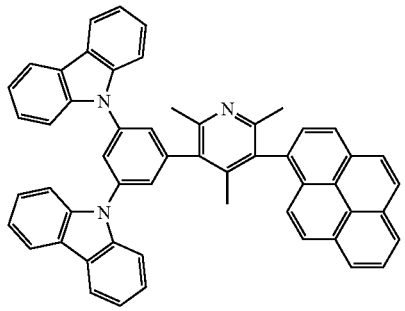
[Chemical Formula 1-45]
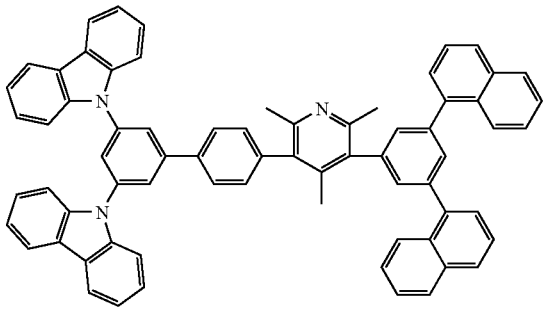
[Chemical Formula 1-46]
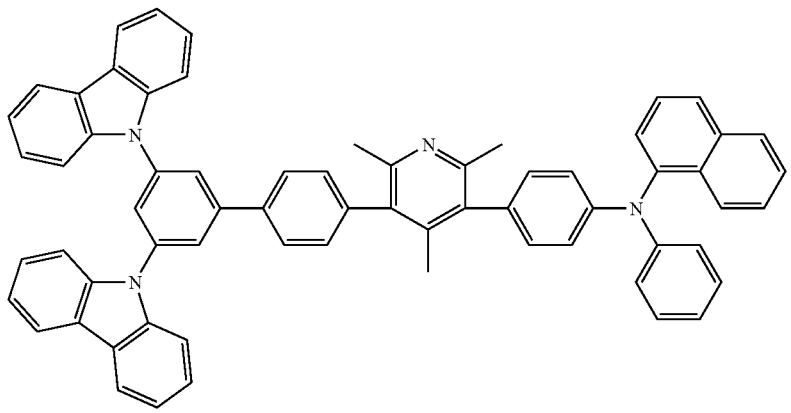
[Chemical Formula 1-47]
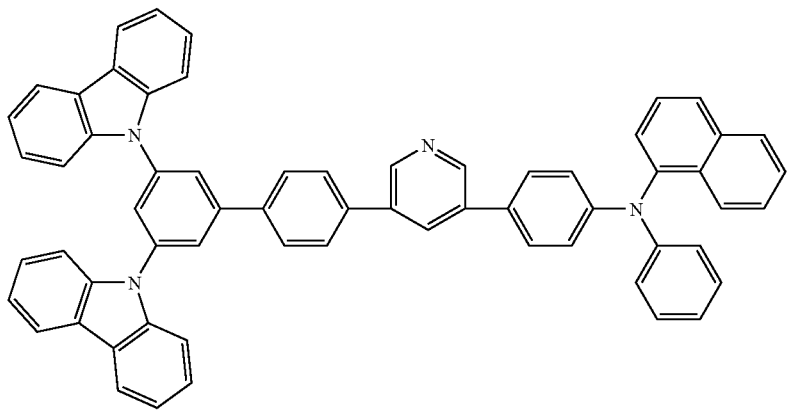
[Chemical Formula 1-48]
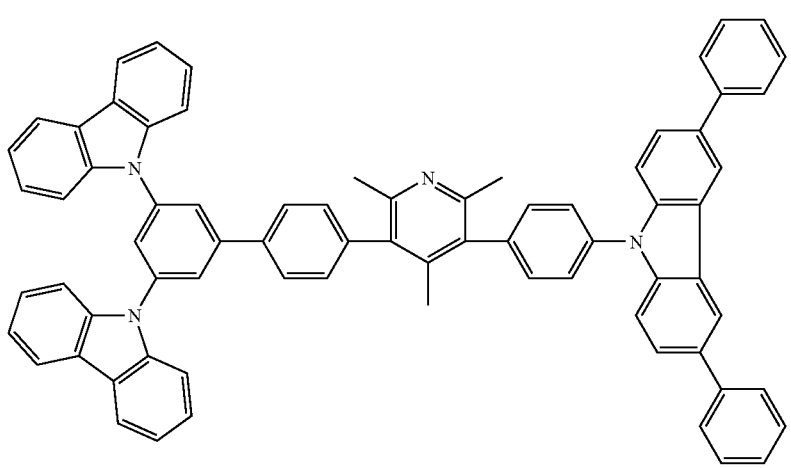

[Chemical Formula 1-49]
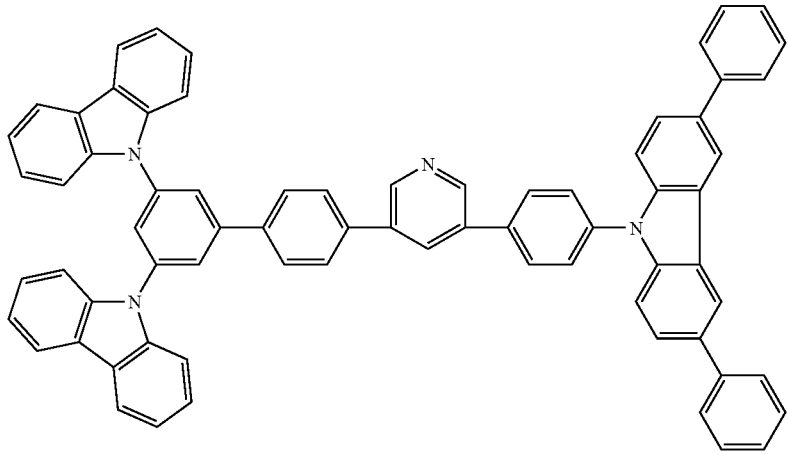
[Chemical Formula 1-50]
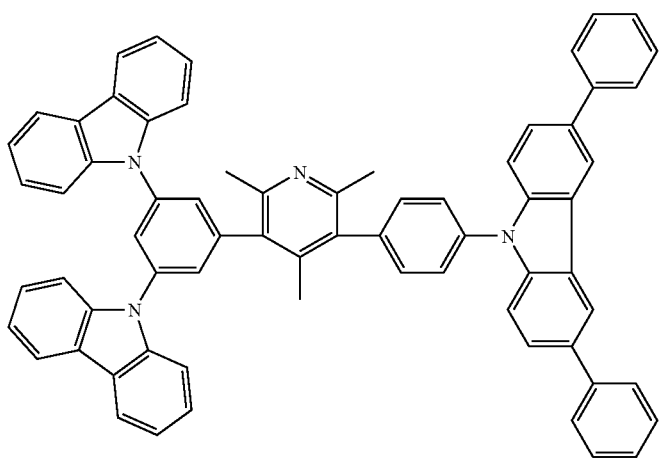
[Chemical Formula 1-51] [Chemical Formula 1-52]
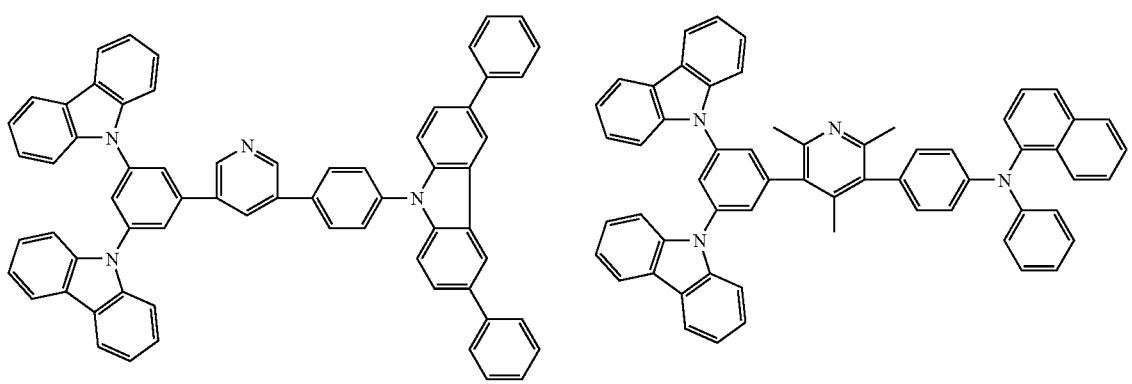

[Chemical Formula 1-53]

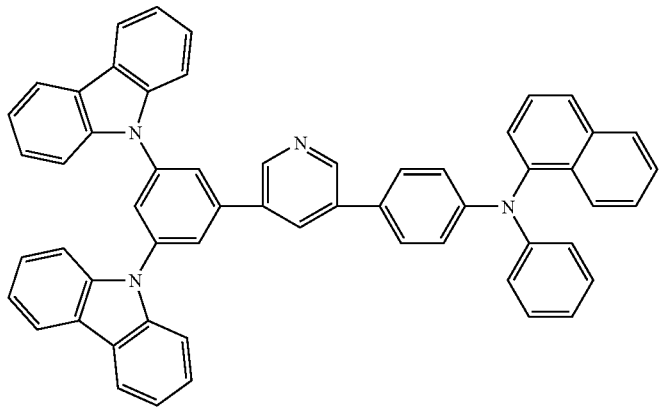

The compound represented by Chemical Formula 1 may be included in at least one layer selected from the group of an emission layer, an electron transport layer (ETL), an electron injection layer (EIL), a hole transport layer (HTL), a hole injection layer (HIL), a hole blocking layer, and combinations thereof.

The compound represented by Chemical Formula 1 may be used alone in an electron transport layer (ETL), an electron injection layer (EIL), a hole transport layer (HTL), a hole injection layer (HIL), or a hole blocking layer. The compound represented by Chemical Formula 1 may be used in the emission layer. In an implementation, the compound represented by Chemical Formula 1 may be used in the emission layer as a host material that is capable of binding with a dopant.

The dopant may be a compound having a high emission property by itself. The dopant may be added to a host in a minor amount. The dopant may also be called a guest. Thus, the dopant may be a material that is doped to the host material to emit light. The dopant may include a metal complex that emits light due to multiplet excitation into a triplet or higher state.

When the organic compounds represented by Chemical Formulae 1 to 5 are used for a light emitting host material, all red (R), green (G), and blue (B) colors and white (W) fluorescent or phosphorescent dopant materials may be suitable for a dopant. According to one embodiment, the dopant includes a phosphorescent dopant material. The material may have high light emitting quantum efficiency, may be rarely agglomerated, and may be distributed uniformly in the host material.

The phosphorescent dopant may be an organic metal compound including one or more of the following elements: Ir, Pt, Os, Ti, Zr, Hf, Eu, Tb, and Tm.

The red phosphorescent dopant may include PtOEP (platinum octaethylporphin), Ir(Piq)$_2$(acac) (Piq=1-phenylisoquinoline, acac=pentane-2,4-dione), Ir(Piq)$_3$, and RD 61 from UDC; the green phosphorescent dopant may include Ir(PPy)$_3$ (PPy=2-phenylpyridine), Ir(PPy$_2$(acac), and GD48 from UDC; and the blue phosphorescent dopant may include (4,6-F$_2$PPy)$_2$Irpic (reference: Appl. Phys. Lett., 79, 2082-2084, 2001).

Another embodiment provides an organic photoelectric device that includes an organic thin layer including the above-described material between an anode and a cathode. In an embodiment, the organic photoelectric device may be an organic light emitting diode.

FIGS. 1 to 5 illustrate cross-sectional views of organic photoelectric devices including organic compounds according to various embodiments.

Referring to FIGS. 1 to 5, the respective organic photoelectric devices 100, 200, 300, 400, and 500 illustrated therein may include at least one organic thin layer 105 interposed between an anode 120 and a cathode 110. The anode 120 may include an indium tin oxide (ITO) transparent electrode. The cathode 110 may include a metal electrode such as aluminum.

Referring to FIG. 1, the organic photoelectric device 100 may include an organic thin layer 105 including only an emission layer 130.

Figure 2:
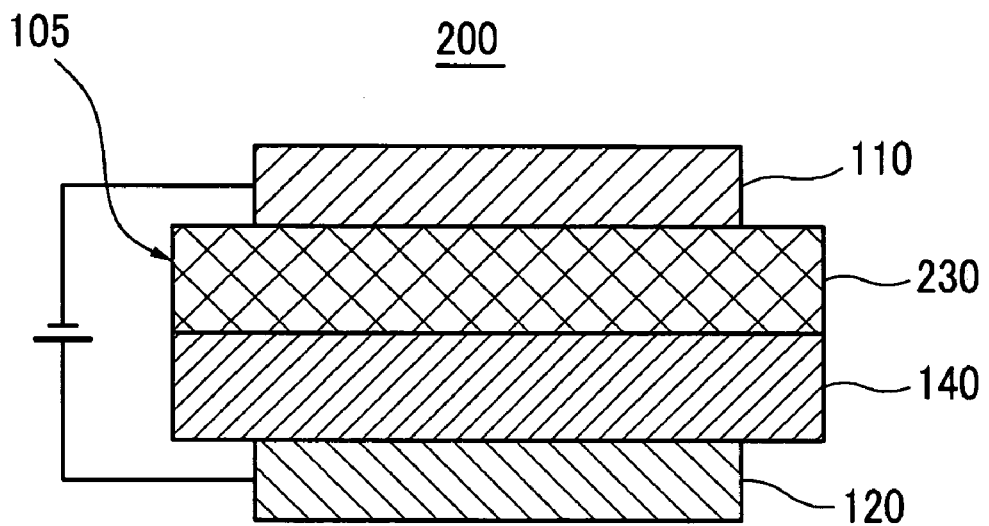

Referring to FIG. 2, a double-layered organic photoelectric device 200 may include an organic thin layer 105 including an emission layer 230 including an electron transport layer (ETL) (not shown) and a hole transport layer (HTL) 140. The hole transport layer (HTL) 140 may be a separate layer having an excellent binding property with a transparent electrode such as ITO, or an excellent hole transporting property.

Figure 3:
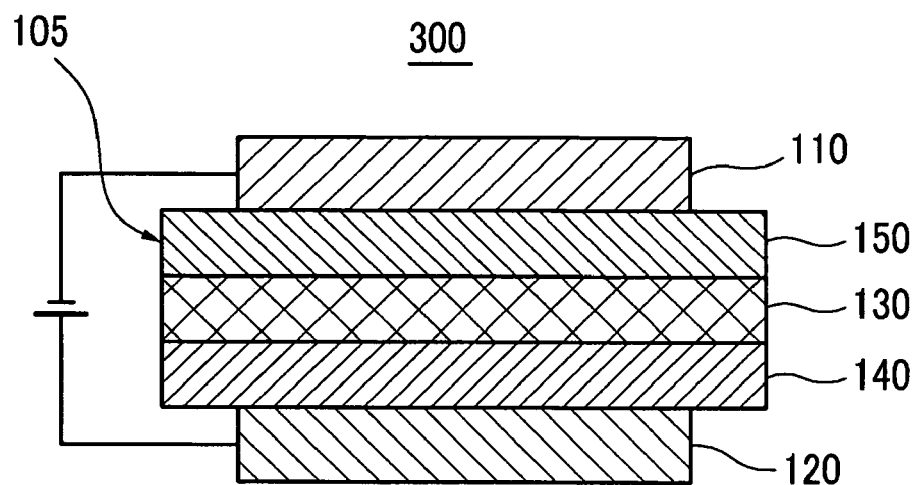

Referring to FIG. 3, a three-layered organic photoelectric device 300 may include the organic thin layer 105 including an electron transport layer (ETL) 150, an emission layer 130, and a hole transport layer (HTL) 140. The emission layer 130 may be independently provided, and layers having an excellent electron transporting property or an excellent hole transporting property may be separately stacked.

Figure 4:
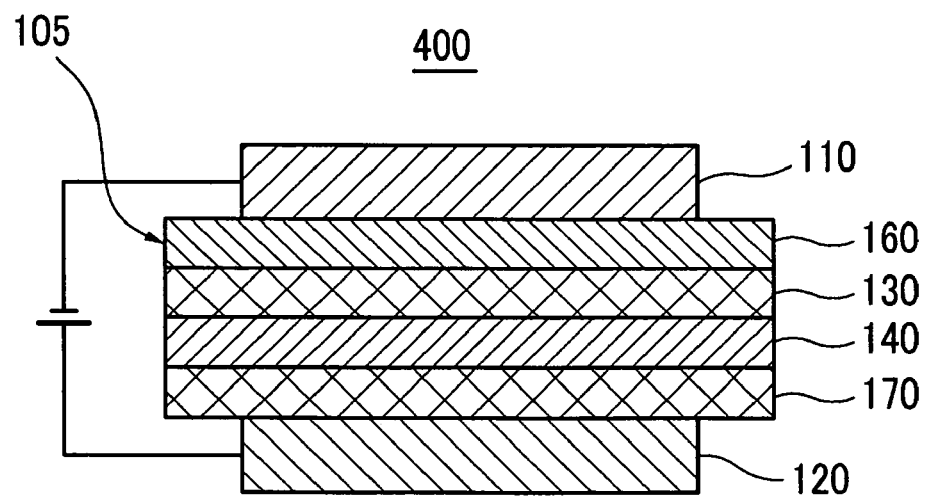

As shown in FIG. 4, a four-layered organic photoelectric device 400 may include the organic thin layer 105 including an electron injection layer (EIL) 160, an emission layer 130, a hole transport layer (HTL) 140, and a hole injection layer (HIL) 170 for binding with the cathode of ITO.

Figure 5:
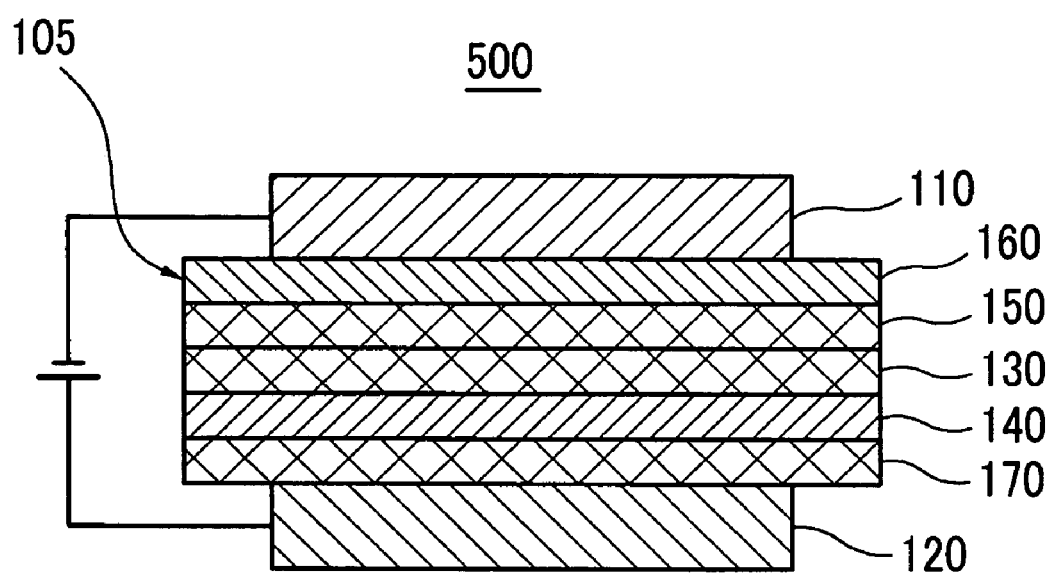

As shown in FIG. 5, a five-layered organic photoelectric device 500 may include the organic thin layer 105 including an electron transport layer (ETL) 150, an emission layer 130, a hole transport layer (HTL) 140, and a hole injection layer (HIL) 170, and may further include an electron injection layer (EIL) 160 to achieve low voltage.

In order to form the organic thin layer 105 having one to five layers, the method may follow a dry coating method such as evaporation, sputtering, plasma plating, and ion plating, or a wet coating method such as spin coating, dipping, and flow coating.

In an embodiment, at least one layer selected from the group of the emission layer, electron transport layer (ETL), electron injection layer (EIL), hole transport layer (HTL), hole injection layer (HIL), and hole blocking layer (HBL) includes the compound represented by Chemical Formula 1.

The organic thin layer may include a phosphorescent light emitting compound such as a metal complex that emits light due to the multiplet excitation into a triplet or higher state.

The following Examples and Comparative Examples are provided in order to set forth particular details of one or more embodiments. However, it will be understood that the embodiments are not limited to the particular details described.

EXAMPLE 1

Synthesis of Material for Organic Photoelectric Device

EXAMPLE 1-1

Synthesis of Compound (16)

The following compound (16) was synthesized as shown in the following Reaction Scheme 1.

[Reaction Scheme 1]

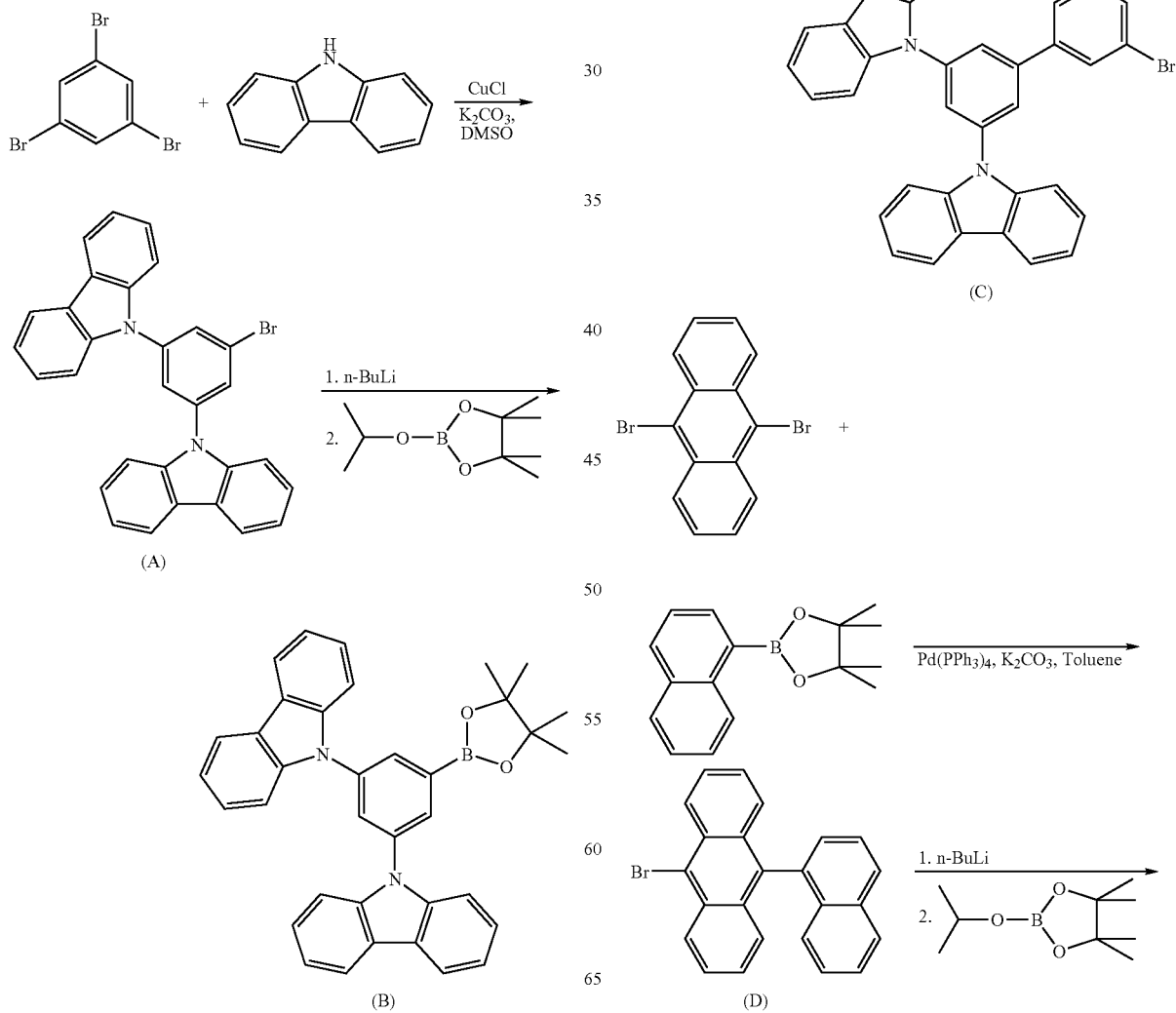

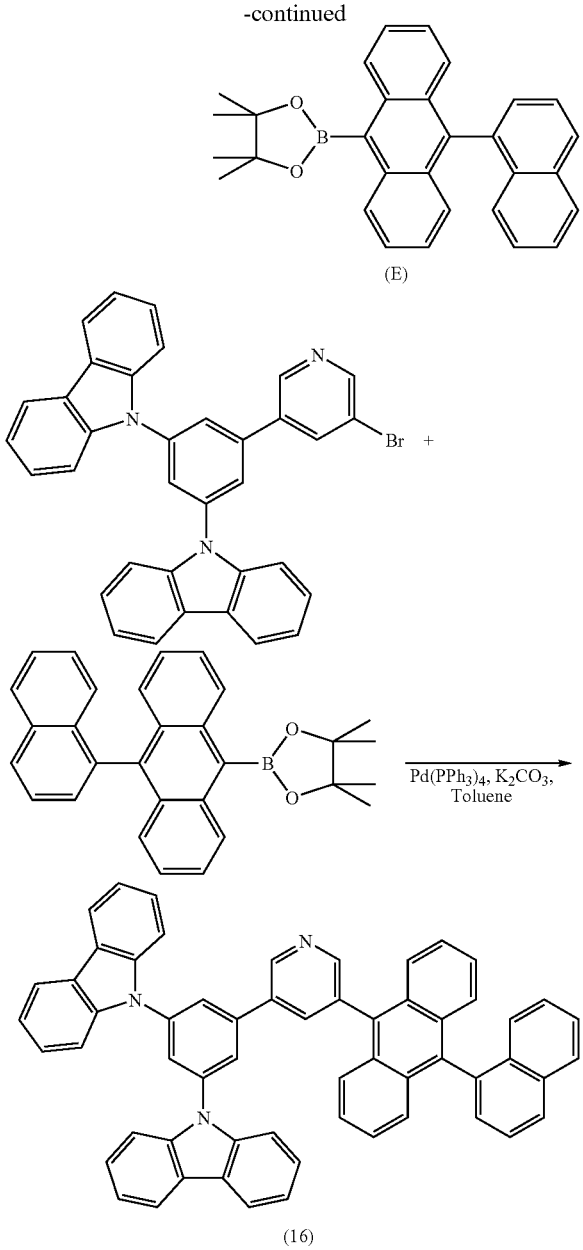

Step 1: Synthesis of Intermediate Product (A)

40.4 g (241 mmol) of carbazole, 38.0 g (121 mmol) of 1,3,5-tribromobenzene, 2.99 g (30 mmol) of cuprous chloride, and 66.7 g (483 mmol) of potassium carbonate were suspended in 171 ml of dimethylsulfoxide, and refluxed under a nitrogen atmosphere for 8 hours while heating.

The refluxed reaction solution was cooled to room temperature and recrystallized with methanol. The precipitated crystals were separated by filtration and the obtained residue was purified by silica gel column chromatography, providing 36.7 g of the first crystalline intermediate (A) (yield 62.4%).

Step 2: Synthesis of Intermediate Product (B)

35.0 g (72 mmol) of intermediate product (A) was dissolved in 350 ml of tetrahydrofuran, and then 61.5 ml (98 mmol) of n-butyl lithium hexane solution (1.6 M) was added thereto under an argon atmosphere at −70° C. The obtained solution was agitated at −70° C. to 40° C. for 1 hour. The agitated reaction solution was cooled to −70° C., and 29.3 ml (144 mmol) of isopropyltetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The agitated reaction solution was separated into two liquid layers, and an organic layer thereof was dried with anhydrous sodium sulfate. After the organic solvent was removed under a reduced pressure, the obtained residue was purified with silica gel column chromatography to provide 25.1 g of the crystalline intermediate (B) (yield 65.4%).

Step 3: Synthesis of Intermediate Product (C)

45.1 g (84 mmol) of the intermediate product (B), 20.0 g (84 mmol) of 3,5-dibromopyridine, and 2.44 g (2.1 mmol) of tetrakis(triphenylphosphine)palladium were suspended in 600 ml of tetrahydrofuran and 400 ml of toluene, and then a solution of 23.3 g (169 mmol) of potassium carbonate dissolved in 400 ml of water was added. The obtained mixture was refluxed for 12 hours while heating. The refluxed reaction solution was separated into two layers, and an organic layer thereof was cleaned with a sodium chloride saturated aqueous solution and dried with anhydrous sodium sulfate.

Subsequently, the organic solvent was removed by distillation under reduced pressure, and the residue was recrystallized with toluene. The precipitated crystals were separated by filtration and cleaned with toluene to provide 30.7 g (64.4%) of the intermediate product (C).

Step 4: Synthesis of Intermediate Product (D)

10 g (30 mmol) of 9,10-dibromobenzene, 7.6 g (30 mmol) of 1-naphthalene boronic acid, and 1.73 g (1.5 mmol) of tetrakis(triphenylphosphine)palladium were suspended in 500 ml of toluene, then added with a solution of 4.14 g (30 mmol) of potassium carbonate dissolved in 60 ml of water. The obtained mixture was refluxed for 12 hours while heating.

The refluxed reaction solution was separated into two layers, and an organic layer thereof was cleaned with a sodium chloride saturated aqueous solution and dried with anhydrous sodium sulfate. The organic solvent was removed by distillation under reduced pressure, and the residue was recrystallized with toluene.

The precipitated crystals were separated by filtration and cleaned with toluene to provide 5.97 g (52%) of the intermediate product (D).

Step 5: Synthesis of Intermediate Product (E)

5 g (13 mmol) of the intermediate product (D) was dissolved in 350 ml of tetrahydrofuran, and then 8.12 ml (13 mmol) of n-butyl lithium hexane solution (1.6 M) was added thereto under an argon atmosphere at −70° C. The obtained solution was agitated at −70° C. to 40° C. for 1 hour. The agitated reaction solution was cooled to −70° C., and 2.41 g (13 mmol) of isopropyltetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The agitated reaction solution was separated into two liquid layers, and an organic layer thereof was dried with anhydrous sodium sulfate. After the organic solvent was removed under a reduced pressure, the obtained residue was purified with silica gel column chromatography to provide 3.5 g of the crystalline intermediate (E) (yield 60%).

Step 6: Synthesis of the Compound (16)

3 g (5.3 mmol) of the intermediate product (C), 2.28 g (5.3 mmol) of the intermediate product (E), and 0.3 g (0.26 mmol)

of tetrakis(triphenylphosphine)palladium were suspended in 100 ml of tetrahydrofuran and 100 ml of toluene, and then a solution of 0.73 g (5.3 mmol) of potassium carbonate dissolved in 100 ml of water was added. The obtained mixture was refluxed for 9 hours while heating. The refluxed reaction solution was separated into two layers, and an organic layer thereof was cleaned with a sodium chloride saturated aqueous solution and dried with anhydrous sodium sulfate.

The organic solvent was removed by distillation under reduced pressure, and the residue was recrystallized with toluene. The precipitated crystals were separated by filtration and cleaned with toluene to provide 2.21 g (53%) of the compound (16).

EXAMPLE 1-2

Synthesis of Compound (24)

The following compound (24) was synthesized as shown in the following Reaction Scheme 2.

[Reaction Scheme 2]

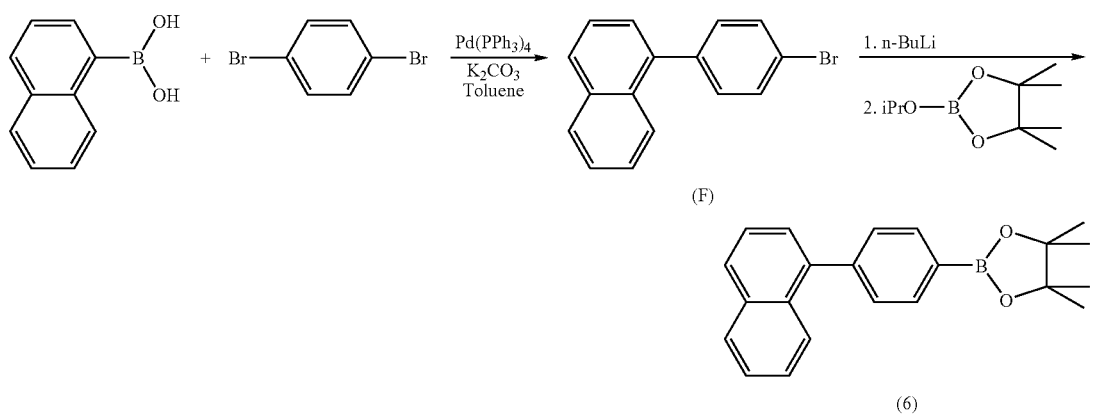

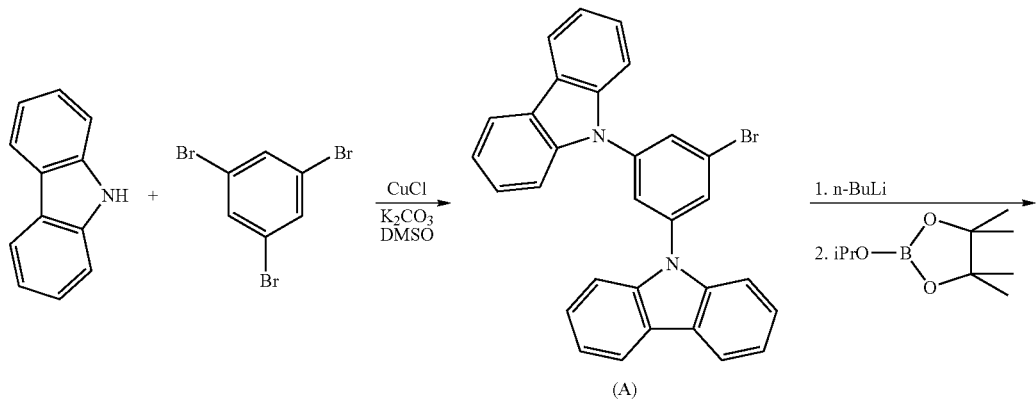

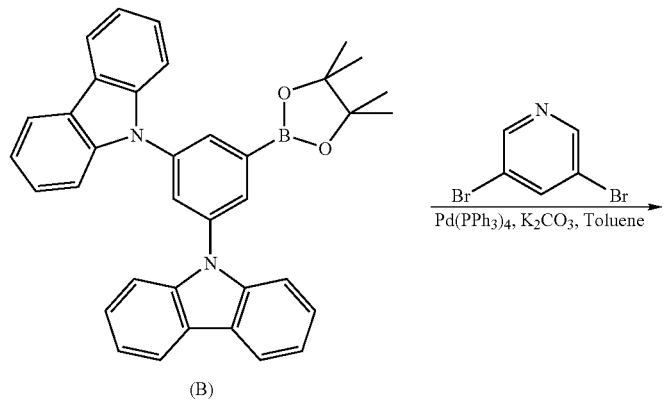

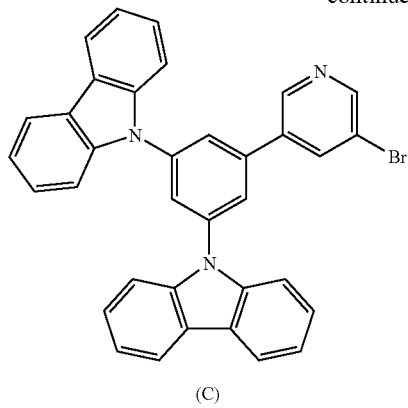

(C)

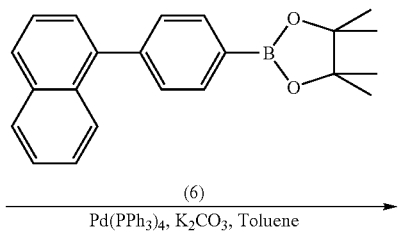

(6)
―――――――――――→
Pd(PPh₃)₄, K₂CO₃, Toluene

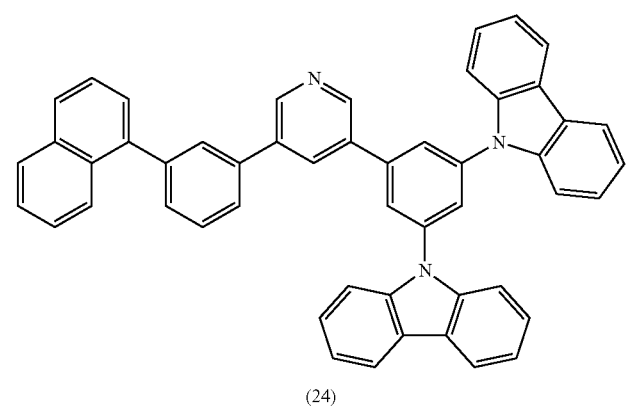

(24)

Step 1: Synthesis of Intermediate Product (F)

15 g (63 mmol) of 1,3-dibromobenzene, 7.66 g (44 mmol) of 1-naphthalene boronic acid, 17.58 g (127 mmol) of potassium carbonate, and 1.83 g (50 mmol) of tetrakis(triphenylphosphine)palladium were suspended in 200 ml of tetrahydrofuran, 200 ml of toluene, and 50 ml of purified water, and refluxed under a nitrogen atmosphere for 24 hours while heating.

The refluxed reaction solution was cooled to room temperature, and the reaction solution was separated into two layers. The solution obtained after the organic solvent of the organic layer was removed under a reduced pressure was separated using column chromatography (hexane), and then solvent was removed to obtain 15 g (83%) of a gel-type intermediate product (F).

Step 2: Synthesis of Intermediate Product (G)

7 g (24 mmol) of the intermediate product (F) was dissolved in 50 ml of tetrahydrofuran, and then 15 ml (24 mmol) of n-butyl lithium hexane solution (1.6 M) was added thereto under an argon atmosphere at −70° C. The obtained solution was agitated at −70° C. for 30 minutes. 47.9 ml (235 mmol) of isopropyltetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The agitated reaction solution was separated into two liquid layers and the organic solvent was removed under reduced pressure. The obtained residue was purified with silica gel column chromatography to provide 6 g of the intermediate product (G) (yield 73%).

Step 3: Synthesis of Compound (24)

4 g (7 mmol) of the intermediate product (C), 2.81 g (8.5 mmol) of the intermediate product (G), 1.96 g (14 mmol) of potassium carbonate, and 0.41 g (0.3 mmol) of tetrakis(triphenylphosphine)palladium were suspended in 200 ml of toluene, 200 ml of tetrahydrofuran, and 50 ml of purified water. The obtained mixture was agitated for 24 hours while heating.

The agitated reaction solution was cooled to room temperature and was separated into two liquid layers, and the organic solvent was removed under reduced pressure. The obtained residue was purified with silica gel column chromatography to provide 4 g of the compound (24) (yield 82%).

EXAMPLE 1-3

Synthesis of Compound (26)

The following compound (26) was synthesized as shown in the following Reaction Scheme 3.

[Reaction Scheme 3]

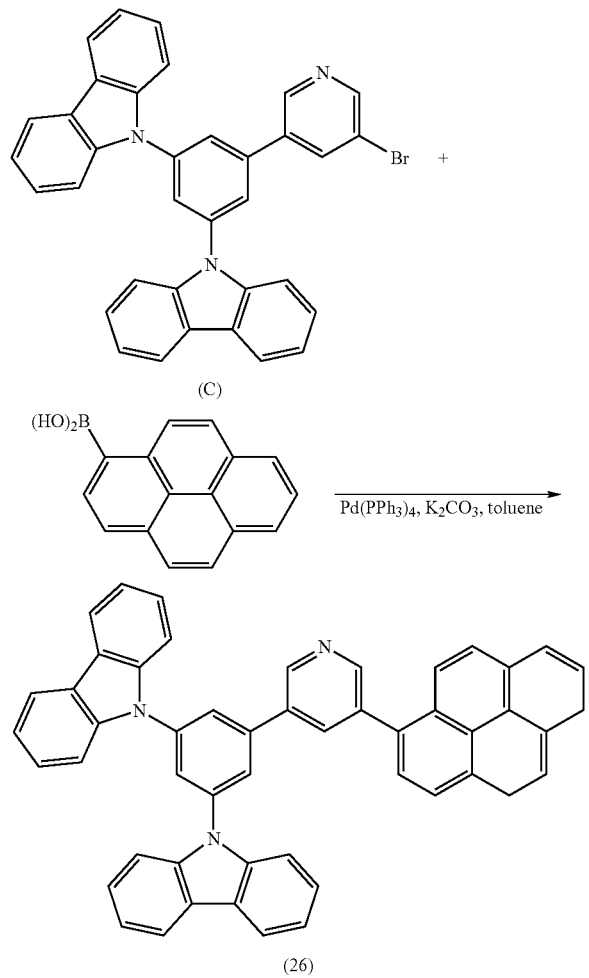

3 g (5.3 mmol) of the intermediate product (C), 1.3 g (5.3 mmol) of pyrene-1-boronic acid, and 0.3 g (0.2 mmol) of tetrakis(triphenylphosphine)palladium were suspended in 150 ml of tetrahydrofuran and 150 ml of toluene, and then a solution of 1.38 g (10 mmol) of potassium carbonate dissolved in 20 ml of water was added. The obtained mixture was refluxed for 9 hours while heating.

The refluxed reaction solution was separated into two liquid layers, and an organic layer thereof was cleaned with a sodium chloride saturated aqueous solution and then dried with anhydrous sodium sulfate. After the organic solvent was removed under a reduced pressure, the obtained residue was recrystallized with toluene. The precipitated crystals were separated by filtration and cleaned with toluene, providing 2.73 g of the first crystalline compound (26) (yield 75%).

EXAMPLE 1-4

Synthesis of Compound (51)

The following compound (51) was synthesized as shown in the following Reaction Scheme 4.

[Reaction Scheme 4]

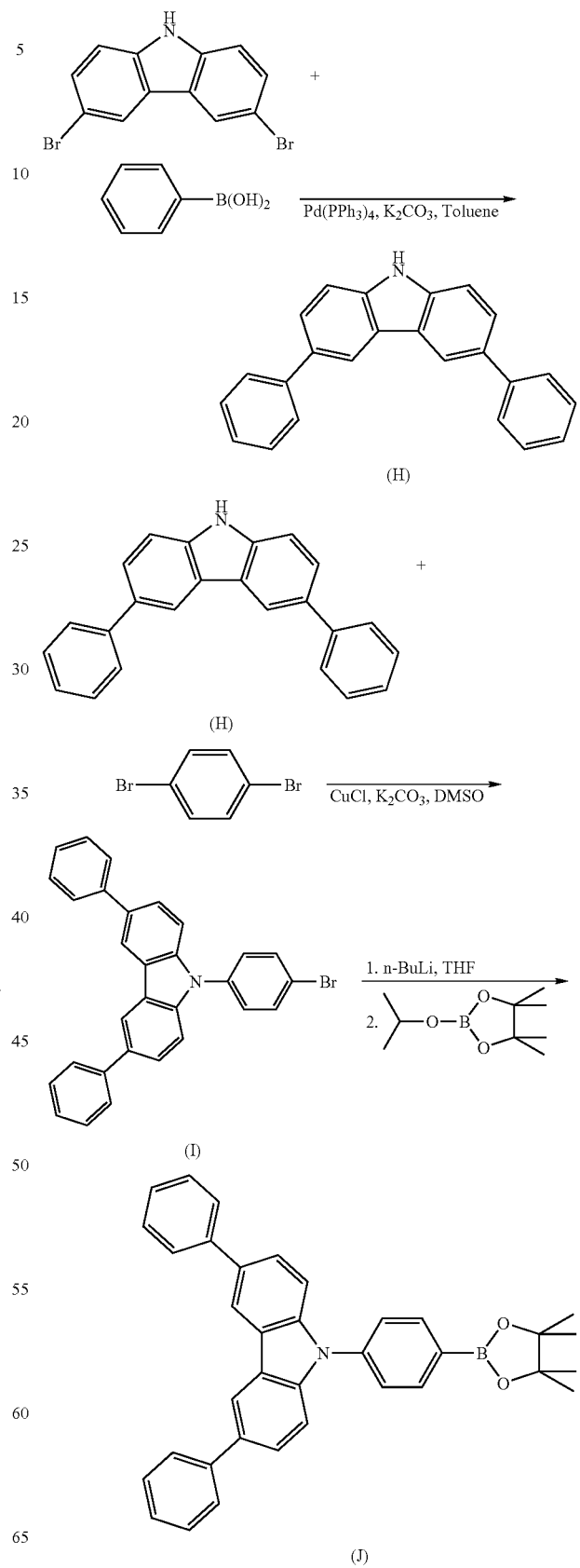

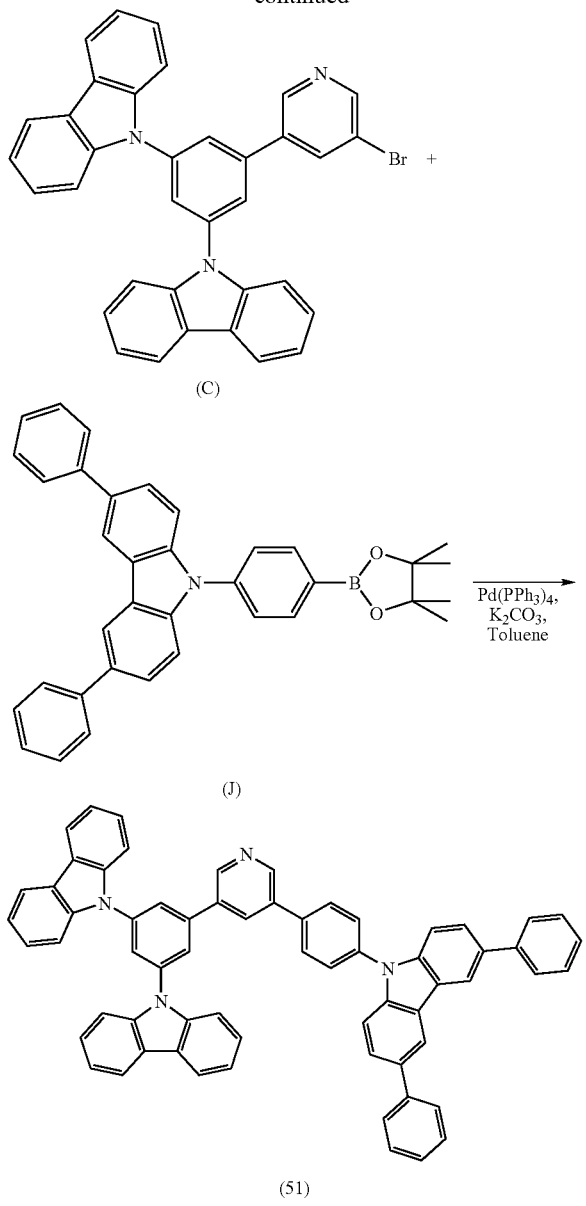

Step 1: Synthesis of Intermediate Product (H)

3 g (9 mmol) of 3,6-dibromobenzene, 2.25 g (18 mmol) of benzene boronic acid, 5 g (36 mmol) of potassium carbonate, and 0.2 g (0.18 mmol) of tetrakis(triphenylphosphine)palladium were suspended in 200 ml of toluene and 50 ml of purified water, and refluxed under a nitrogen atmosphere for 24 hours while heating.

The refluxed reaction solution was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 1.43 g (50%) of the intermediate product (H).

Step 2: Synthesis of Intermediate Product (I)

5 g (21 mmol) of 1,4-dibromobenzene, 6.7 g (21 mmol) of the intermediate product (H), 2.9 g (21 mmol) of potassium carbonate, and 200 mg (0.018 mmol) of cuprous chloride were suspended in 200 ml of tetrahydrofuran and 200 ml of dimethylsulfoxide, and refluxed under a nitrogen atmosphere for 24 hours while heating.

The refluxed reaction solution was separated into two liquid layers, and an organic layer thereof was cleaned with a sodium chloride saturated aqueous solution and then dried with anhydrous sodium sulfate. After the organic solvent was removed under a reduced pressure, the obtained residue was recrystallized with toluene. The precipitated crystals were separated by filtration and cleaned with toluene, providing 4.28 g of the first crystalline intermediate compound (I) (yield 43%).

Step 3: Synthesis of Intermediate Product (J)

5 g (9.5 mmol) of the intermediate product (I) was suspended in 200 ml of tetrahydrofuran, and then 5.93 ml (9.5 mmol) of an n-butyllithium hexane solution (1.6 M) was added thereto under an argon atmosphere at −76° C. After 30 minutes, 1.76 g (9.5 mmol) of isopropyltetramethyldioxaborolane was added to the suspension to obtain a reaction solution. Then the temperature of the reaction solution was increased to room temperature.

The reaction solution was separated into two layers, and an organic layer thereof was cleaned with a sodium chloride saturated aqueous solution and dried with anhydrous sodium sulfate. The organic solvent was removed by distillation under reduced pressure, and the residue was recrystallized with toluene. The precipitated crystals were separated by filtration and cleaned with hexane to provide 3.17 g (64%) of the intermediate product (J).

Step 4: Synthesis of Compound (51)

3 g (5.3 mmol) of the intermediate product (C), 2.76 g (5.3 mmol) of the intermediate product (J), 1.96 g (14 mmol) of potassium carbonate, and 0.41 g (0.3 mmol) of tetrakis(triphenylphosphine)palladium were suspended in 200 ml of toluene and 50 ml of purified water. The obtained suspension was agitated for 24 hours.

The agitated reaction solution was cooled to room temperature. Then the solution was separated into two layers and the organic solvent was removed by distillation under reduced pressure to provide a residue. The residue was purified using silica gel column chromatography to provide 3.49 g of the compound (51) (yield 75%).

EXAMPLE 1-5

Synthesis of Compound (53)

The following compound (53) was synthesized as shown in the following Reaction Scheme 5.

[Reaction Scheme 5]

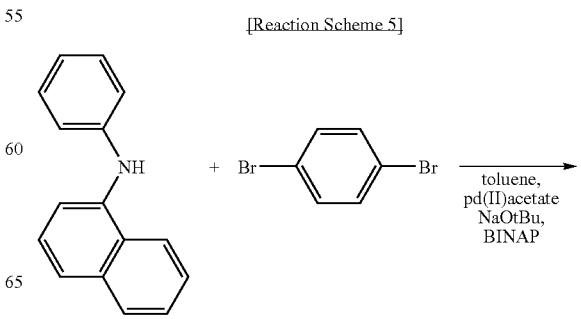

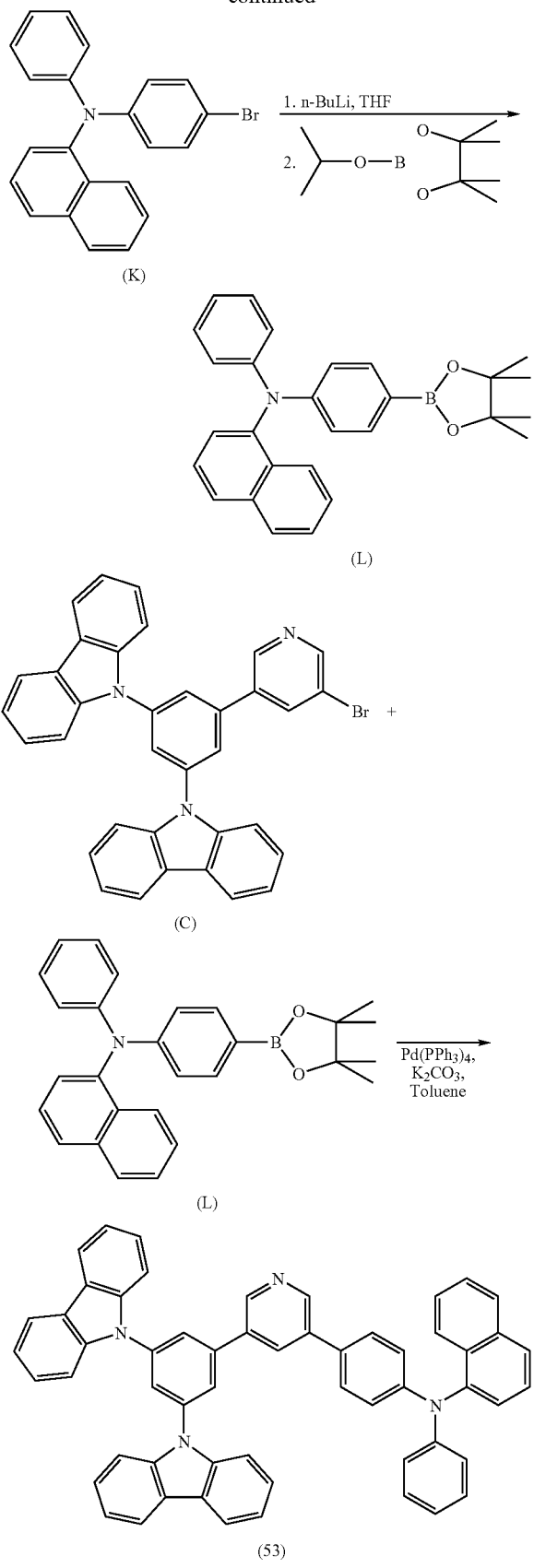

Step 1: Synthesis of Intermediate Product (K)

3.22 g (13 mmol) of 3,6-dibromobenzene, 3 g (13 mmol) of N-phenyl-1-naphthylamine, 1.24 g (13 mmol) of sodium-t-butoxide, 30 mg (0.13 mmol) of palladium acetate, and 80 mg (0.13 mmol) of 2,2'-bis(diphenylphosphino)-1,1'-binaphthyl (BINAP) were suspended in 200 ml of toluene, and refluxed under a nitrogen atmosphere for 24 hours while heating.

The refluxed reaction solution was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 2.04 g (42%) of the intermediate product (K).

Step 2: Synthesis of Intermediate Product (L)

3 g (8 mmol) of the intermediate product (K) was suspended in 200 ml of tetrahydrofuran, and then 5 ml (8 mmol) of n-butyllithium hexane solution (1.6 M) was added thereto under an argon atmosphere at −76° C. After 30 minutes, 1.48 g (8 mmol) of isopropyltetramethyldioxaborolane was added to the suspension to obtain a reaction solution. Then the temperature of the reaction solution increased to room temperature.

The reaction solution was separated into two layers, and an organic layer thereof was cleaned with a sodium chloride saturated aqueous solution and dried with anhydrous sodium sulfate. The organic solvent was removed by distillation under reduced pressure, and the residue was recrystallized with toluene. The precipitated crystals were separated by filtration and cleaned with hexane to provide 2.62 g (78%) of the intermediate product (L).

Step 4: Synthesis of Compound (53)

3 g (5.3 mmol) of the intermediate product (C), 2.23 g (5.3 mmol) of the intermediate product (L), 1.96 g (14 mmol) of potassium carbonate, and 0.419 (0.3 mmol) of tetrakis(triphenylphosphine)palladium were suspended in 200 ml of toluene and 50 ml of purified water. The obtained suspension was agitated for 24 hours.

The agitated reaction solution was cooled to room temperature. Then the solution was separated into two layers and the organic solvent was removed by distillation under reduced pressure to provide a residue. The residue was purified using silica gel column chromatography to provide 2.68 g of the compound (53) (yield 65%).

EXAMPLE 2

Fabrication of Organic Photoelectric Device

EXAMPLE 2-1

The organic compound (24) prepared from Example 1-2 was used as a host and Ir(PPy)$_3$ was used as a dopant to provide an organic photoelectric device.

ITO was provided in a thickness of 1000 Å for an anode, and aluminum (Al) was provided in a thickness of 1000 Å for a cathode.

The method of manufacturing an organic photoelectric device may be described in detail as follows: cutting an ITO glass substrate having a sheet resistance value of 15 Ω/cm$^2$ into a size of 50 mm×50 mm×0.7 mm for a cathode; ultrasonic wave cleaning the same in acetone, isopropyl alcohol, and pure water for 15 minutes, respectively; and UV ozone cleaning for 30 minutes.

DNTPD (N,N'-di(4-(N,N'-diphenyl-amino)phenyl)-N,N'-diphenylbenzidine) and NPD (N,N-di-1-naphthyl-N,N'- diphenylbenzidine) were deposited on the upper surface of the substrate under the conditions of a vacuum degree of 650×10⁻⁷ Pa and a deposition speed of 0.1 to 0.3 nm/s to provide a 900 Å-thick hole transport layer (HTL).

Subsequently, under the same vacuum deposition conditions, the organic compound (24) of Example 1-2 and the phosphorescent dopant Ir(PPy)₃ (wherein PPy is 2-phenylpyridine) were simultaneously deposited to provide an emission layer having a thickness of 300 Å.

During this process, a phosphorescent dopant was deposited at the same time, and the adding amount of the phosphorescent dopant was adjusted to 10 wt % based on the total weight of the emission layer.

Bis(2-methyl-8-quinolinolate)-4-(phenylphenolate)aluminum (Balq) was deposited on the upper surface of the emission layer under the same vacuum deposition conditions to provide a hole blocking layer having a thickness of 50 Å. Subsequently, Alq₃ was deposited under the same vacuum deposition conditions to provide an electron transport layer having a thickness of 200 Å. On the upper surface of the electron transport layer, LiF and Al were sequentially deposited to provide an organic photoelectric device.

The organic photoelectric device had the following five-layered structure: ITO/DNTPD (60 nm)/NPD (30 nm)/compound (24)+Ir(PPy)₃ (10 wt %) (30 nm)/Balq (5 nm)/Alq₃ 20 nm/LiF/Al 100 nm.

EXAMPLE 2-2

The organic compound (51) prepared from Example 1-4 was used as a host and Ir(Piq)₂(acac) was used as a dopant to provide an organic photoelectric device.

ITO was provided in a thickness of 1000 Å for an anode, and aluminum (Al) was provided in a thickness of 1000 Å for a cathode.

The method of manufacturing an organic photoelectric device may be described in detail as follows: cutting an ITO glass substrate having a sheet resistance value of 15 Ω/cm² into a size of 50 mm×50 mm×0.7 mm for a cathode; ultrasonic wave cleaning the same in acetone, isopropyl alcohol, and pure water for 15 minutes, respectively; and UV ozone cleaning for 30 minutes.

DNTPD and NPD were deposited on the upper surface of the substrate under the conditions of a vacuum degree of 650×10⁻⁷ Pa and a deposition speed of 0.1 to 0.3 nm/s to provide a 900 Å-thick hole transport layer (HTL).

Subsequently, under the same vacuum deposition conditions, the organic compound (51) and the phosphorescent dopant Ir(Piq)₂(acac) were simultaneously deposited to provide an emission layer having a thickness of 300 Å.

During this process, a phosphorescent dopant was deposited at the same time, and the adding amount of the phosphorescent dopant was adjusted to 10 wt % based on the total weight of the emission layer.

BCP (2,9-dimethyl-4,7-diphenyl-1,10-phenanthroline) was deposited on the upper surface of the emission layer under the same vacuum deposition conditions to provide a hole blocking layer having a thickness of 50 Å. Subsequently, Alq₃ was deposited under the same vacuum deposition conditions to provide an electron transport layer having a thickness of 200 Å.

On the upper surface of the electron transport layer, LiF and Al were sequentially deposited to provide an organic photoelectric device. The organic photoelectric device has the following five-layered structure: ITO/DNTPD (60 nm)/NPD (30 nm)/compound (51)+Ir(Piq)₂(acac) (10 wt %, 30 nm)/BCP (5 nm)/Alq₃ (20 nm)/LiF/Al (100 nm).

EXAMPLE 2-3

The organic photoelectric device was fabricated according to the same manner as in Example 2-2, except that the compound (53) according to Example 1-5 was used as a host.

COMPARATIVE EXAMPLE 1

The organic photoelectric device was fabricated according to the same manner as in Example 2-1, except that 4,4-N,N-dicarbazolebiphenyl (CBP) having the following Chemical Formula 8 was used as a host instead of the organic compound (24) of Example 2-1. The organic photoelectric device has the following structure: ITO/DNTPD (60 nm)/NPD (30 nm)/CBP+Ir(PPy)₃ (10 wt %, 30 nm)/Balq (5 nm)/Alq₃ (20 nm)/LiF/Al (100 nm).

[Chemical Formula 8]

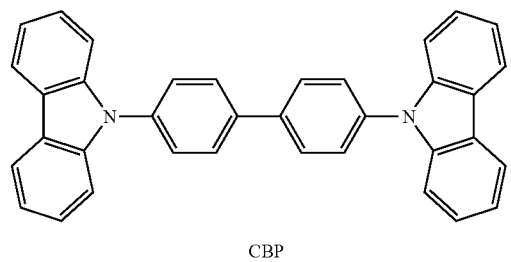

CBP

COMPARATIVE EXAMPLE 2

The organic photoelectric device was fabricated according to the same manner as in Example 2-2, except that 4,4-N,N-dicarbazolebiphenyl (CBP) having the structure shown in Chemical Formula 8 was used as a host instead of the organic compound (51) of Example 2-2. The organic photoelectric device has the following structure: ITO/DNTPD (60 nm)/NPD (30 nm)/CBP+Ir(Piq)₂(acac) (10 wt %, 30 nm)/BCP (5 nm)/Alq₃ (20 nm)/LiF/Al 100 nm.

Properties Measurement of the Materials

The material prepared according to Example 1-2 was analyzed for ¹H-NMR using Bruker 300 MHz. It was confirmed that the material prepared according to Example 1-2 was the compound (24).

¹H NMR (200 MHz, CDCl₃) δ 8.95(2H, d), 8.21 (5H, m), 8.1 (2H, d), 7.91 (3H, t), 7.7 (2H, m), 7.4 (19H, m) ppm.

Glass transition temperature (Tg) and thermal decomposition temperature (Td) of the materials according to Examples 1-2, 1-4, and 1-5 were measured using differential scanning calorimetry (DSC) and thermogravimetric analysis (TGA). The glass transition temperature (Tg) and thermal decomposition temperature (Td) of the material according to Example 1-2 are shown in Table 1, and those of Examples 1-4 and 1-5 are shown in Table 2.

The glass transition temperature (Tg) and thermal decomposition temperature (Td) of the material CBP according to Comparative Examples 1 and 2 were also measured using DSC and TGA. The results are shown in Tables 1 and 2.

Performance Measurement of Organic Photoelectric Device

Each organic photoelectric device according to Example 2-1, Example 2-2, and Comparative Example 1 was measured regarding luminous efficiency in accordance with a voltage as below.

1) Current Density According to a Voltage Change

Each organic photoelectric device according to Examples 2-1 to 2-3 and Comparative Examples 1 and 2 was measured for a current value passing through the unit device using a current-voltage meter (Keithley 2400) while increasing the voltage from 0 V to 14 V. The results were calculated by dividing the measured current value by the area.

2) Luminance According to a Voltage Change

Each organic photoelectric device according to Examples 2-1 to 2-3 and Comparative Examples 1 and 2 was measured for luminance by a luminance meter (Minolta Cs-1000A) while increasing the voltage from 0 V to 14 V.

3) Luminous Efficiency

Luminous efficiency was calculated by using the luminance, current density, and voltage measured from the above 1) and 2). The results of Example 2-1 and Comparative Example 1 are shown in Table 1 and the results of Examples 2-2 and 2-3 and Comparative Example 2 are shown in Table 2.

TABLE 1

| | | | | Luminance at 100 nit | | |
| | Host of emission layer | Tg (° C.) | Td (° C.) | Driving voltage (V) | Luminous efficiency (lm/W) | Color coordinate (x, y) |
| --- | --- | --- | --- | --- | --- | --- |
| Ex. 2-1 | Compound (24) | 126 | 517 | 4.5 | 24.9 | 0.30, 0.62 |
| Comp. Ex. 1 | CBP | 110 | 392 | 6 | 16.7 | 0.28, 0.62 |

TABLE 2

| | | | | Luminance at 100 nit | | |
| | Host of emission layer | Tg (° C.) | Td (° C.) | Driving voltage (V) | Luminous efficiency (lm/W) | Color coordinate (x, y) |
| --- | --- | --- | --- | --- | --- | --- |
| Ex. 2-2 | Compound (51) | NM* | 560 | 5 | 3.88 | 0.67, 0.31 |
| Ex. 2-3 | Compound (53) | 154 | 494 | 6 | 4.09 | 0.68, 0.31 |
| Comp. Ex. 2 | CBP | 110 | 392 | 6.5 | 3.83 | 0.68, 0.31 |

*No measurement

Referring to Tables 1 and 2, the most bipolar organic compound according to the examples of the present invention has a glass transition temperature of 120° C. or more and a thermal decomposition temperature (Td) of 430° C. or more. Therefore, the bipolar organic compounds have high thermal stability compared to a host material CBP according to Comparative Examples 1 and 2 (110° C.).

The organic photoelectric devices according to the examples show a driving voltage of 6 V or less at a luminance of 100 nit, and an equivalent or improved luminous efficiency compared to that according to Comparative Examples 1 and 2. The organic photoelectric device according to Example 2-1 shows a low driving voltage that is about 1.5 V less than that of Comparative Example 1.

The organic photoelectric device according to Example 2-2 shows a low driving voltage that is about 1.5 V less than that of Comparative Example 2, and the organic photoelectric device according to Example 2-3 shows a low driving voltage that is about 0.5 V less than that of Comparative Example 2.

The organic photoelectric device according to Example 2-1 shows improved device performance relative to that of Comparative Example 1. As shown in Table 2, the organic photoelectric device according to Example 2-2 shows equivalent luminous efficiency to that of Comparative Example 2, and the organic photoelectric device according to Example 2-3 shows generally more improved device characteristics than those of Comparative Example 2.

The material for an organic photoelectric device according to embodiments may have high thermal stability, and may be used to provide an organic photoelectric device having a low driving voltage and high luminous efficiency. The material for an organic photoelectric device according to embodiments may also improve life-span of an organic photoelectric device due to an increase of amorphous properties and high Tg and Td.

As described above, the example materials for an organic photoelectric device according to embodiments of the present invention have been synthesized, and organic photoelectric devices using the materials for an organic photoelectric device have been fabricated therewith. The Examples show improvement of luminous efficiency and decrease of driving voltage.

The efficiency and properties of the light emission diodes are dependent on the host material in the emission layer. An organic host material may be exemplified by a material including naphthalene, anthracene, phenanthrene, tetracene, pyrene, benzopyrene, chrysene, pycene, carbazole, fluorene, biphenyl, terphenyl, triphenylene oxide, dihalobiphenyl, trans-stilbene, and 1,4-diphenylbutadiene. A host material that includes 4,4-N,N-dicarbazolebiphenyl (CBP), having a glass transition temperature of 110° C. or less and a thermal decomposition temperature of 400° C. or less, may have a thermal stability that is low and the symmetry is excessively high. Further, it may tend to crystallize and cause problems such as a short circuit and a pixel defect according to results of thermal resistance tests of the devices. In addition, host materials including CBP may be materials in which the hole transporting property is greater than the electron transporting property. Thus, as the injected hole transportation is faster than the injected electron transportation, the excitons may be ineffectively formed in the emission layer. Therefore, the resultant device may have low luminous efficiency.

In contrast, embodiments of the present invention may provide a material for an organic photoelectric device, and an organic photoelectric device using the same, where the material for an organic photoelectric device may have thermal stability, and good hole and electron transporting properties. Further, embodiments may provide a phosphorescent host material having high electrical stability.

Example embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A material for an organic photoelectric device, the material comprising a compound represented by at least one of the following Chemical Formulae 1-2 to 1-8, 1-10, 1-13 to 1-19, 1-24 to 1-27, 1-29 to 1-45, and 1-52 to 1-53:

[Chemical Formula 1-2]
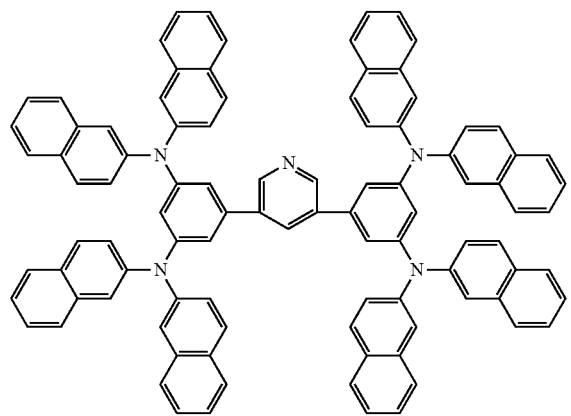
[Chemical Formula 1-5]
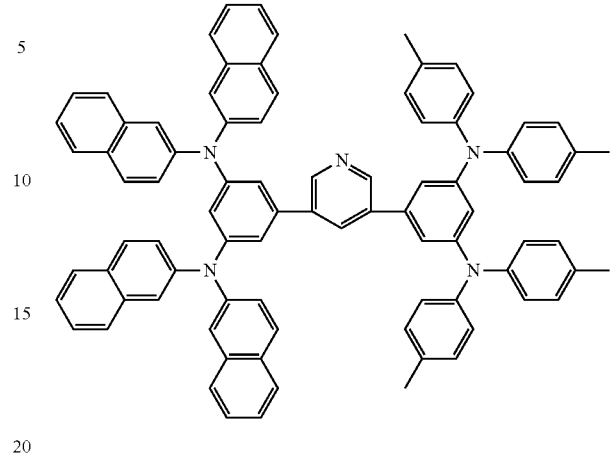
[Chemical Formula 1-3]
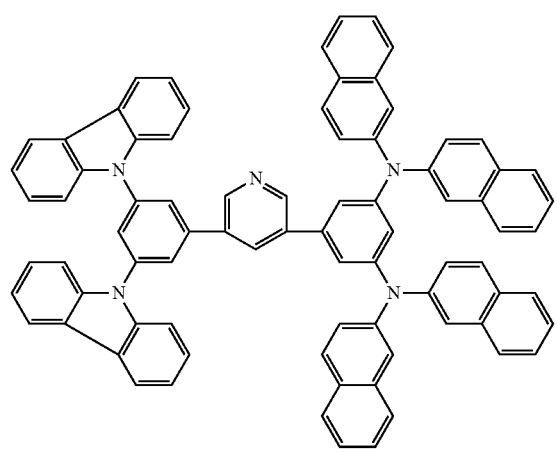
[Chemical Formula 1-6]
[Chemical Formula 1-4]
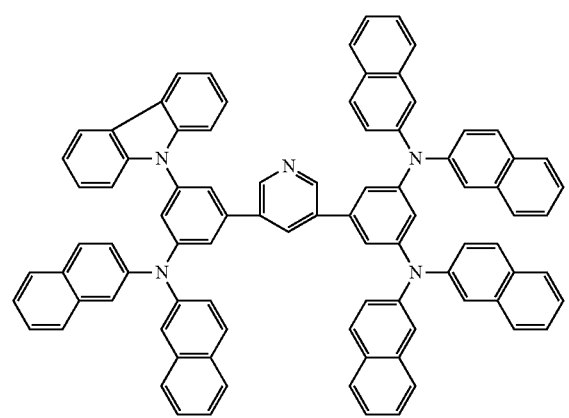
[Chemical Formula 1-7]
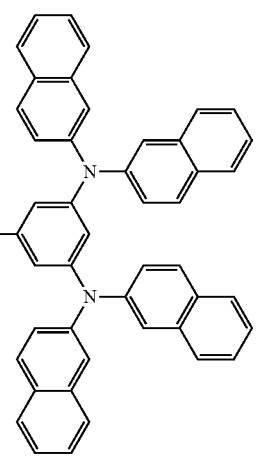

[Chemical Formula 1-8]
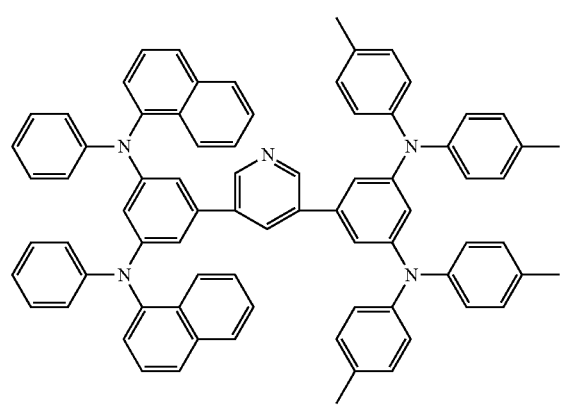
[Chemical Formula 1-14]
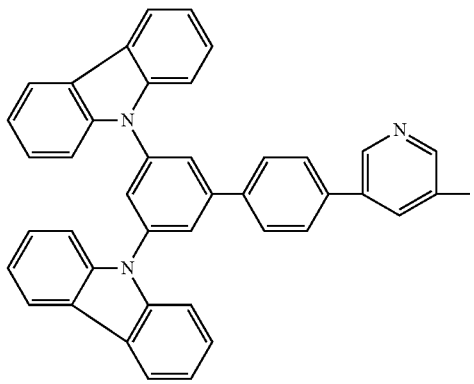
[Chemical Formula 1-10]
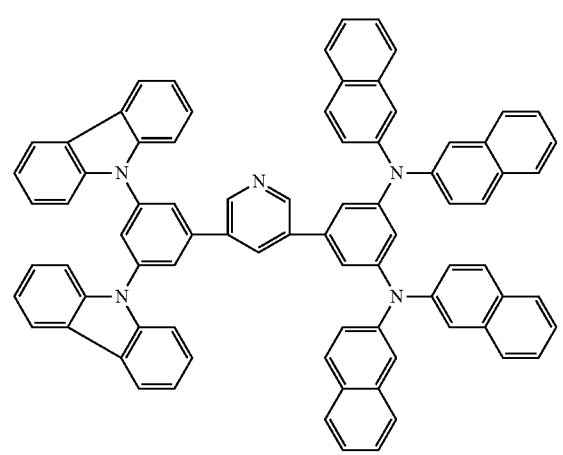
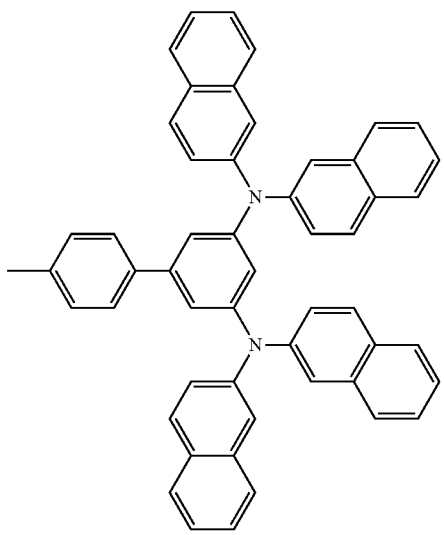
[Chemical Formula 1-13]
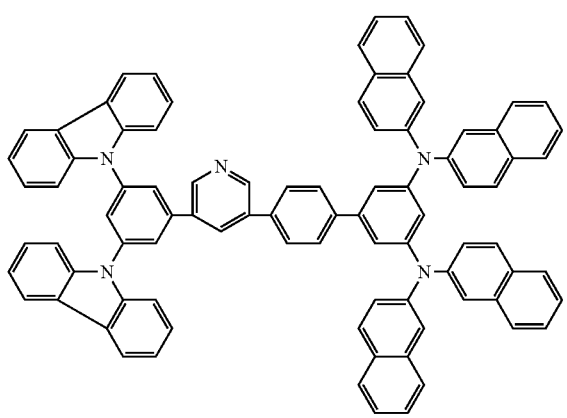
[Chemical Formula 1-15]
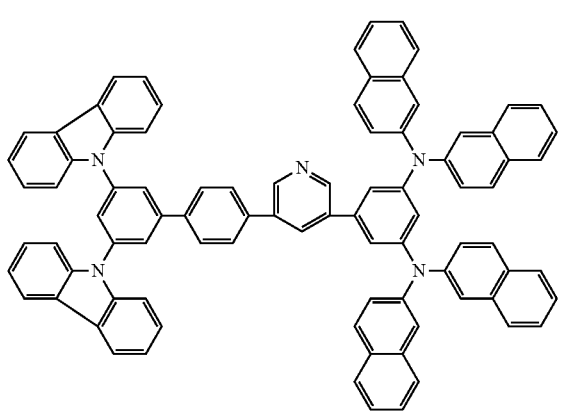

[Chemical Formula 1-16]
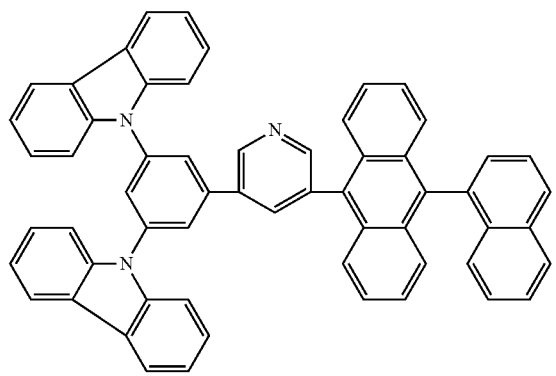
[Chemical Formula 1-17]
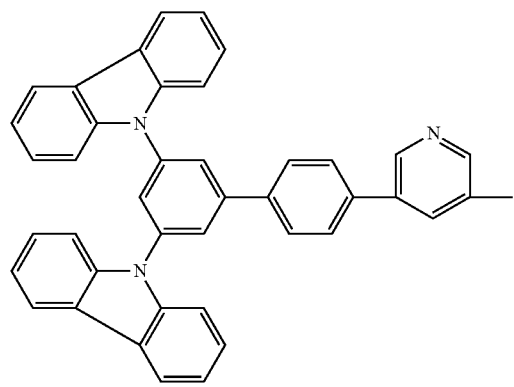
[Chemical Formula 1-18]
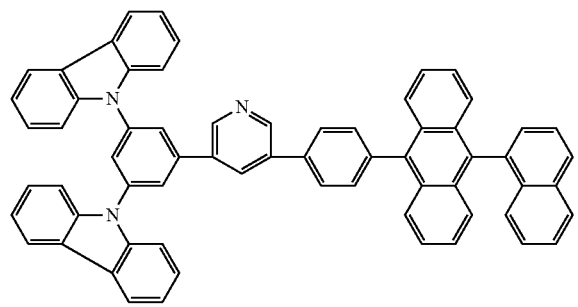
[Chemical Formula 1-19]
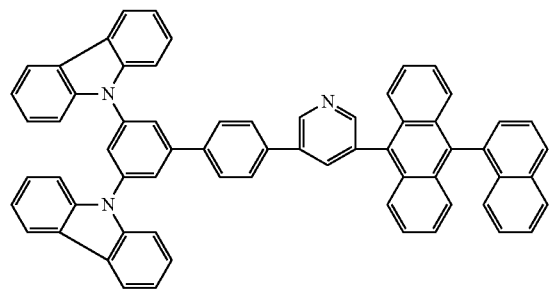
[Chemical Formula 1-24]
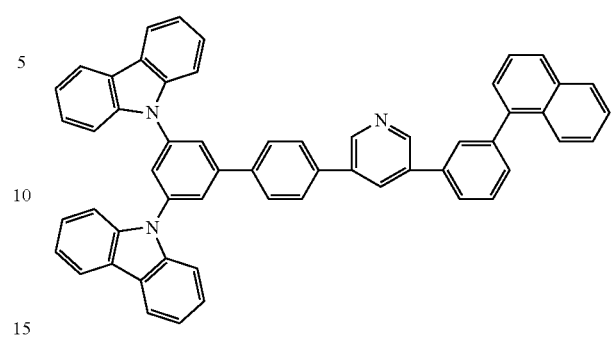
[Chemical Formula 1-25]
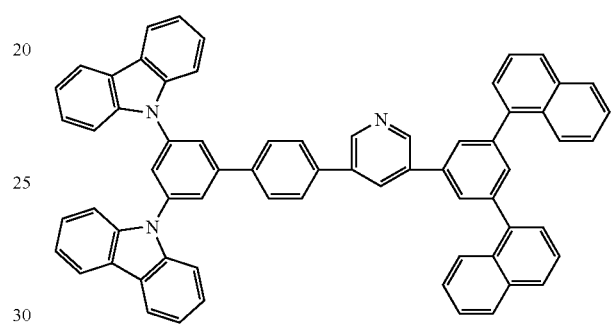
[Chemical Formula 1-26]
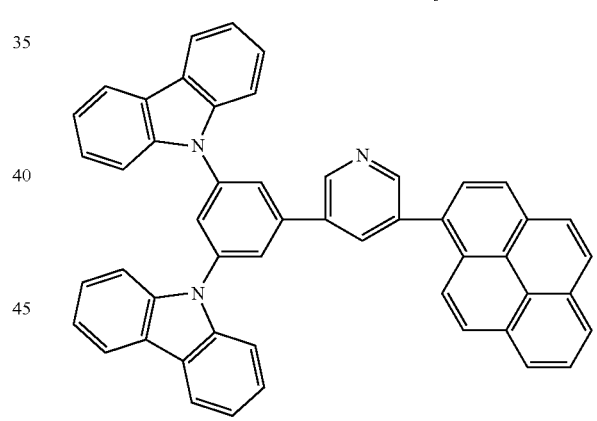
[Chemical Formula 1-27]
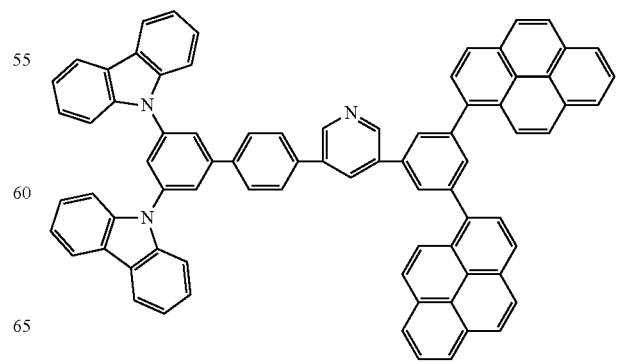

[Chemical Formula 1-29]
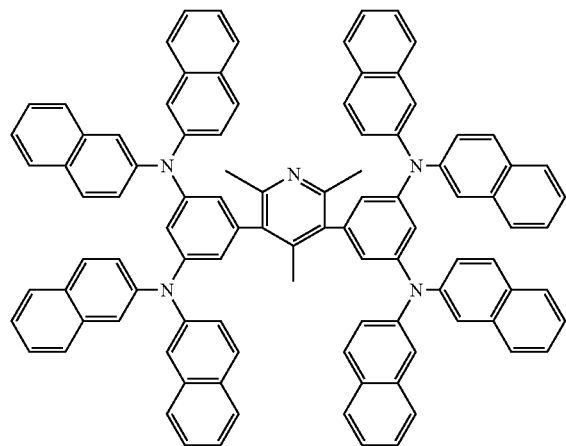
[Chemical Formula 1-30]
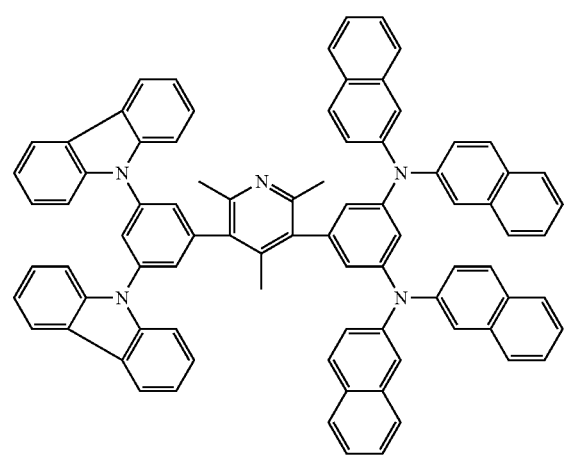
[Chemical Formula 1-31]
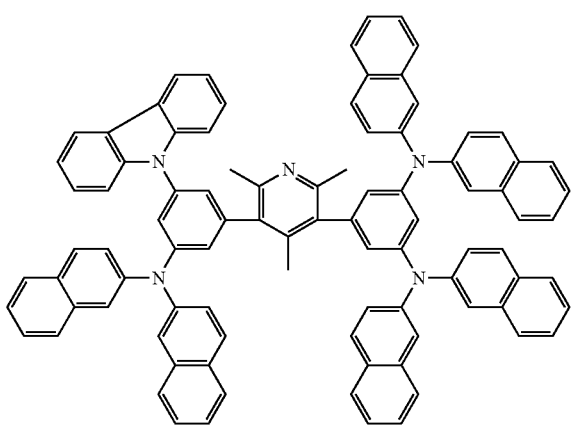
[Chemical Formula 1-32]
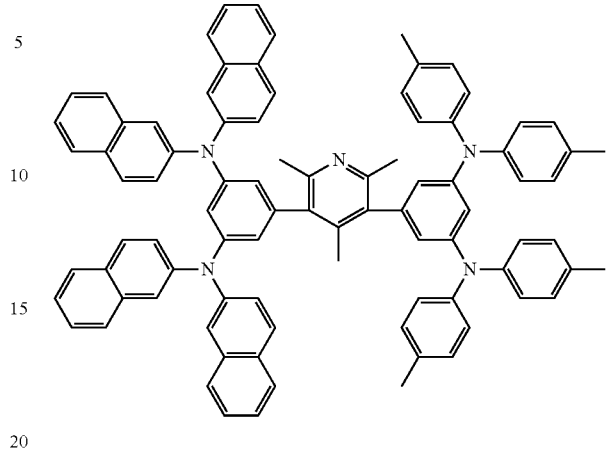
[Chemical Formula 1-33]
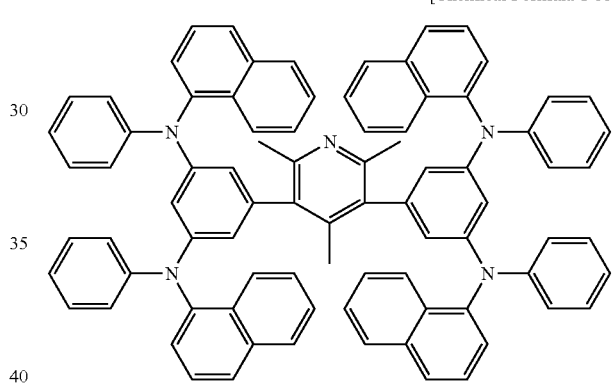
[Chemical Formula 1-34]
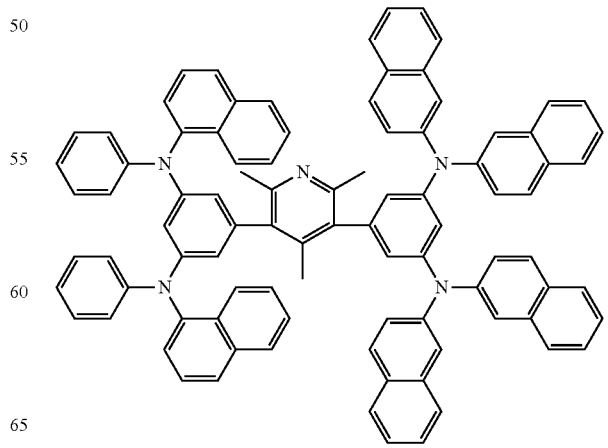

[Chemical Formula 1-35]
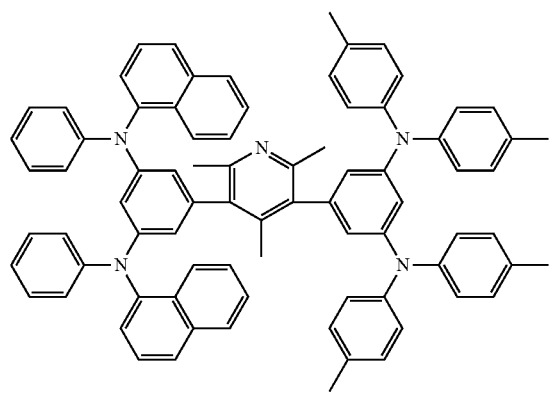
[Chemical Formula 1-36]
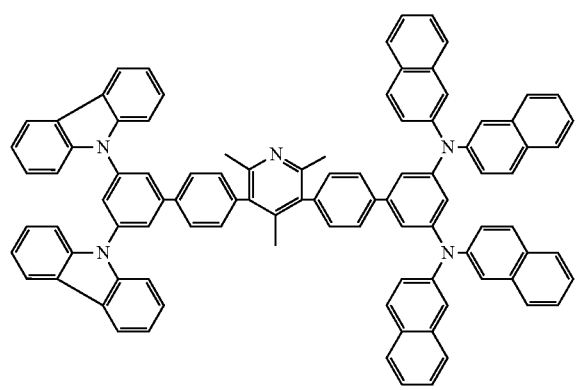
[Chemical Formula 1-37]
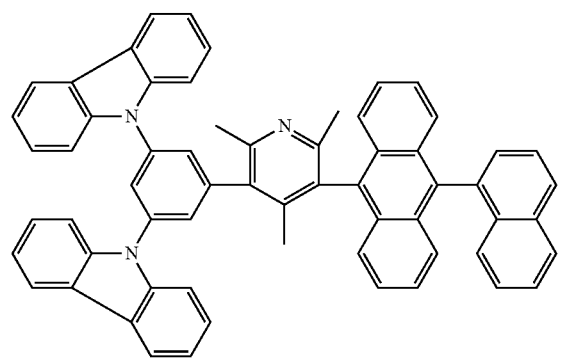
[Chemical Formula 1-38]
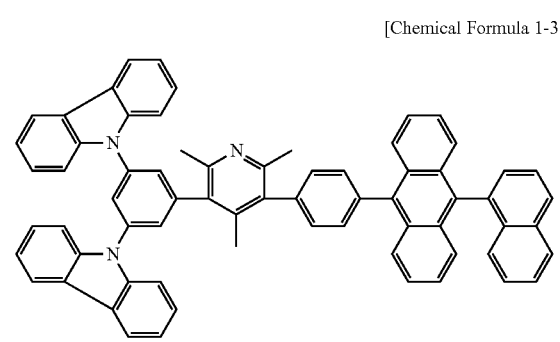
[Chemical Formula 1-39]
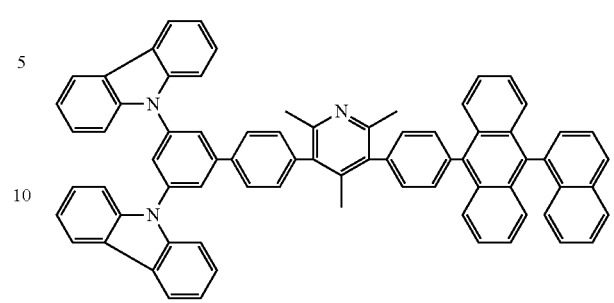
[Chemical Formula 1-40]
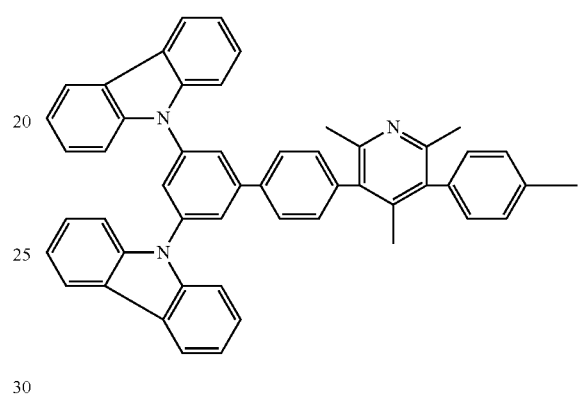
[Chemical Formula 1-41]
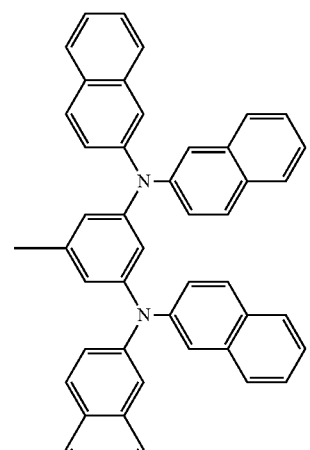
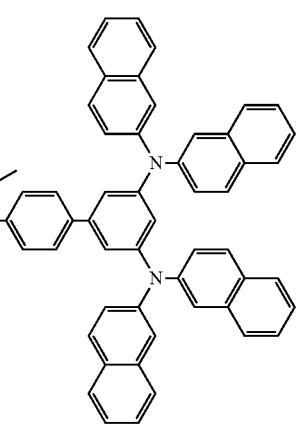

-continued

[Chemical Formula 1-42]

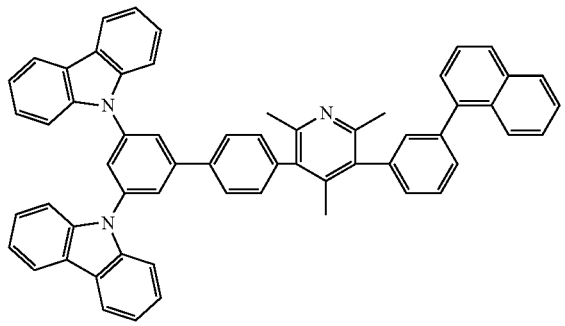

[Chemical Formula 1-43]

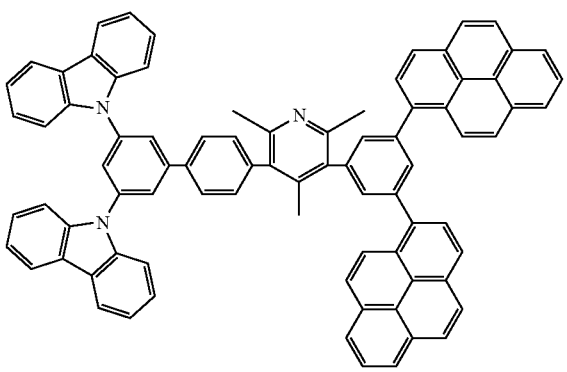

[Chemical Formula 1-44]

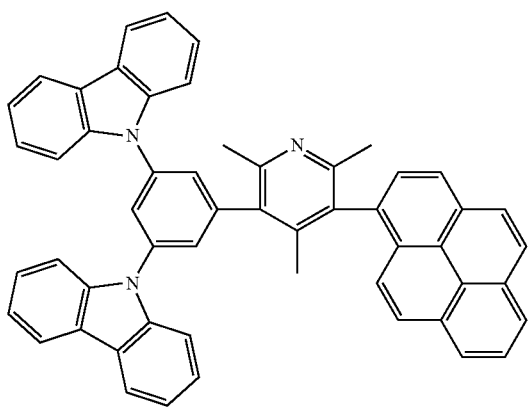

[Chemical Formula 1-45]

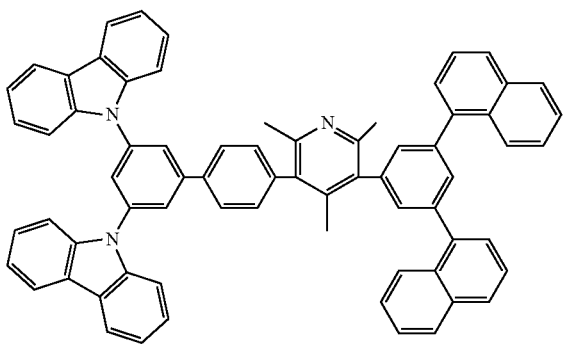

-continued

[Chemical Formula 1-52]

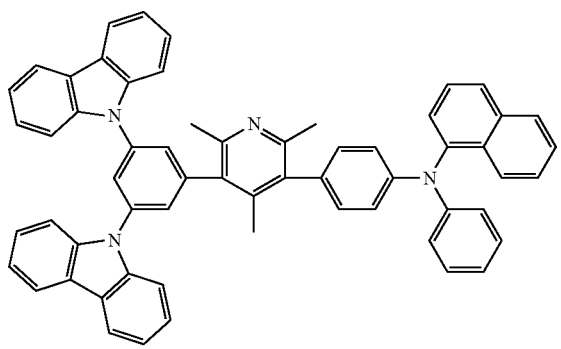

[Chemical Formula 1-53]

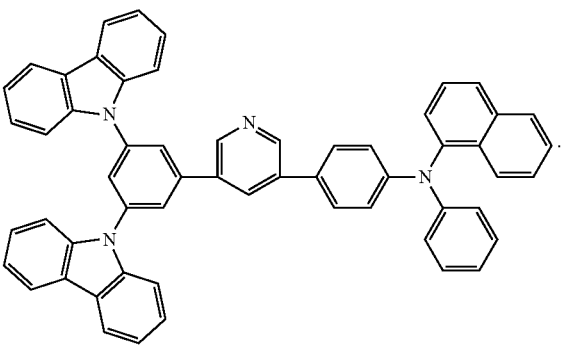

2. An organic photoelectric device, comprising:
an anode, a cathode, and an organic layer disposed between the anode and cathode,
wherein the organic layer includes the material as claimed in claim 1.

3. The organic photoelectric device as claimed in claim 2, wherein the organic layer is an emission layer.

4. The organic photoelectric device as claimed in claim 3, wherein the emission layer comprises:
a phosphorescent or fluorescent host that includes the material, and
a phosphorescent or fluorescent dopant selected from the group of red, green, blue, and white light-emitting dopants.

5. The organic photoelectric device as claimed in claim 2, wherein the organic layer is selected from the group of an emission layer, a hole transport layer (HTL), a hole injection layer (HIL), an electron transport layer (ETL), an electron injection layer (EIL), and combinations thereof.

6. A material for an organic photoelectric device, the material comprising a compound represented by at least one of the following Chemical Formulae 1-3, 1-10, 1-13 to 1-19, 1-24 to 1-27, 1-30, 1-36 to 1-45, and 1-52 to 1-53:
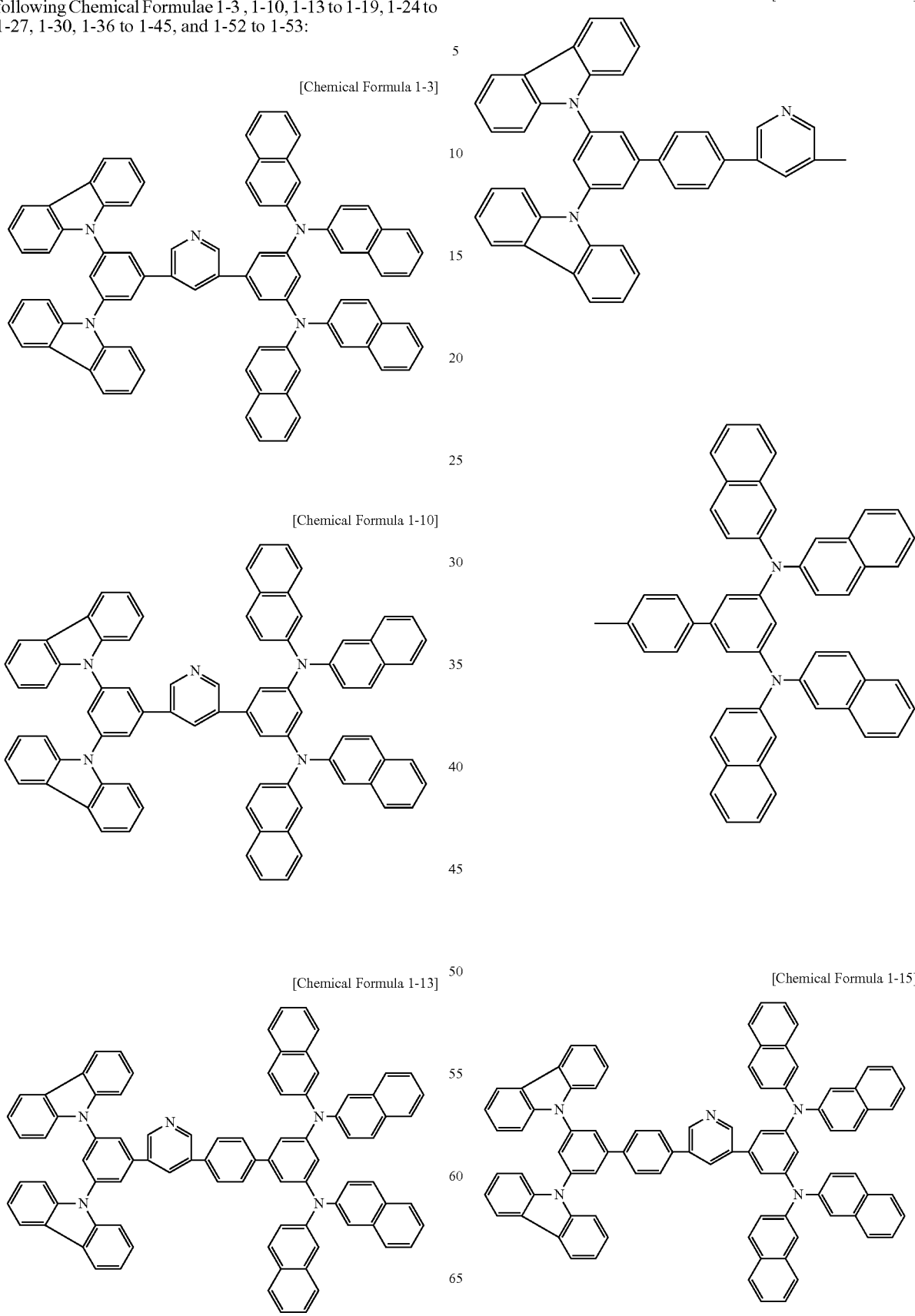

[Chemical Formula 1-16]
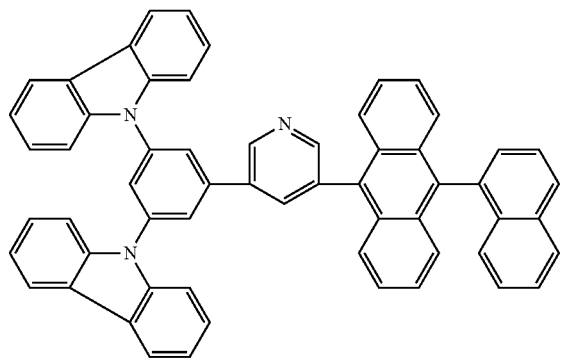
[Chemical Formula 1-17]
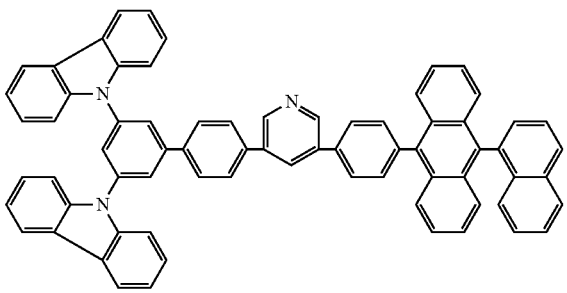
[Chemical Formula 1-18]
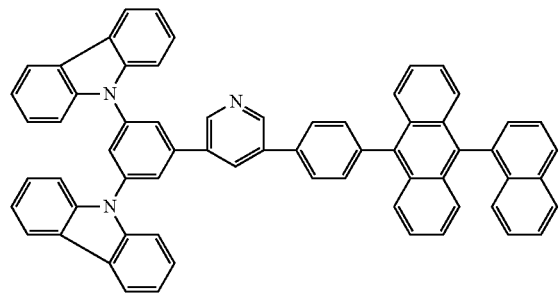
[Chemical Formula 1-19]
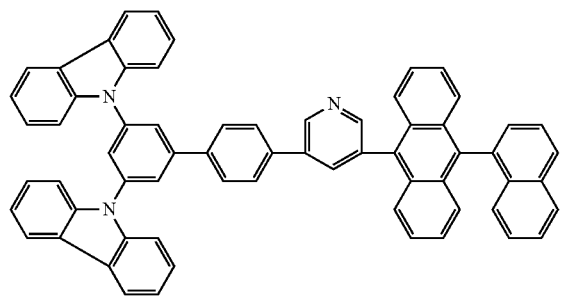
[Chemical Formula 1-24]
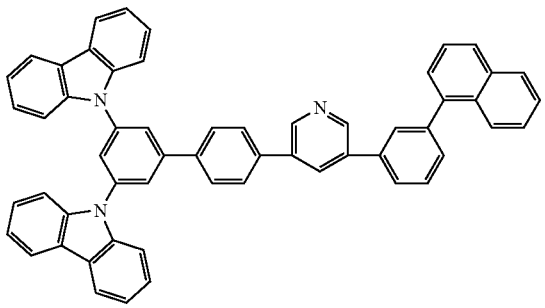
[Chemical Formula 1-25]
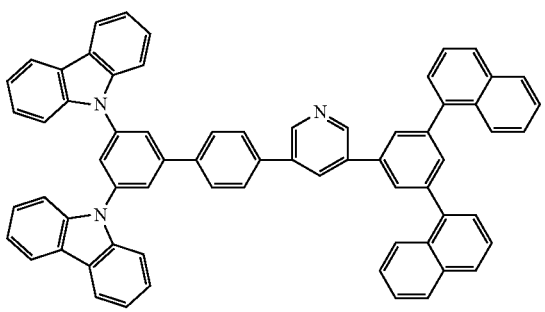
[Chemical Formula 1-26]
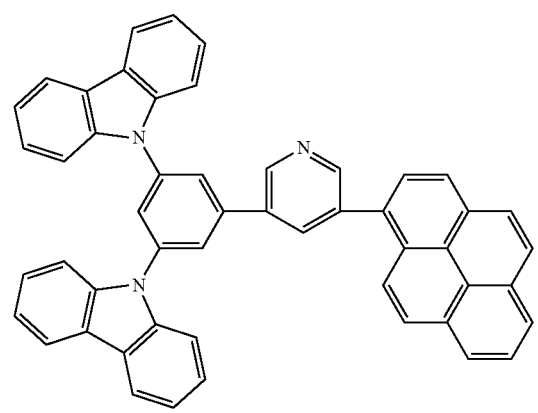
[Chemical Formula 1-27]
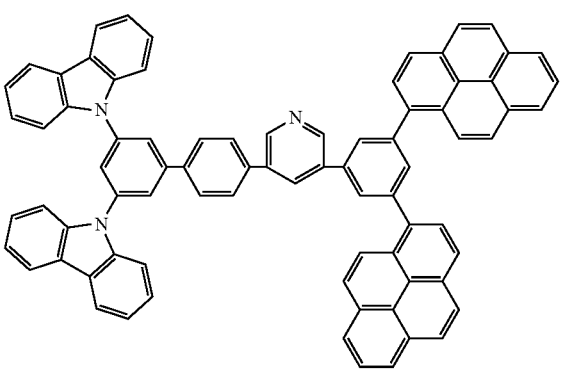

[Chemical Formula 1-30]
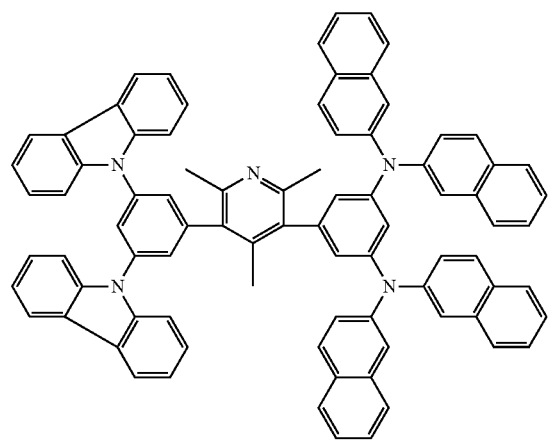
[Chemical Formula 1-36]
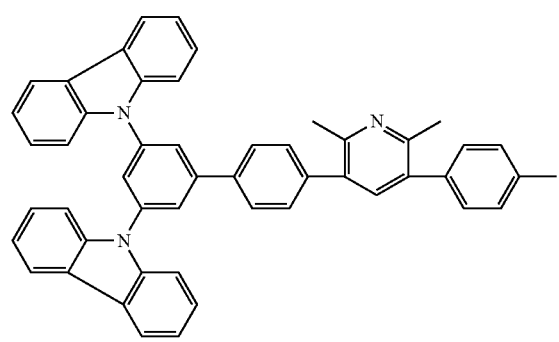
[Chemical Formula 1-37]
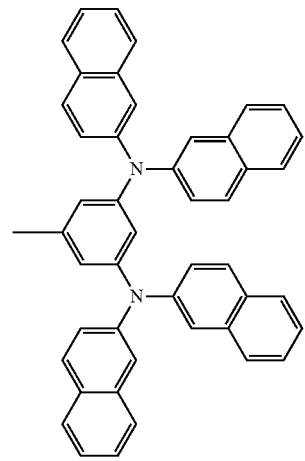
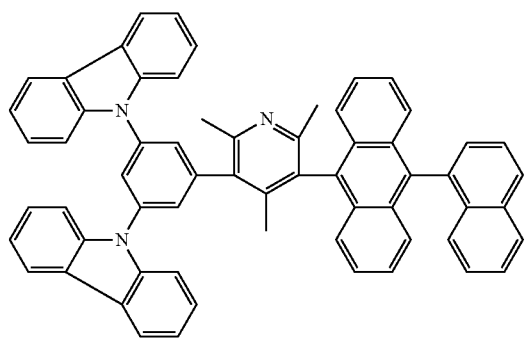
[Chemical Formula 1-38]
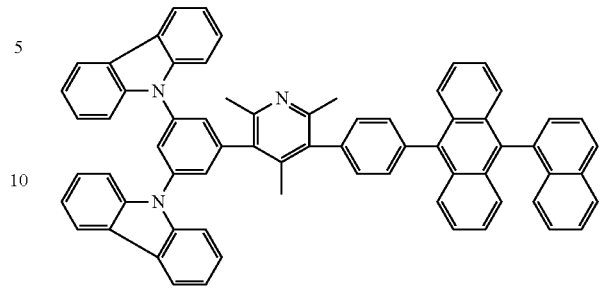
[Chemical Formula 1-39]
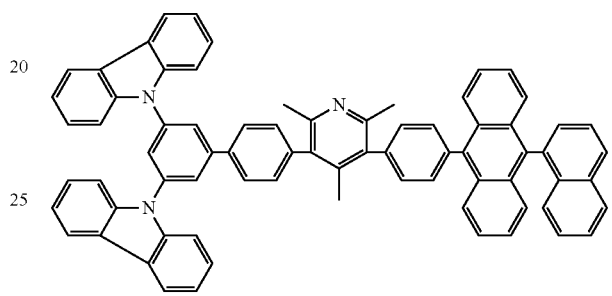
[Chemical Formula 1-40]
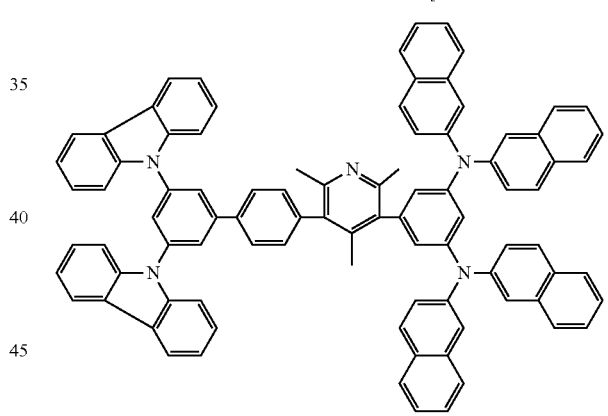
[Chemical Formula 1-41]
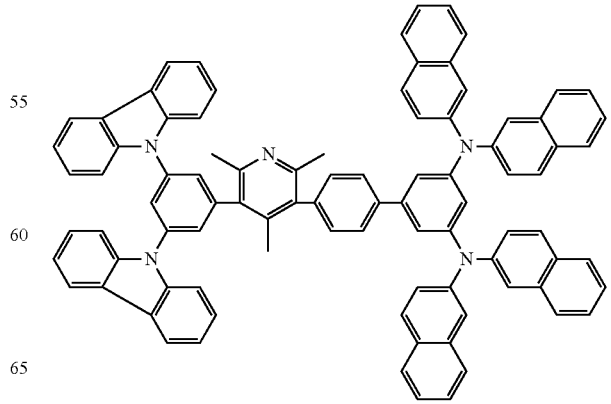

-continued
[Chemical Formula 1-42]
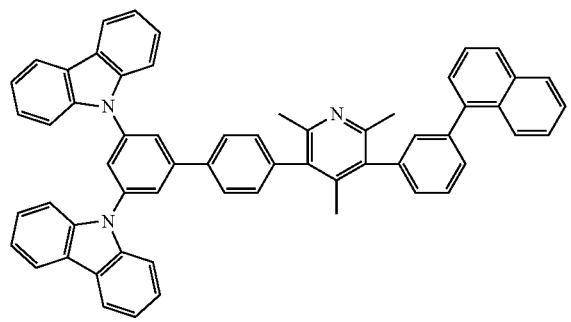
[Chemical Formula 1-43]
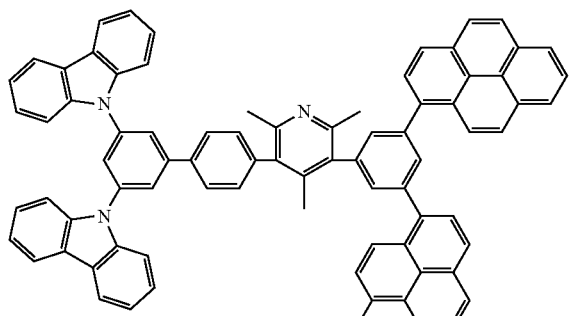
[Chemical Formula 1-44]
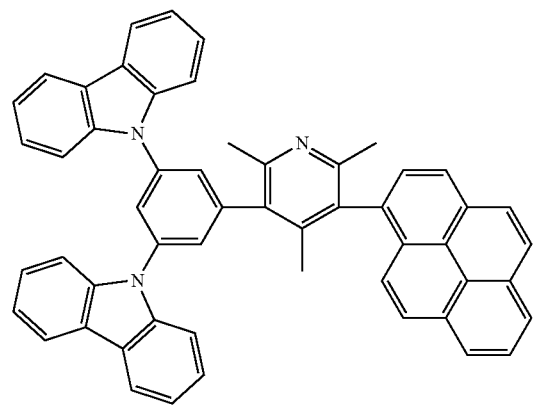
-continued
[Chemical Formula 1-45]
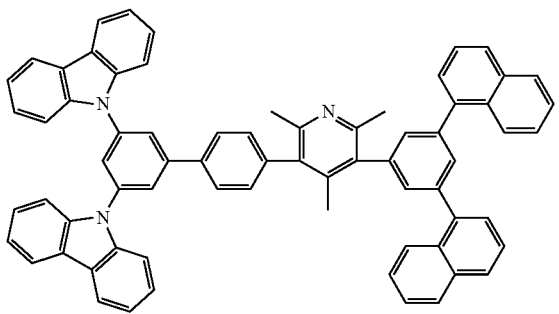
[Chemical Formula 1-52]
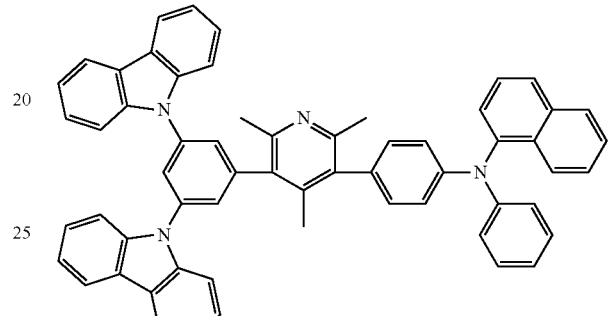
[Chemical Formula 1-53]
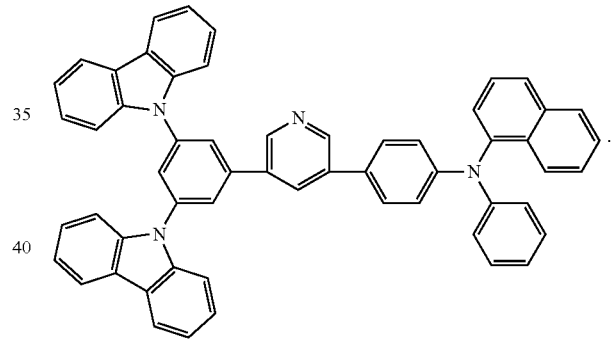
* * * * *